United States Patent
Izatt et al.

(10) Patent No.: US 6,564,089 B2
(45) Date of Patent: May 13, 2003

(54) OPTICAL IMAGING DEVICE

(75) Inventors: Joseph A. Izatt, Pepper Pike, OH (US); Michael V. Sivak, Cleveland Heights, OH (US); Andrew Rollins, Bedford, OH (US); Akihiro Horii, Hachiouji (JP); Tadashi Hirata, Hachioji (JP); Shuhei Iizuka, Hachioji (JP)

(73) Assignees: University Hospital of Cleveland, Cleveland, OH (US); Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/087,907

(22) Filed: Mar. 5, 2002

(65) Prior Publication Data

US 2003/0004412 A1 Jan. 2, 2003

Related U.S. Application Data

(63) Continuation of application No. 09/315,982, filed on May 21, 1999.
(60) Provisional application No. 60/118,807, filed on Feb. 4, 1999.

(51) Int. Cl.[7] .................................................. A61B 6/00
(52) U.S. Cl. ...................................................... 600/478
(58) Field of Search ................................. 600/478, 318, 600/342; 351/215, 205, 221; 356/450, 477, 479, 484, 487; 250/227.11, 227.27, 235

(56) References Cited

U.S. PATENT DOCUMENTS

| 5,321,501 A | 6/1994 | Swanson et al. |
| 6,053,613 A | 4/2000 | Wei et al. |
| 6,069,698 A | 5/2000 | Ozawa et al. |
| 6,134,003 A | 10/2000 | Tearney et al. |
| 6,293,674 B1 | * 9/2001 | Huang et al. ............... 351/221 |
| 6,307,633 B1 | * 10/2001 | Mandella et al. ........... 356/479 |

FOREIGN PATENT DOCUMENTS

WO   WO 97/32182   9/1997

OTHER PUBLICATIONS

Kersey et al., "Polarisation–Insensitive Fibre Optic Michelson Interferometer," Electronics Letters, Mar. 14, 1991, vol. 27, No. 6, pp 518–520.
Rollins et al., "In Vivo Video Rate Optical Coherence Tomography," ©1998 Optical Society of America, 11 pages.
Tearney et al., "In Vivo Endoscopic Optical Biopsy With Optical Coherence Tomography," Science, vol. 276, Jun. 27, 1997, pp. 2037–2039.

* cited by examiner

Primary Examiner—George Manuel
(74) Attorney, Agent, or Firm—Pilsbury Winthrop LLP

(57) ABSTRACT

An Optical Coherence Tomography (OCT) device irradiates a biological tissue with low coherence light, obtains a high resolution tomogram of the inside of the tissue by low-coherent interference with scattered light from the tissue, and is provided with an optical probe which includes an optical fiber having a flexible and thin insertion part for introducing the low coherent light. When the optical probe is inserted into a blood vessel or a patient's body cavity, the OCT enables the doctor to observe a high resolution tomogram. In a optical probe, generally, a fluctuation of a birefringence occurs depending on a bend of the optical fiber, and this an interference contrast varies depending on the condition of the insertion. The OCT of the present invention is provided with polarization compensation means such as a Faraday rotator on the side of the light emission of the optical probe, so that the OCT can obtain the stabilized interference output regardless of the state of the bend.

16 Claims, 46 Drawing Sheets

FIG.6
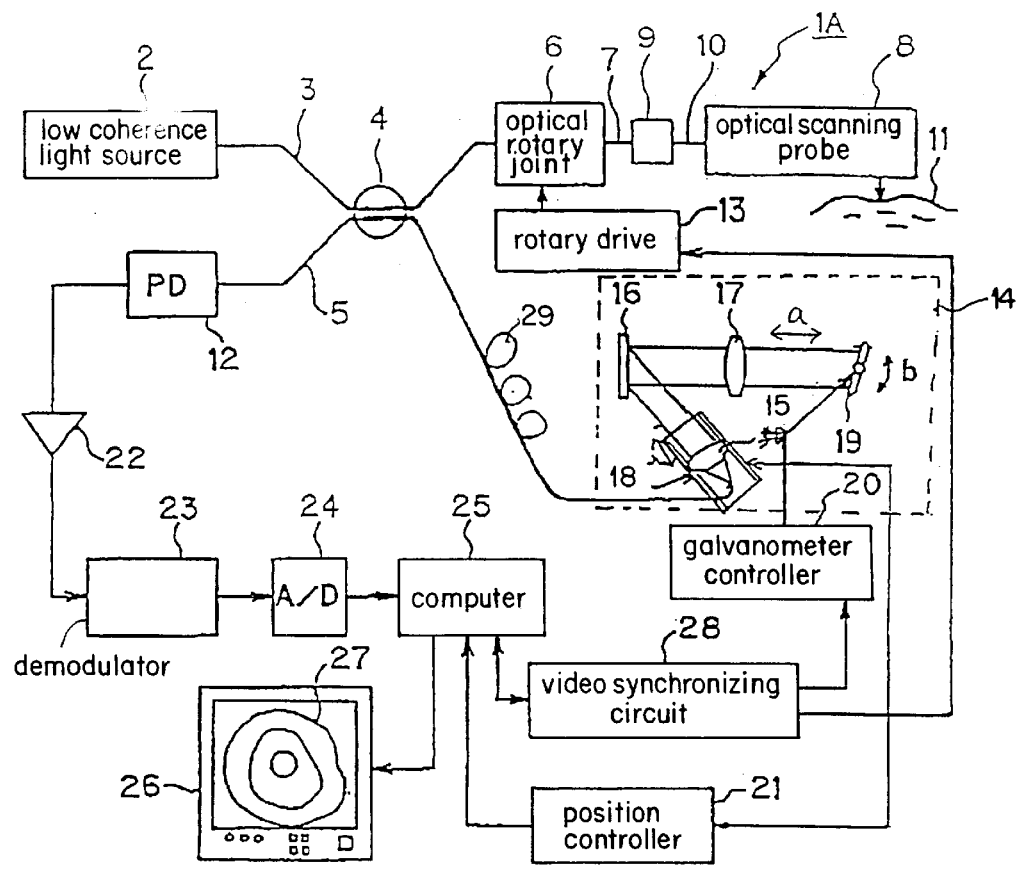
FIG. 7
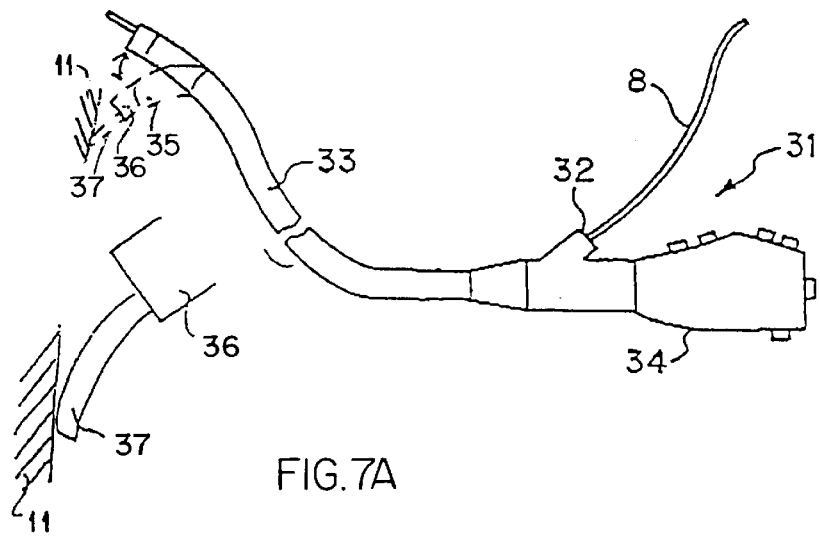
FIG.7A

- Forward Mapping: $x(r,\theta) = r\cos(\theta)$
  $y(r,\theta) = r\sin(\theta)$

- Backward Mapping: $r(x,y) = \sqrt{x^2 + y^2}$
  $\theta(x,y) = \tan^{-1}\left(\dfrac{y}{x}\right)$ FIG.29
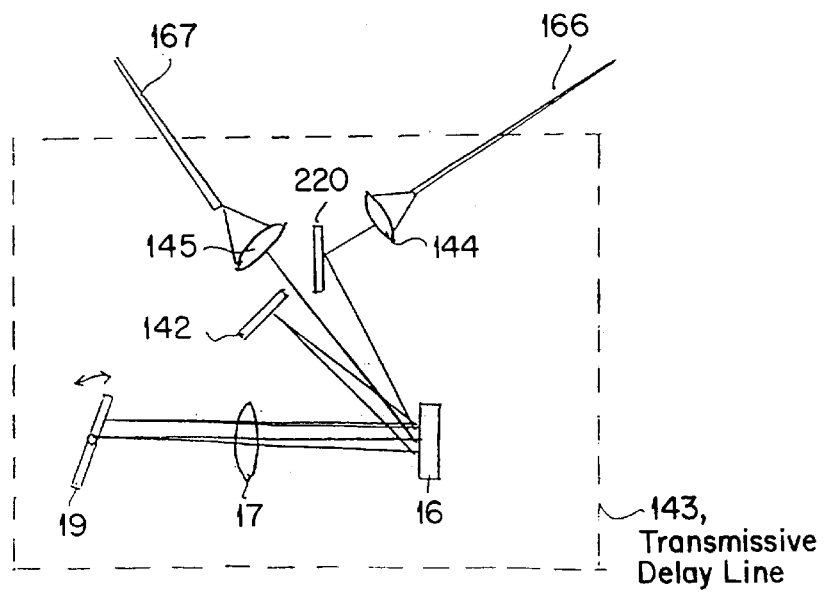
143, Transmissive Delay Line
FIG.30
| $a_1$ | $b_1$ | | | $c_1$ | $d_1$ |
|---|---|---|---|---|---|
| $a_2$ | $b_2$ | | | $c_2$ | $d_2$ |
FIG.31
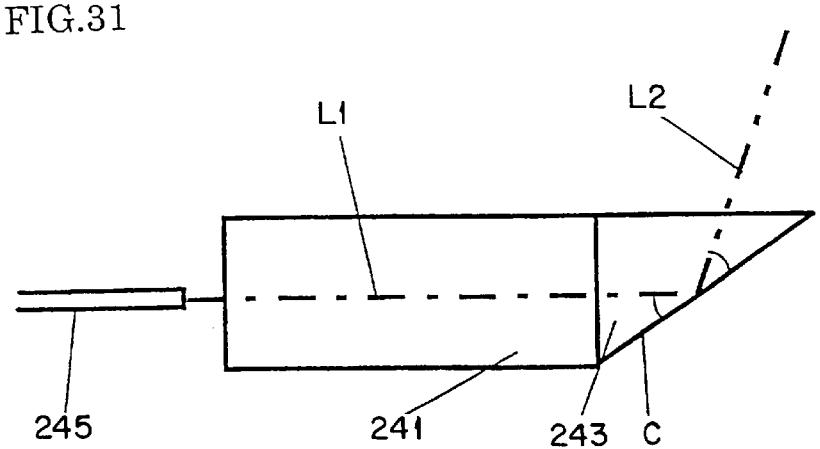

Partially Enlarge

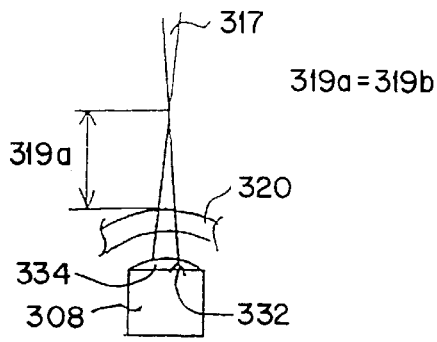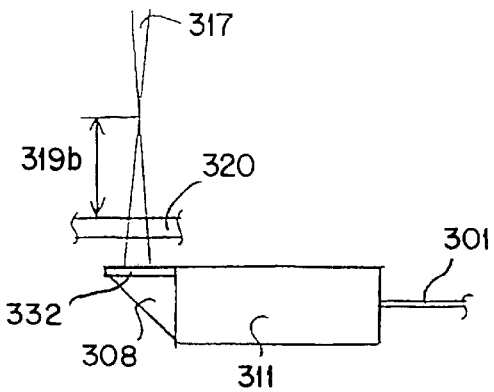
FIG. 46A  FIG. 46B
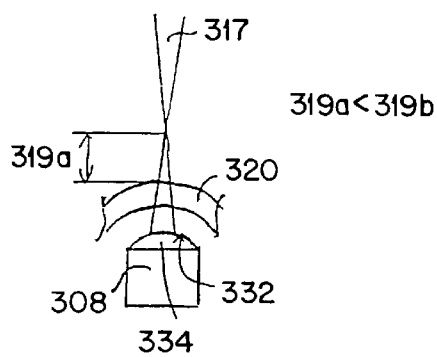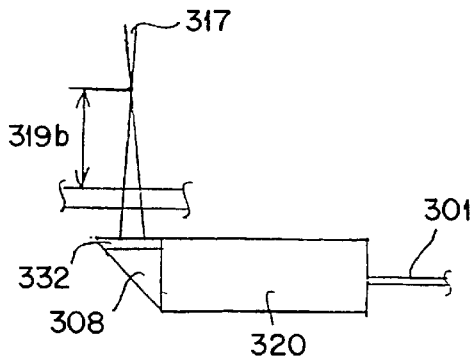
FIG. 47A  FIG. 47B
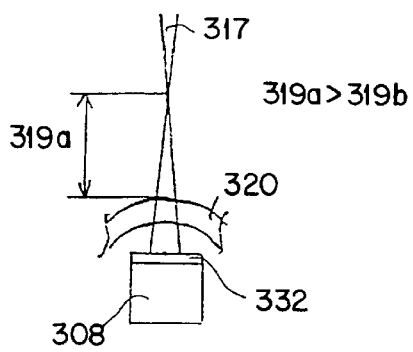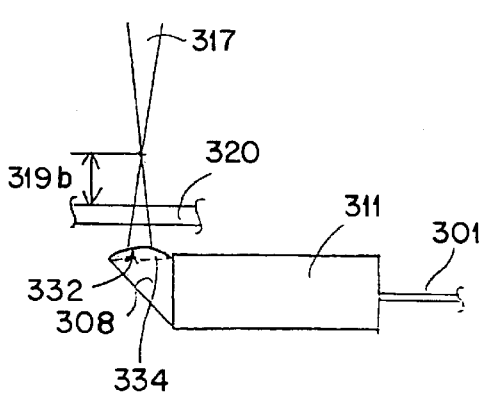
FIG. 48A  FIG. 48B

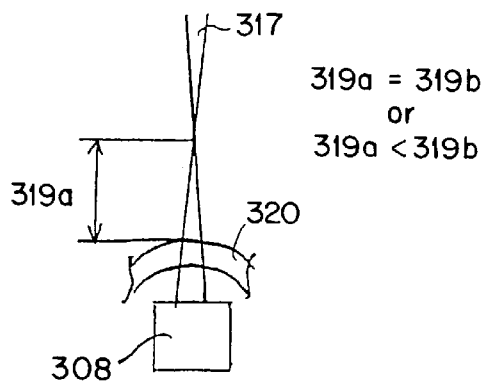
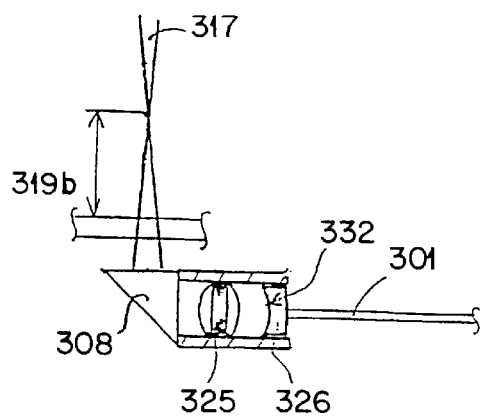
FIG. 49A  FIG. 49B
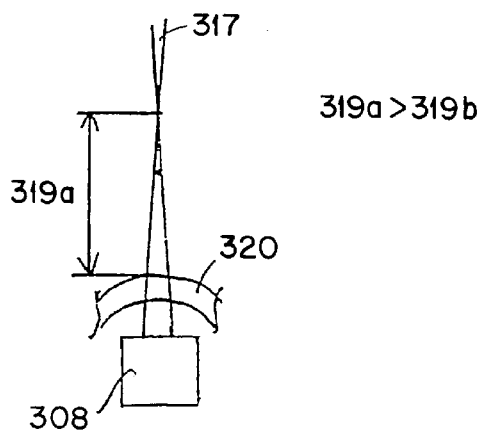
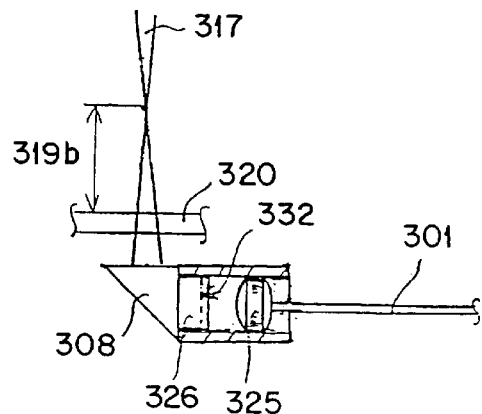
FIG. 50A  FIG. 50B

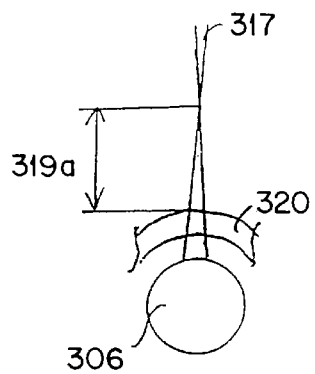
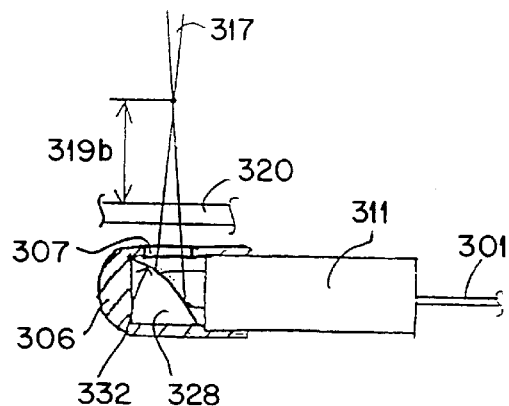
FIG. 53A  FIG. 53B
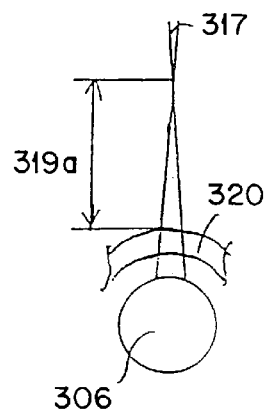
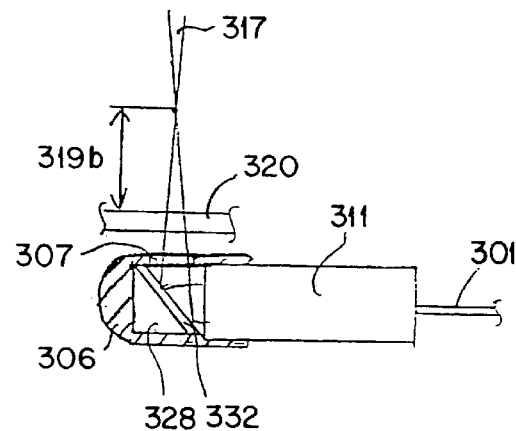
FIG. 54A  FIG. 54B

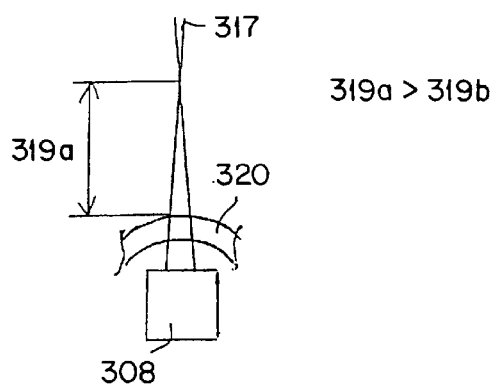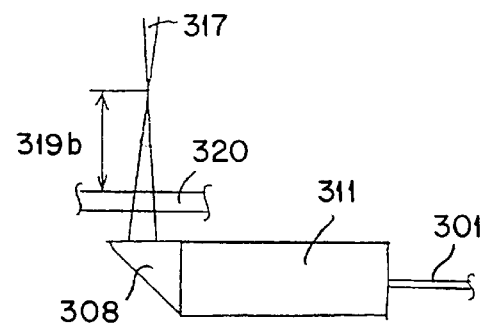
FIG. 57A
(RELATED ART)
FIG. 57B
(RELATED ART)

OPTICAL IMAGING DEVICE

CROSS REFERENCE TO RELATED APPLICATION

This application is a continuation of U.S. application Ser. No. 09/315,982, filed May 21, 1999, now abandoned, which claims priority to U.S. Provisional Application No. 60/118,807 filed Feb. 4, 1999, now abandoned, the specification and drawings of which are incorporated by reference herein in their entirety.

BACKGROUND OF THE INVENTION

1. Field of the Invention

The present invention relates to an optical imaging device which irradiates the subject with low coherence light, to produce a tomogram of the subject, from data on light scattered by the subject.

2. Description of Related Art

Recent U.S. Pat. No. 5,321,501, for example, discloses a device which can obtain optical information from the inside of the tissue, in order to diagnose the biological tissue, and which performs optical coherence tomography (OCT) of interference type, using low coherence light, to produce a tomogram of the subject. U.S. Pat. No. 5,321,501 also discloses an optical probe which has a flexible insertion unit to be introduced into the patient's body cavity, and which enables the doctor to introduce the insertion unit into a blood vessel, using an optical probe that includes a single mode fiber for sending low coherence light to the inside so that the doctor can observe the inside of the patient's body cavity, using a catheter or endoscope. When introduced into the patient's body cavity, the optical probe is necessarily bent according to the tortuosity of the body cavity. Because of the bending, stress-induced birefringence is induced in the optical fiber which varies according to the extent of the bending. In OCT, the doctor uses an interference signal of a reference beam with reflection from the subject, to observe the subject. It is necessary, generally, to orient polarization of the reflection from the subject, toward that of the reference beam so that interference with the reference beam may be maximized. The stress-induced birefringence varies depending on the bending in the patient's body cavity; polarization, therefore, varies depending on the bending. As introduced into the patient's body cavity, the insertion unit varies interference contrast. The doctor may turn an integrated irradiation optical system that includes the single mode fiber. Every rotation of the bent system, particularly in such cases, causes a great variation in the stress-induced birefringence of the fiber. Interference contrast varies, so that detection sensitivity greatly varies depending on the direction of rotary scanning. Such a great variation is a problem.

"Polarization-insensitive fiber optic Michelson interferometer" (Electr. Lett. Vol. 27, pp. 518–519, 1991) discloses a method of inserting an element that rotates polarization by 45 degrees in a non-reciprocal manner such as a Faraday rotator, in order to compensate for a variation in interference contrast due to the fluctuations in stress-induced birefringence of such a fiber. A general Faraday rotator, however, requires a garnet crystal, and magnetic material that provides a magnetic field for the garnet crystal. It is impossible to provide such substances at the narrow probe tip to be introduced into the patient's body cavity.

"In vivo video rate optical coherence tomography" (A. M. Rollins et al., Internet, 1998 Optical Society of America) discloses a method of high-speed scanning of an interference location in OCT, with the reference arm group delay mechanism using a galvanometer mirror. To scan the location at a high speed by rotating the mirror, the inertia of the mirror will dictate that the rotational position of the mirror, if plotted with respect to time, would approach a sine wave oscillation. The depth scan of the interference location is proportional to the mirror rotational position. Because the mirror rotates first in one direction and then in the other, it is difficult to reproduce a two-dimensional image from the obtained interference signals. If the device uses an interference signal obtained by scanning in only one direction, it will neglect half the actually obtained signal data. In such cases, if the doctor continues rotary scanning of the optical system in the optical probe, he or she will provide only half the resolution and dynamic range for a two-dimensional image. Such a decrease in resolution and dynamic range is a problem.

In the above-mentioned high-speed scanning, the use of a resonant scanner, for example, ensures that the time vs. scanning angle curve is a sine wave, not linear. A two-dimensional position and intensity graph, however, may be used to represent an interference signal. Otherwise a shaded image may be used to express intensity as shades, based on the two-dimensional interference locations and detection positions. In such cases, to display interference signals accurately, it is impossible to use the interference signals obtained in time series, because the interference signals are linear with respect to time, and because the interference location is nonlinear with respect to time. A tomogram of the biological tissue inside, for example, may be produced. In such cases, if the device fails to indicate accurately the interference location and the detection position, the image produced will be warped, and it is impossible to accurately measure length with a scale.

As described above, the device may use a nonlinear scanning means such as a resonant scanner. Depending on the scanning angle, in such cases, the Doppler frequency (which characterizes the interference signal produced) varies in proportion to the scanning speed of the interference location. Optical heterodyne detection in OCT uses this Doppler frequency for detection; therefore, it ensures high signal-to-noise ratio. If the scanning is nonlinear, the Doppler frequency may vary. In such cases, if the frequency characteristics of the demodulator circuit are set so that the demodulator can detect all possible interference frequencies in a wide range, then the detection will include excess noise, and result in a decrease in the signal-to-noise ratio. The inferior signal-to-noise ratio is a problem.

If the subject is scanned in a two-dimensional manner, methods of enlarging a part of the displayed image include: a method of cutting unnecessary parts away from that part; and a method of changing the scanning range. Changing the scanning range may require adjusting the speed of scanning the interference location, to the change in scanning range. To improve the signal-to-noise ratio, scanning the interference location may be slowed. In these cases, the Doppler frequency may also vary; therefore, setting the frequency characteristics of the demodulator will pose a similar problem.

As disclosed in U.S. Pat. No. 5,321,501, an optical probe to be introduced into the patient's body cavity, generally, needs to be detachable from the observation device body for the purpose of cleaning and sterilizing. If detachable, a broken optical probe can be easily replaced with a new one. During assembly, single mode fibers undergo various stresses. Consequently, when provided in each optical probe, each single mode fiber may produce a distinct intrinsic birefringence. Whenever replacing probes, the doctor has to use a polarization plane adjustment means to orient, toward polarization of the reference beam, polarization of reflection that can be obtained by the optical probe, from the subject. It is necessary to maximize contrast of interference with the reference beam. The work is troublesome.

As disclosed in "In vivo video rate optical coherence tomography" (A. M. Rollins et al.), a galvanometer mirror or resonant scanner mirror may be used for high-speed scanning of the interference location in OCT. Because of the inferior temperature characteristics, the galvanometer mirror and the resonance scan mirror vary the scanning range and scanning speed, depending on the variation in temperature.

As disclosed in the above cited Rollins et al. Publication "In vivo video rate optical coherence tomography", a galvanometer mirror or resonant scanner mirror may be used for high-speed scanning of the interference location in OCT. In such cases, in order to maximize drive speed, the mirror will be driven so that the drive curve may approach a sine wave. As described above, the nonlinear drive results in a nonlinear relationship between the interference location and interference signals obtained in time series. Such a nonlinear relationship is difficult to handle. The inferior signal-to-noise ratio, aggravated by setting the frequency characteristics of a demodulator, is a problem.

When displayed on the screen, an OCT tomogram is drawn using optical length, which greatly differs depending on the medium. As the medium, air, for example, has a refractive index n of approximately 1; whereas the biological tissue has a refractive index n of 1.3 to 1.5. When displayed on the screen, optical length is n times the actual length. Such difference causes a significant error, and that is a problem.

The outer sheath with optical permeability is generally made of a resin tube such as fluorine resin and polyamide (nylon). Since the refractive index of the resin tube greatly differs from that of air sealed between the optical element and the outer sheath, significant light reflection occurs at the index of refraction interface between the air inside the outer sheath and the sheath material itself. Similarly, significant reflection also occurs at the index of refraction interface between the outer sheath surface and the air, water or gastrointestinal fluid outside the sheath. The reflection attenuates the irradiation and observation light, thus degrading the S/N ratio for observation.

Since OCT, in principle, detects the correlation between the reflection intensity on the optical path and the optical path length, presence of two faces with intense reflection in the vicinity will cause a degradation in the amount of optical power available for image formation. They will also result in the formation of reflections at the probe sheath surfaces which could be large compared to any tissue reflections, and will thus tend to overwhelm the dynamic range of the detection electronics and make it difficult to display weak tissue reflections on the same screen as the strong sheath reflections. Furthermore, multiple reflections may form between the reflecting surfaces, resulting in the generation of ghost images of the tissue where no actual reflection surface exists. The observation light, which is light scattered and reflected by the living body, is relatively weak light when compared with the above mentioned reflection intensity, the ghost will considerably deteriorate the observation performance. This is especially damaging if the ghost image appears at the same location as the actual tissue image, in which case there is no simple way to separate them.

On the other hand, "In vivo Endoscopic Optical Biopsy with Optical Coherence Tomography" (G. J. Tearny et.al, Science vol.276) disclosed an OCT optical probe which has a transparent sheath to cover and seal up to the optical element such as the prism at the tip end.

The prior art suffers from problems that when the endoscope with the probe inserted through its insertion opening is inserted into a body cavity or when the probe is bent, the rotating support for the optical element at the tip end comes into contact with the interior of the outer sheath and damages the interior, that optical characteristics of the outer sheath are degraded by irregular reflection of lights at the damaged portion, and that the observation quality deteriorates as the OCT irradiation light emitted by the optical element and observation light reflected by the living body are shielded.

Even when the damage on the sheath does not coincide with the irradiation or observation light position, the damage appears at the location of observation light since the rotary sheath reciprocates against the outer sheath because of the bending shape of the probe.

Furthermore, probe sheaths made from such materials as fluorine resin and polyamide have very poor optical quality, such that they have randomly spaced internal index of refraction boundaries, internal striations, and particulate scatterers which act to degrade the wavefront of light propagating though them and to scatter a significant portion of light into unpredictable directions. Since the probe design depends upon light being directed to a diffraction-limited focussed spot in the tissue and then being re-coupled into the single mode fiber on the return path, any passage through elements which degrade the optical wavefront or scatter light severely degrades the re-coupling of image-forming light into the probe and the heterodyne efficiency of the OCT interferometer. Thus, a probe window of high optical quality would be highly advantageous to obtain the best possible OCT image quality.

As mentioned above, recently an OCT device has been developed for observing tomography structure of a living body by using a low coherence light length of interference. For observing the tomography structure by using the low coherence light, a method is used for dividing light from a light source for generating the low coherence light into signal light and reference light, irradiating the signal light to an observed object, after that, composing the reflected light from the object measured with the reference light again, and detecting the interference light between both of them. Then, as it is possible to obtain the interference light at only the place that length of an optical path of a flux of the signal light is agreed with that of the reference light when changing the length of the optical path on the side of the reference light, it is possible to obtain the same effect as scanning the place for observing the measured object by changing the length of the optical path on the side of the reference light, and to possible to observe the tomography structure of the measured object.

FIG. 1 shows an example that of OCT is applied to an endoscope. The light from a low coherence light source 202 is combined with a single mode fiber 205 and is led to a coupler 204. The light is divided the light into the signal light 206 and the reference light 207 by the coupler 204. The light on the side of the reference light 207 divided is lead via lens 209 to a means 214 (scanning mirror) for changing the optical path 214 by the single mode fiber 205. The light returned from the means for changing the optical path 214 is returned to the coupler 204 by the single mode fiber 205 again.

On one hand, the light divided on the side 206 of the signal light is led to the end optical system 208 on the side of the signal light 206 by the single mode fiber 205 different from on the side of the reference light 207, irradiated to the measured object, reflected from the measured object, returned, therefore, is composed to the light returned from the side of the reference light by the coupler 204 through the end optical system on the side of measuring and the single mode fiber again. The composed light returned on the side of referring and measuring is led to a detector 212 by the single mode fiber 205 and the interference signal is detected by the detector 212.

FIG. 2 is a cross-sectional view showing non-prior art enlarged details of an end part on the side of measuring in the FIG. 1.

The end optical system 208 is constructed at the end of the single mode fiber 205. In the end optical system, a lens unit 220 contains a refractive index distribution lens (Gradient Index lens: GRIN lens) 221 for gathering the light to a living body, a Faraday rotator 222 for canceling the influence of polarization caused by bending of the single mode fiber 205 and prism 223 for changing the direction of the light. Further, the cylindrical transparent sheath 225 covers the outside of the lens unit. As shown by arrow 219, the single mode fiber 205 and the lens unit 220 are rotated as the longitudinal direction (the central axis of the cylindrical sheath 225) is an axis. As above mentioned by rotating the mechanism, it is possible to observe the measured object not only in the cross-sectional direction but also radially.

In the above described related art, the end optical system 208 has a problem in that after light outgoing from a single mode fiber 205 is reflected several times on the boundary surface of a optical elements such as a Faraday rotator 222, a refractive index lens 221, prism 223 and sheath 225 and returned to the single mode fiber 205 again, an image of a living body and ghost overlaps and quality of the picture is degraded.

The reasons for that are described in reference FIGS. 3(A)–3(E).

FIGS. 3(A) through 3(E) show an example of causes for generating ghosts, and behavior of the light outgoing from the single mode fiber is schematically shown as time passes.

FIG. 3A: When the light outgoing from a single mode fiber 205 comes to the boundary surface between the refractive index distribution lens 221 and a Faraday rotator 222, part of the light, light a, but part b penetrates is reflected rearwardly toward the single mode fiber 205 again.

FIG. 3B: Light b is then again reflected by the rear surface of the refractive index distribution lens 221 and is directed toward the object. Light a, however, passing as it was in the FIG. 3A, proceeds through the Faraday rotator (FR) 222 and the prism 223 to the middle of the sheath 225 and the tissue 226 of a living body.

FIG. 3C: Light a is reflected in tissues 226 of a living body and directed back toward the single mode fiber 205. Meanwhile, light b is proceeding though the refractive index distribution lens 221 to the side of the object.

FIG. 3D: Light b is reflected on the boundary surface between prism 223 and FR 222, and is directed back toward the single mode fiber 205 again. Then, light a arrived at the boundary surface between the prism 223 and the FR 222, and overlaps light b.

FIG. 3E: Overlapped light a and light b is return to the single mode fiber 205.

In case of the conditions above mentioned, the signal light from the tissue 226 of the living body and light b reflected in the end optical system several times overlap, and an image when seeing the tomography structure of the living body is that the image 228 (FIG. 4) of the ghost due to light b overlaps the image 227 of the tissue of the living body.

The image 228 of the ghost is often remarkable when the number of times of reflection on the end surface of the optical element is less than three times. Generally, as strength of reflection per surface of the optical element is fromis −20 dB to −30 dB relative to the incident light, when the number of times of reflection on the end surface of the optical element is three times, total strength of reflection is from −60 dB to −90 dB, and when the number of times of reflection is four times, it is from −80 dB to −120 dB. On the other hand, strength of the signal from the living body is −50 dB to −70 dB. Therefore, when the number of times of reflection on the end surface of the optical element is even less than three times, it can be almost the same level as the strength of the signal of the living body and causes difficulty in observation.

The path of the reflective light as above mentioned is an example; multiple reflection in the real end optical system occurs in various paths except besides the path as above mentioned. Particularly, there are problems when the shape of the sheath is cylindrical because it is difficult to treat to prevent reflection from the surface of the sheath, and it is easy then for light reflected three times to overlap on the observing position.

One more problem of the above mentioned end optical system is the structure of the end optical system in that the light outgoing from the single mode fiber is reflected on the boundary surface of the optical element and the reflected light is directly returned to the single mode fiber 205. If the such structure as is called the structure of once reflection, "structure of once reflection", in the optical system, the structure of once reflection will reflect the reflected light from all the boundary surfaces except the end surface on the side of the fiber of the refractive index distribution lens.

If the structure of the optical system is the structure of once reflection and the light reflected from the end surface of the optical element is incident on the single mode fiber, unnecessary light will return to the single mode fiber and an S/N ratio when detecting the interference signal will be significantly reduced. Therefore, if the structure of the optical system is the structure of once reflection, it will be hard to see an observing screen.

FIGS. 5A and 5B show an example of the structure of once reflection that the light is reflected on the boundary surface between a Faraday rotator 222 and prism 223, wherein FIG. 5A represents the actual optical path, and FIG. 5B represents by folding the optical system from the reflected surface so that it is easy to understand the optical path. It is known from FIG. 5A that the reflected light returns to the single mode fiber 205 again. In the optical system, the light reflected by another boundary surface returns to the single mode fiber 205 again similarly to the example as above mentioned.

Next, FIG. 57A is a schematical view showing an end optical system of an optical scanning probe from the side of en end and FIG. 57B is a schematical view showing from a side surface. As shown in FIGS. 57A and 57B, the end optical system includes a transparent Teflon tube 320, a prism 308, a GRIN lens 311 and a single mode fiber 301. Light guided into the single mode fiber 301 is incident on GRIN lens 311, prism 308 and Teflon tube 320 and becomes an observing beam 317. The Teflon tube 320 has a concave lens effect in the peripheral direction of a cylindrical surface of the tube. Therefore, a focal distance 319 a in the peripheral direction to a sheath cylindrical surface of the observing beam 317 is longer than a focal distance 319 b in the longitudinal direction of the sheathe.

In the related art shown in the FIGS. 57A and 57B, relation of positions between the focal position 319a in the peripheral direction and the focal position 319b in the longitudinal direction to the sheath cylindrical surface of the observing beam 317 is fixed and impossible to change.

SUMMARY OF THE INVENTION

In view of the above problems of the related art, an object of the present invention is to provide a optical imaging device to compensate for a variation in interference intensity, due to the variation in birefringence of the fiber in an optical probe, even if the optical probe is bent in a patient's body cavity. Further, the optical imaging device provides a physically small birefringence compensation means such that it can be included at the optical probe tip. Further, the device compensates for a variation in interference contrast, due to the variation in birefringence of the fiber, caused by every rotation of the bent and turned system. Further, the device makes the birefringence compensation means of the Faraday rotator function effectively. Further, the device provides a physically small composition of the distal optical member for the optical probe.

Another object of the present invention is to provide an optical imaging device to obtain an interference signal corrected so that scanning can be regarded as performed in the same direction, even if the scanning direction oscillates due to the swing of the swing mirror in the propagation delay time-varying means. Further, the optical imaging device prevents the corrected interference signal from deviating, even if slight hysteresis or deviation, during scanning to and fro, is caused by the hysteresis of temperature characteristics and dynamic characteristics, when the device uses a high-speed scanning mirror, such as a galvanometer mirror and a resonance scan mirror in particular. Further the device performs the above-mentioned correction automatically.

Furthermore, an object of the present invention is to provide an optical imaging device to obtain an interference signal which is linear with respect to spatial distance from the probe tip, even if scanning the interference location is nonlinear with respect to time.

Furthermore, an object of the present invention is to provide an optical imaging device to enable the demodulator to detect the envelope of the interference signal with a high signal-to-noise ratio, even if the Doppler frequency of the interference signal is varied by the variation in speed of scanning the interference location.

Furthermore, an object of the present invention is to provide an optical imaging device to adjust the plane of polarization automatically.

Furthermore, an object of the present invention is to provide an interference location scanning means which has a scanning range and scanning speed that are difficult to disturb from the outside.

Furthermore, an object of the present invention is to provide an interference location scanning means which has the ability to perform high-speed scanning that is nearly linear.

Furthermore, an object of the present invention is to provide an optical imaging device to measure length on the screen correctly, whatever the refractive index may be.

Furthermore, an object of the present invention is to provide means for attenuating the reflection on the inner or outer surface of the outer sheath.

Furthermore, an object of the present invention is to make the inner side of the outer sheath resistant against damage by the rotating optical element and to have a sheath with good optical quality in the region of the probe where signal light is transmitted.

Furthermore, an object of the present invention is to provide an end optical system on the side of the signal light of OCT in which ghosts do not appear, the S/N ratio is good, and the ability to observe is excellent considering the problems as above mentioned.

Furthermore, an object of the present invention is to provide an optical scanning probe for advancing the S/N ratio.

Furthermore, another object of the present invention is to provide the optical scanning probe in which the observing depth degree is large Furthermore, an object of the present invention is to provide the optical scanning probe with optics that are easy to assemble and manufacture.

According to the present invention, variations in interference intensity, due to the variation in birefringence of the fiber in the probe, are compensated for, by the provision of a polarization compensation means on an optical path, from the emission end of the single mode fiber in the optical probe to the subject. Further, a physically small polarization compensation means can be provided at the optical probe tip, because the Faraday rotator uses a magnetic garnet crystal. Further, almost all substantially parallel rays incident on the Faraday rotator will cause the plane of polarization to rotate by 45 degrees accurately, to produce high efficiency in polarization compensation.

Further, according to the present invention, the device has a first memory means for preserving an interference intensity signal that corresponds to a particular one-way swing based on the detection by the reference position detection means, and a second memory means for preserving an interference signal that corresponds to a swing in the opposite direction to the particular one-way swing. Backward reading of data stored in the first memory means and forward reading of data stored in the second memory means produces interference signals that indicate scanning in the same direction. Further, different delays are provided for first memory means and the second memory means so that data, stored in the first memory means and the second memory means, may be read at delayed points of time. Controlling the delays correct hysteresis and deviation caused by slight differences in the scanning directions to and fro. Further, a reference signal is detected in each interference signal, and the delay setting means is adjusted so that both reference signals coincide with each other at the position of the reference signal. It is possible, thereby to correct automatically hysteresis and deviation caused by the to and fro scanning.

Further, according to the present invention, the use of a memory means for preserving interference intensity signals in time series, and a calculation means for calculating a memory address that corresponds to the interference location, to calculate the address, and to read data stored in the memory, produce an interference signal that corresponds to the interference location.

Further, according to the present invention, the device uses a calculation means to calculate the Doppler frequency of an interference signal produced by scanning the interference location. Changing the frequency characteristics of the demodulator, according to the calculated Doppler frequency, can constantly set the demodulator, to produce a high signal-to-noise ratio.

Further, according to the present invention, the device uses reference reflection means provided close to an end of the optical probe insertion unit, and obtains reflection data from the reference reflection means, in the form of an interference intensity signal produced from the interference means. Only setting a polarization adjustment means so that the interference contrast signal may be maximized, generally, is needed to adjust the plane of polarization for each probe automatically.

Further, according to the present invention, the propagation delay time-varying means has a dispersive means, imaging means, and reflection mirror. The reflection mirror includes a polygon mirror. The rotation of the polygon mirror enables scanning the interference location. It is easy to stabilize the scanning range and scanning speed, because the polygon mirror scanning is nearly linear with respect to the time series, and because it is easy to stabilize rotation speed.

Further, according to the present invention, when the reflection mirror is scanned by a resonant mechanical scanner, the scan becomes more linear by providing a specialized drive signal including one or more additional higher frequency harmonic components.

Further, according to the present invention, the optical imaging device comprises one or more scales that include a scale indicating an optical length in medium, or a scale indicating an optical length in the tissue, or a scale indicating optical length in the medium in those regions of the image representing the medium and which indicates optical length in the tissue in those regions of the image representing the tissue.

Also, a rigid light permeability part made from an optical quality material such as glass or fused silica has no internal index of refraction boundaries, striations, or scatterers, and can be manufactured or polished in such as way as to provide a good optical surface on the inside and the outside.

Further, according to the present invention, as light that the number of times of reflection on the end surface of an optical element of an end optical system on the side of signal light of an optical tomography diagnosis device is less than three times does not return to a single mode fiber, it is possible to obtain the end optical system on the side of the signal light of the optical tomography diagnosis device that ghost does not appear and a S/N ratio is advanced.

Further, according to present invention, by matching agreeing the focal position in the peripheral direction of the cylindrical surface of a sheathe with the focal position in the longitudinal direction of the sheathe and by concentrating the focal point to a point in an observing beam outgone from the optical scanning probe, an optical scanning probe for advancing the S/N ratio is provided.

Further, according to present invention, by making the beam spot diameter of an observing beam almost uniform over a long distance in the direction of the major axis of the observing beam., the optical scanning probe that observing depth degree is large is provided.

Further, according to the present invention, by placing reflection reduction coating inside or outside or both of the probe sheath, the reflection on the border of inner or outer medium to the sheath is reduced and thus the ghost and the light intensity reduction caused by reflection is avoided.

Further, according to the present invention, by placing a rigid light permeability part on the optical window where an optical emitter and receiver are located, the optical characteristics of the outer sheath are not degraded even when the rotating support for the optical element at the tip end comes into contact with the interior of the outer sheath. Also, a rigid light permeability part made from an optical quality material such as glass or fused silica has no internal index of refraction boundaries, striations, or scatterers, and can be manufactured or polished in such a way as to provide a good optical surface on the inside and the outside.

Further, according to the present invention, as light does not return to a single mode fiber when the number of times of reflection of light on the end surface of an optical element of an end optical system on the side of signal light of an optical tomography diagnosis device is less than three times, it is possible to obtain the end optical system on the side of the signal light of the optical tomography diagnosis device so that ghosts do not appear and the S/N ratio is advanced.

Further, according to the present invention, by matching the focal position in the peripheral direction of the cylindrical surface of a sheath with the focal position in the longitudinal direction of the sheath and by concentrating the focal point to a point in an observing beam outgone from the optical scanning probe, an optical scanning probe for advancing the S/N ratio is provided.

Further, according to present invention, by making the beam spot diameter of an observing beam almost uniform over a long distance in the direction of the major axis of the observing beam, the optical scanning probe that observing depth degree is large is provided.

BRIEF DESCRIPTION OF THE DRAWINGS

FIG. 6 is a block diagram showing an optical imaging device in the first embodiment of the present invention;

FIG. 7 shows an endoscope in use;

FIG. 7A is an enlargement of the dash line portion of FIG. 7;

Figure 20:
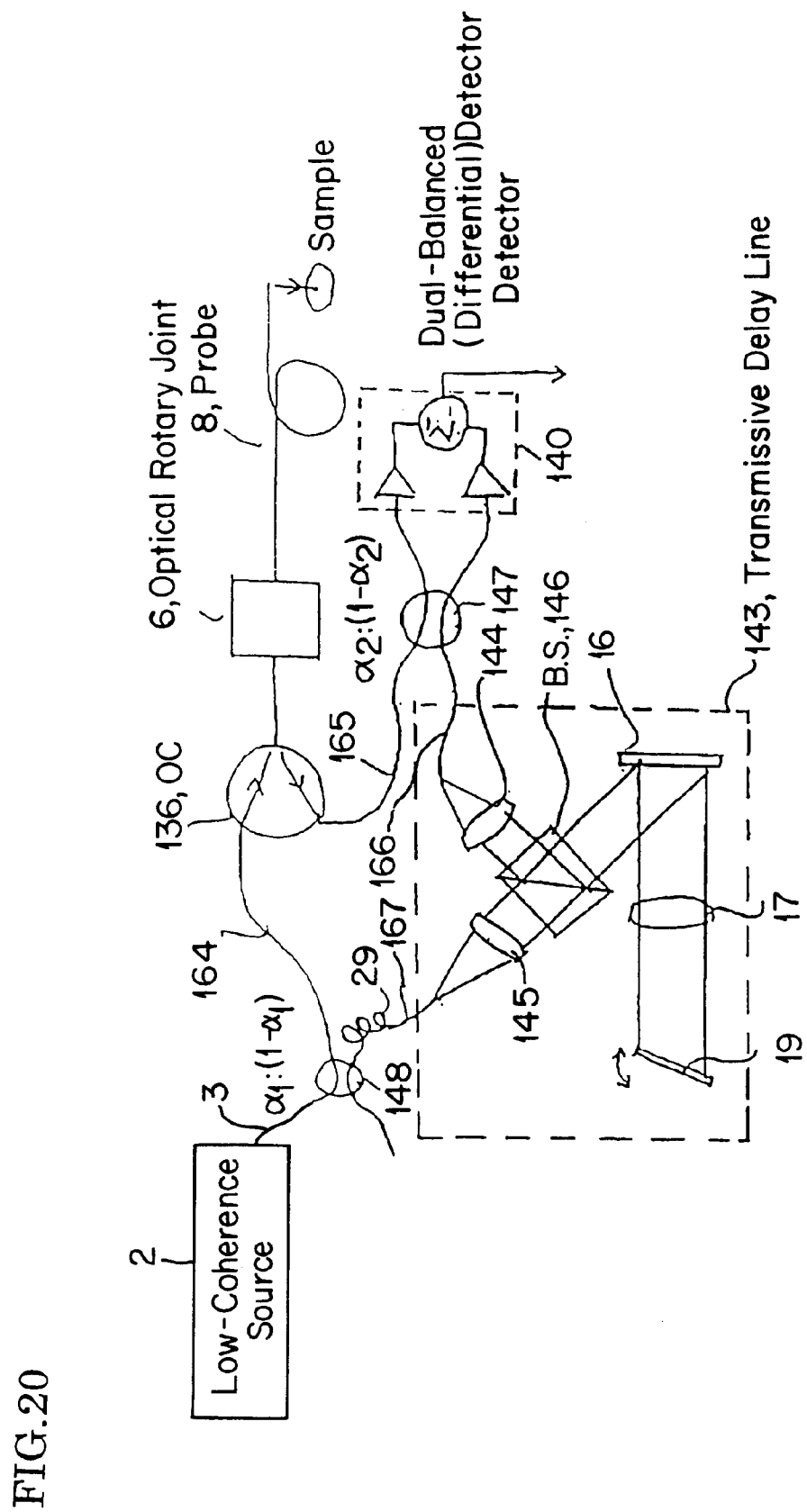
Figure 21:
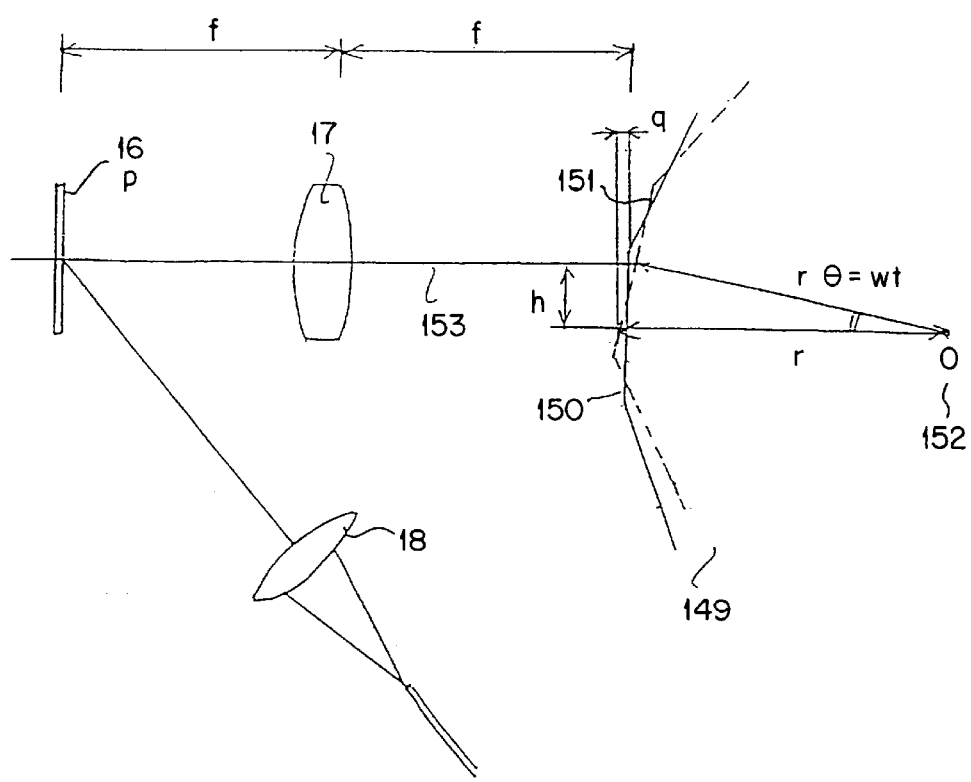
Figure 22:
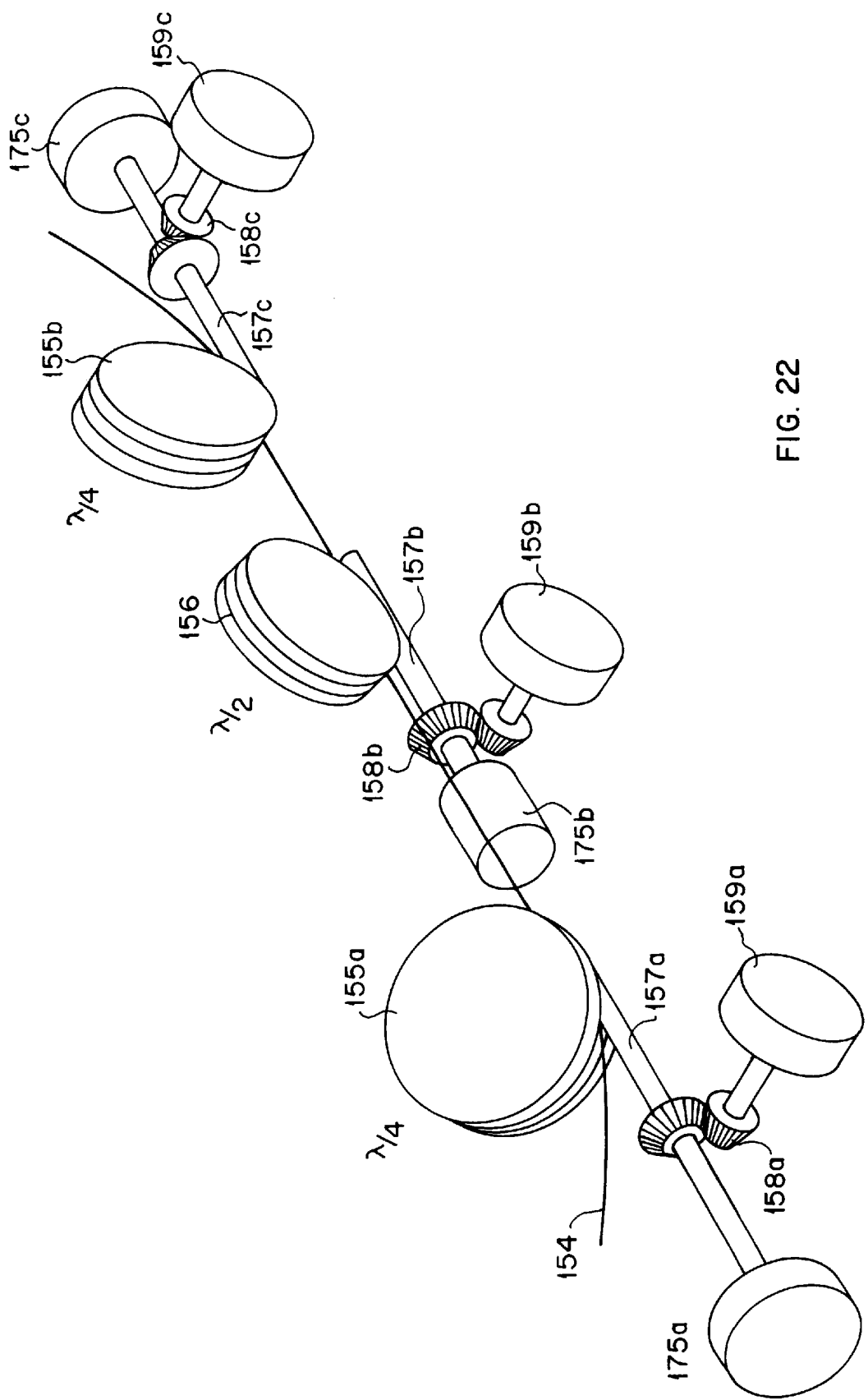
Figure 23:
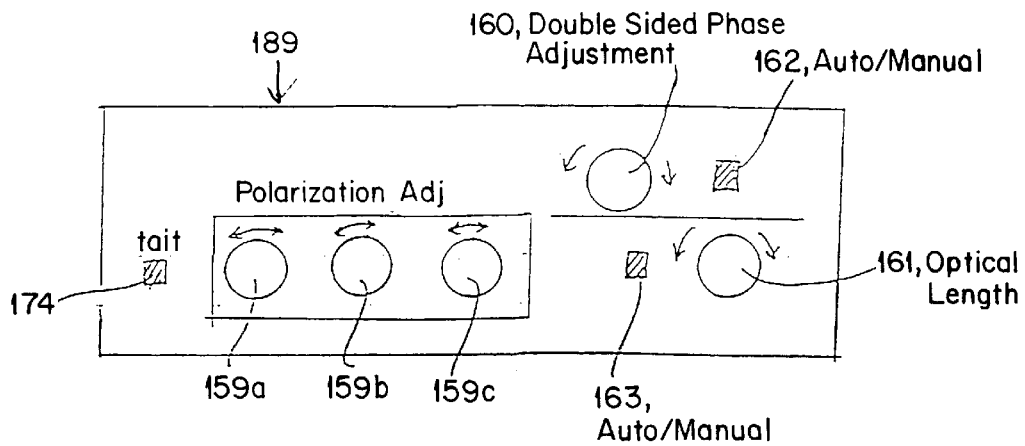
Figure 24A:
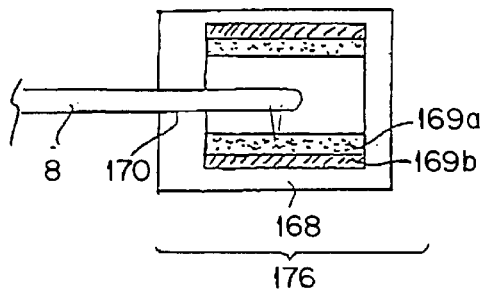
Figure 24B:
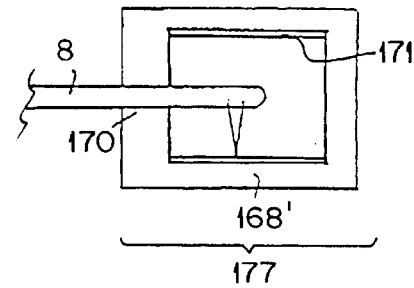
Figure 24C:
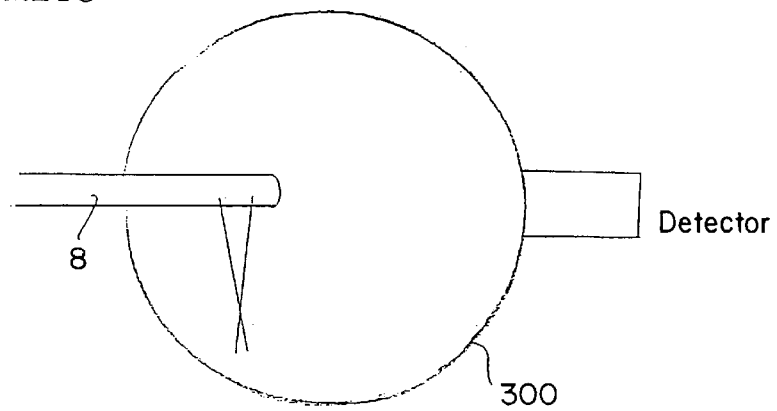
Figure 25:
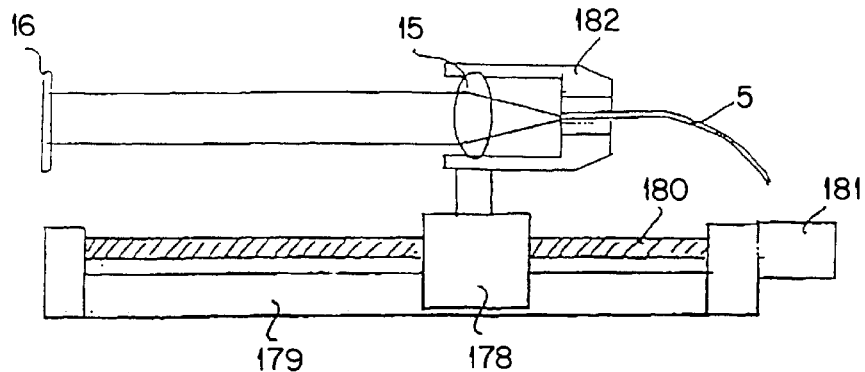
Figure 26A:
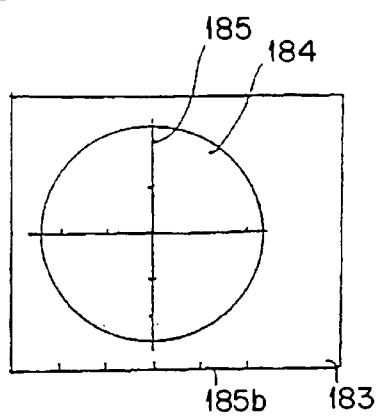
Figure 26B:
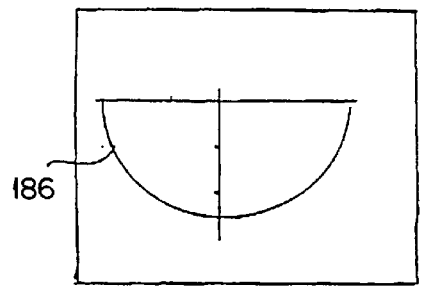
Figure 26C:
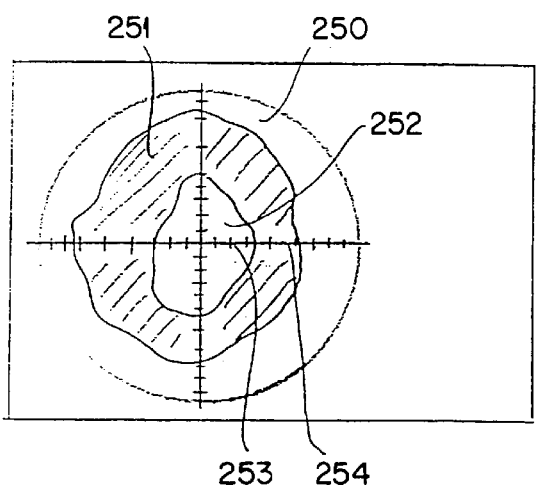

FIGURE modified 19 is a block diagram showing the fourth embodiment of the present invention;

FIG. 20 is a block diagram showing a modified fourth embodiment of the present invention;

FIG. 21 diagrammatically shows the fifth embodiment of the present invention;

FIG. 22 is a perspective view showing a polarization controller;

FIG. 23 shows part of an OCT device control panel;

FIGS. 24A, 24B and 24C diagrammatically show a test tool;

FIG. 25 diagrammatically shows a stage in the first embodiment of the present invention;

FIG. 26A shows an image obtained by the first embodiment of the present invention, FIG. 26B shows an image obtained by the modified first embodiment of the present invention, and FIG. 26C shows an image with a scale for distance measurements.

Figure 14A:
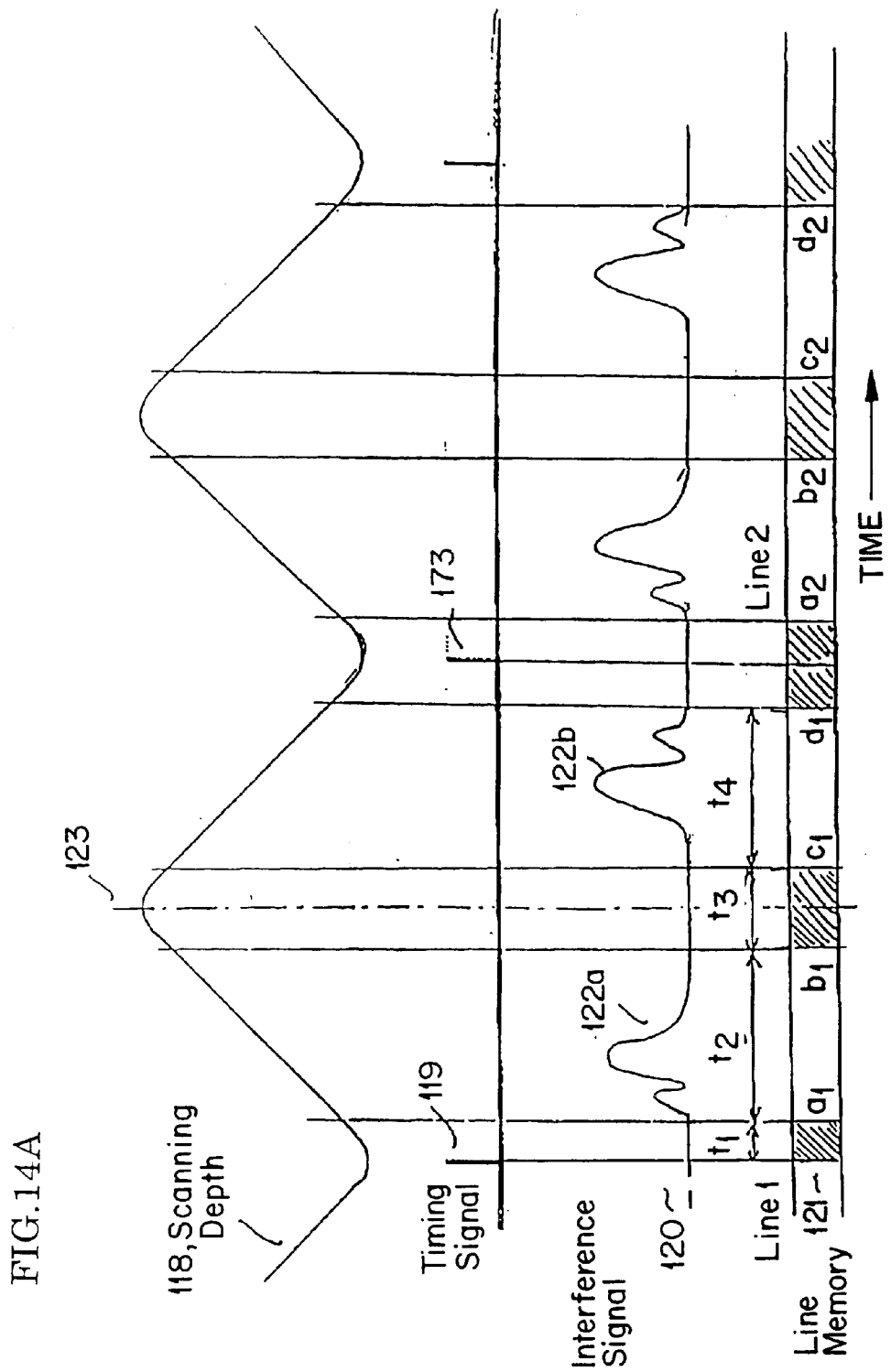
FIG. 14A is a time chart showing the relationship between a depth direction scanning position curve, mirror scanning timing signal and interference signal in the third embodiment of the present invention.
Figure 14B:
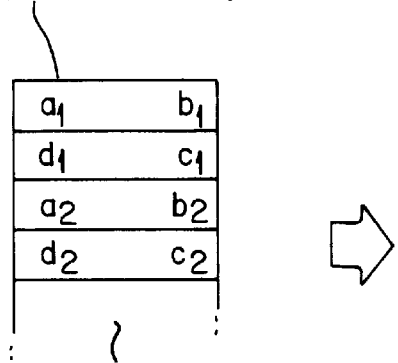
FIG. 14B is a memory map.
Figure 27:
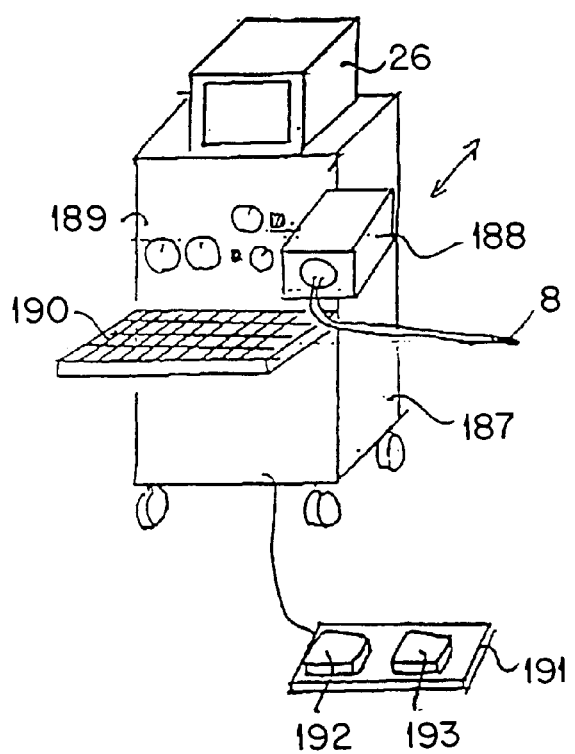
Figure 28:
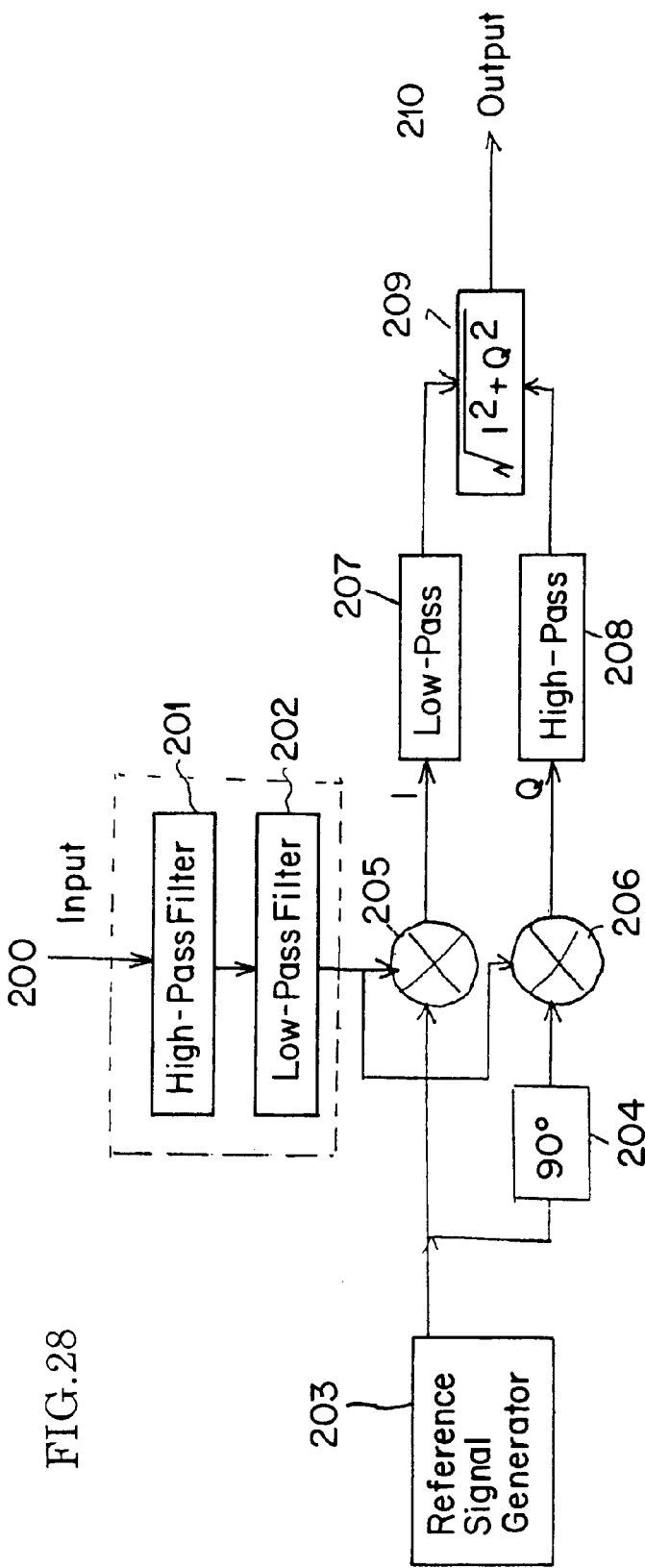

FIG. 27 is a perspective view showing the first embodiment;

FIG. 28 shows a circuit for a coherent tracking demodulator;

FIG. 29 shows a transmissive delay line;

FIG. 30 is a mapping array instead of FIG. 14B.

Figure 32:
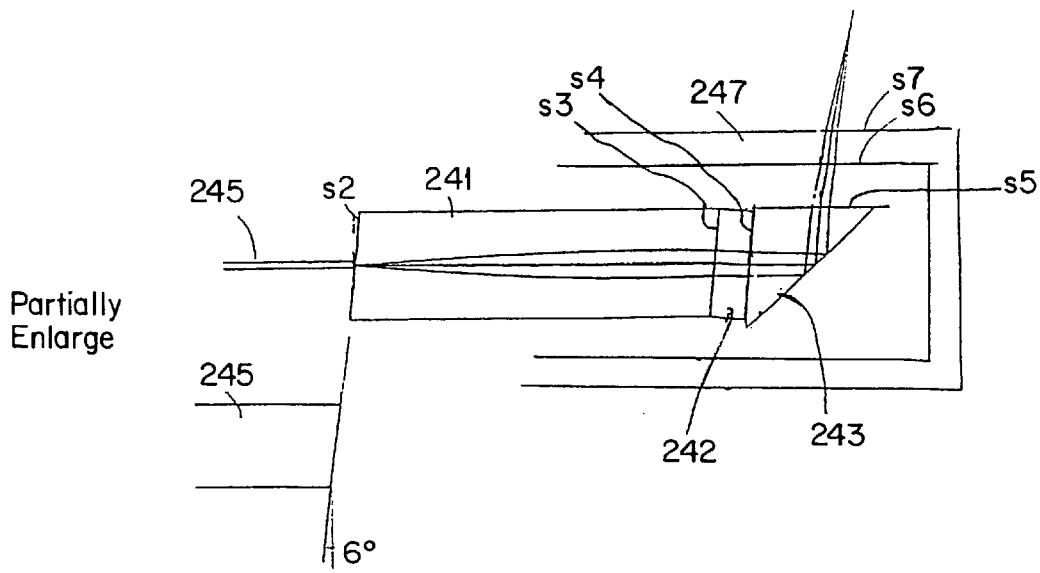
Figure 33:
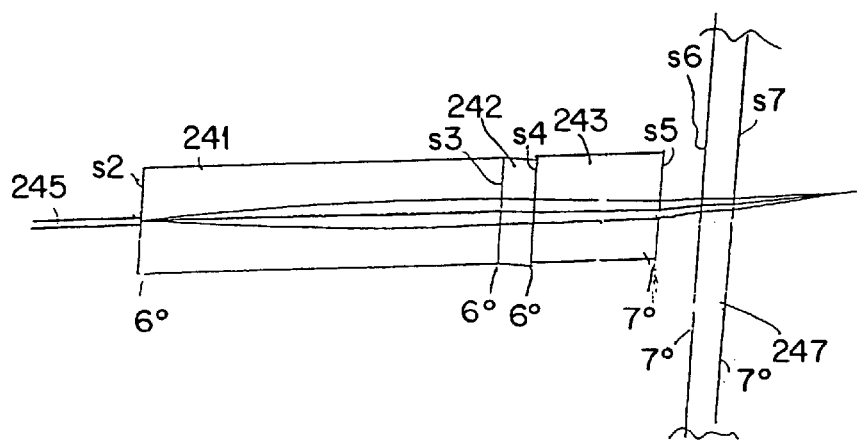
Figure 37:
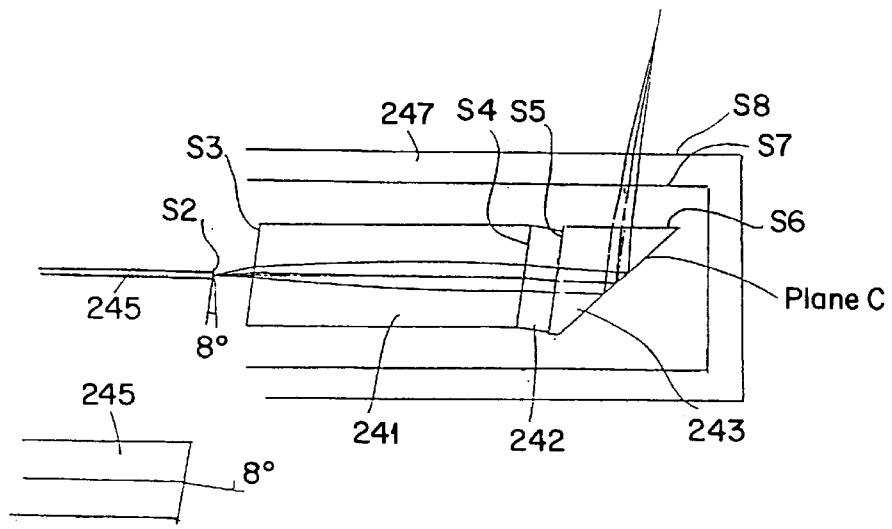
Figure 38:
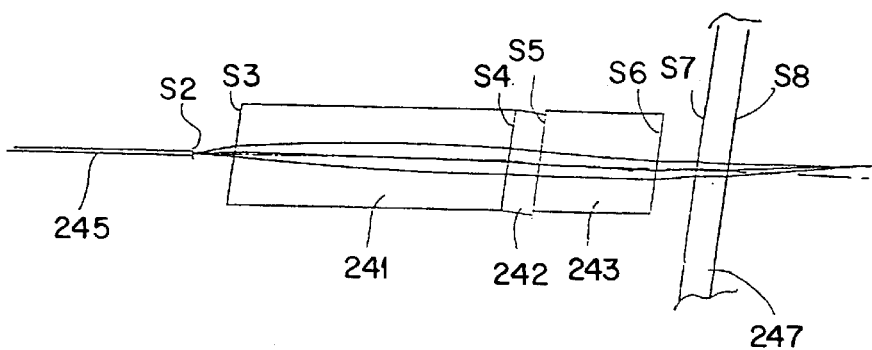
Figure 39A:
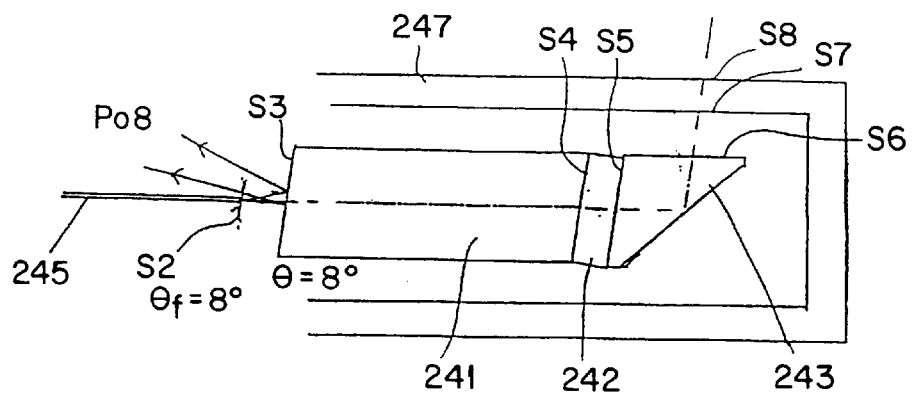
Figure 39B:
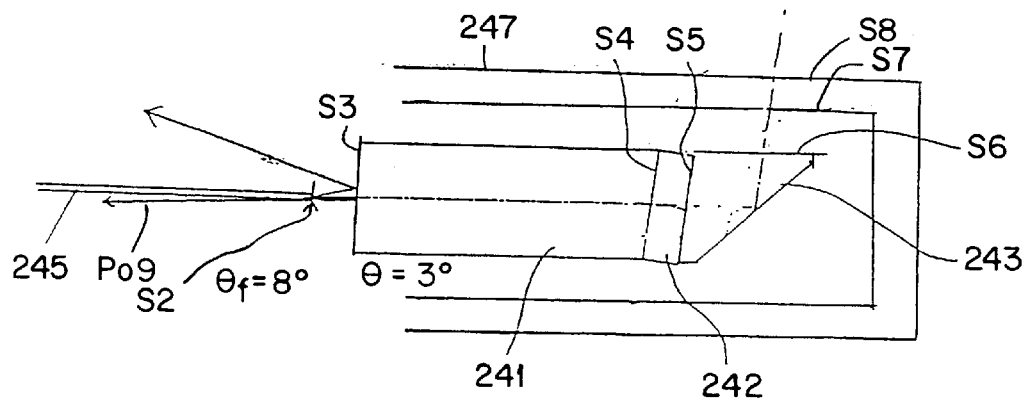
Figure 40:
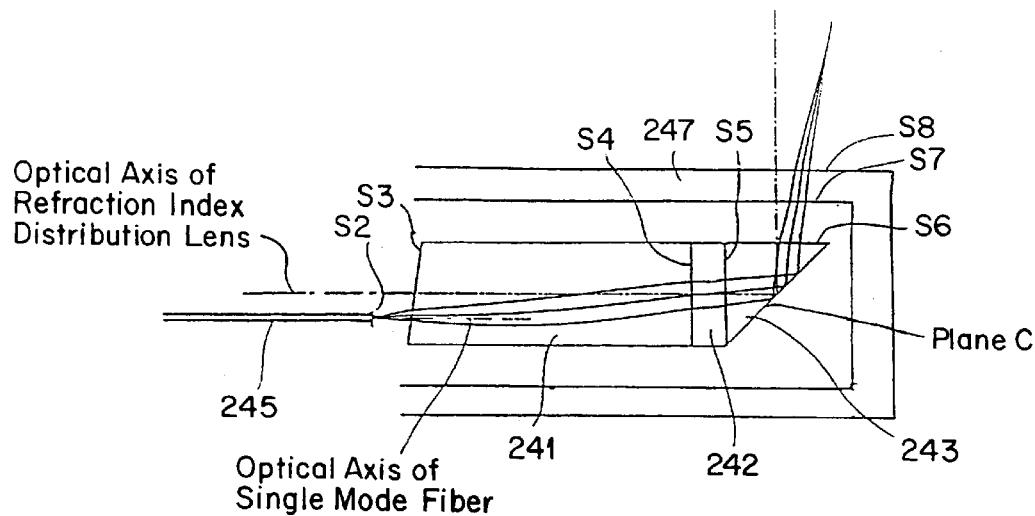
Figure 41:
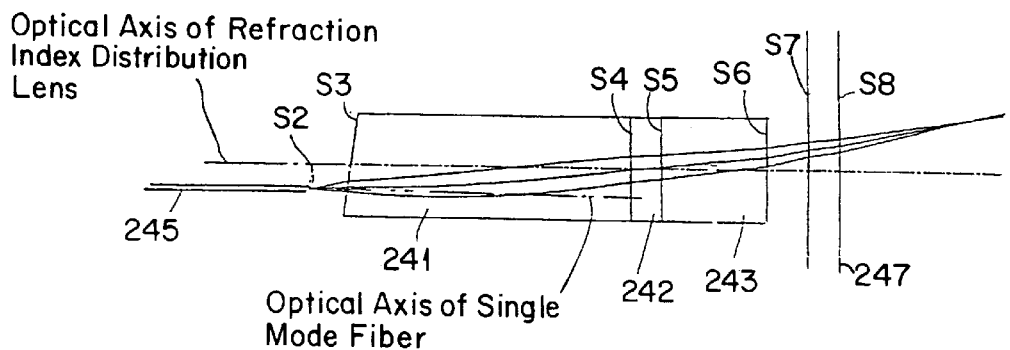
Figure 42:
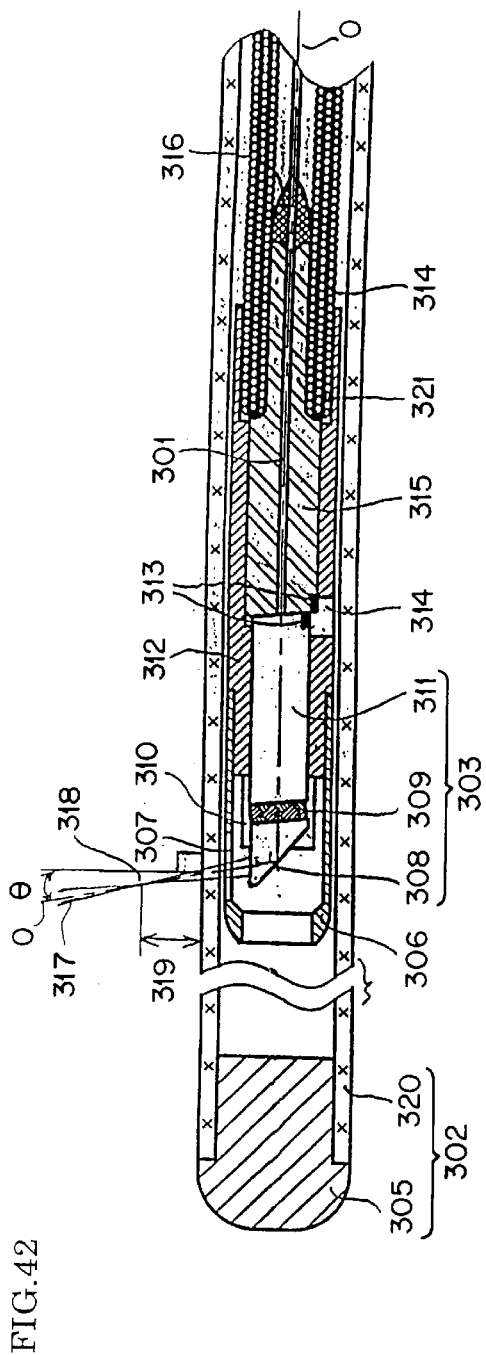
Figure 43B:
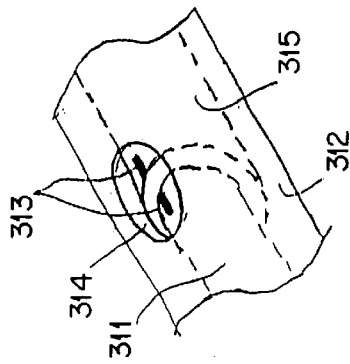
Figure 43A:
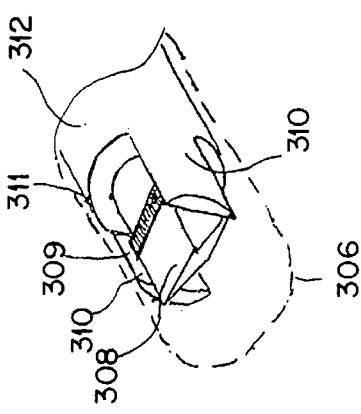
Figure 44:
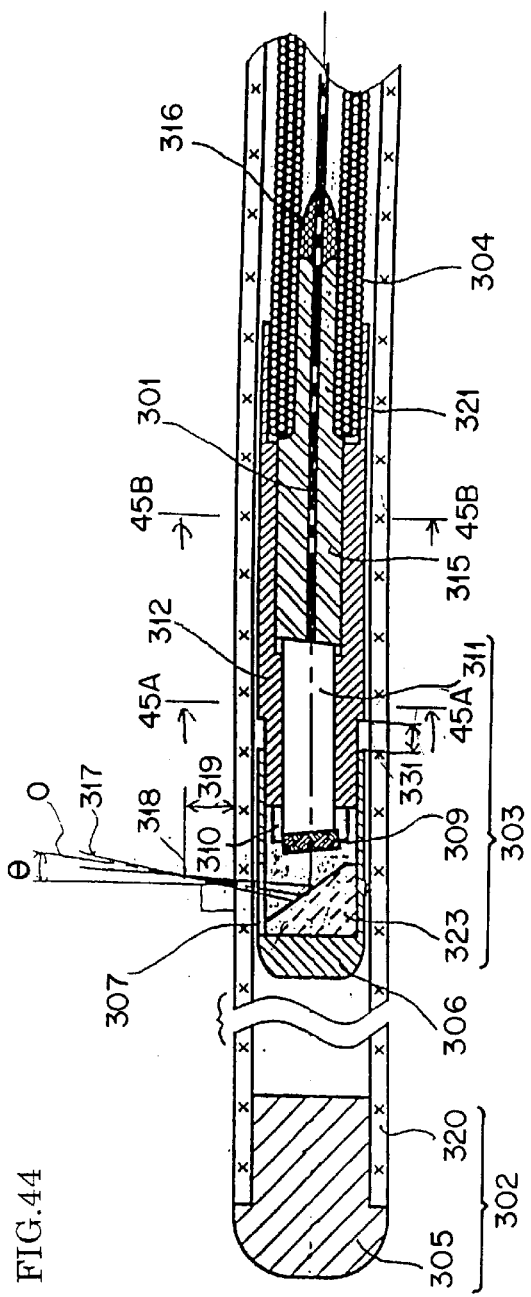
Figure 45B:
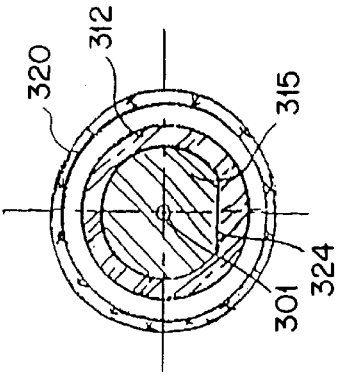
Figure 45A:
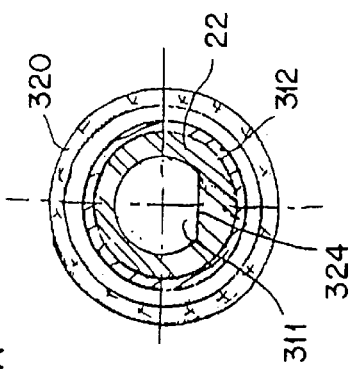
Figure 51A:
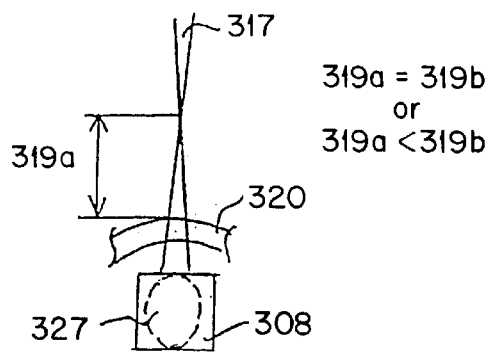
Figure 51B:
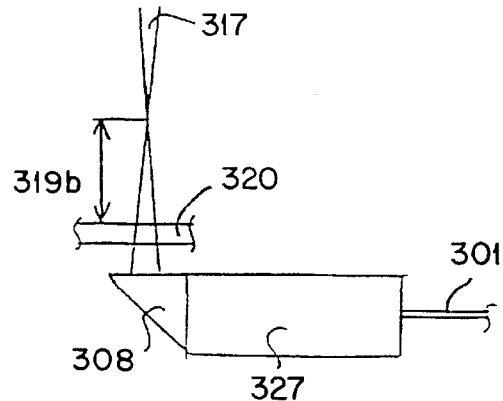
Figure 52A:
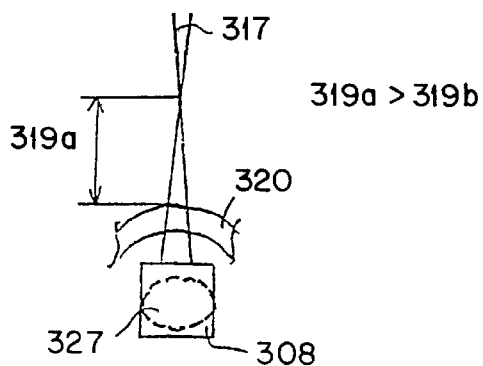
Figure 52B:
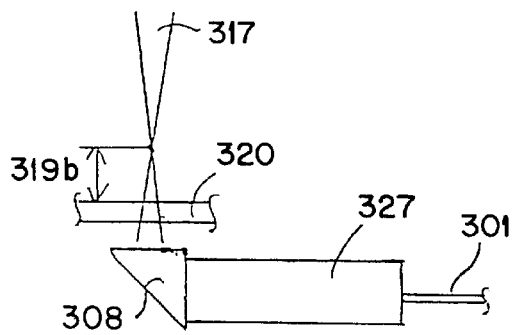
Figure 55A:
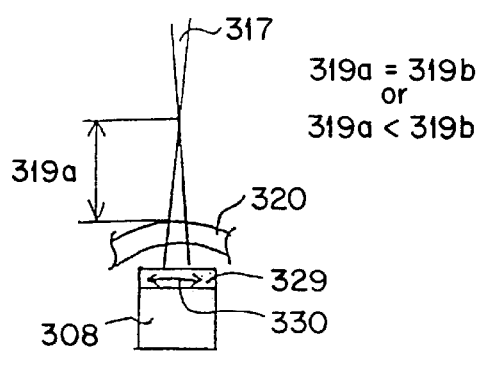
Figure 55B:
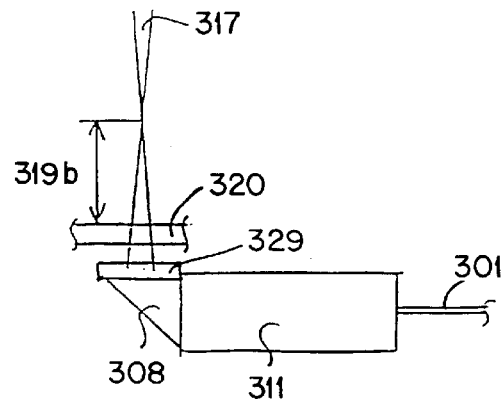
Figure 56A:
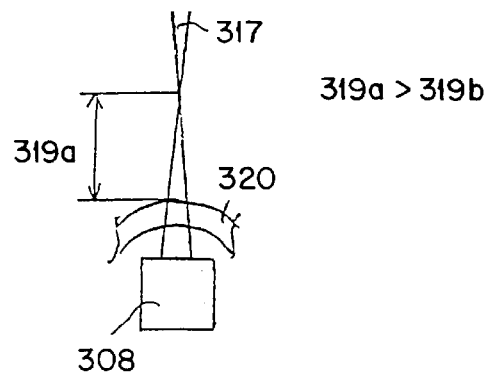
Figure 56B:
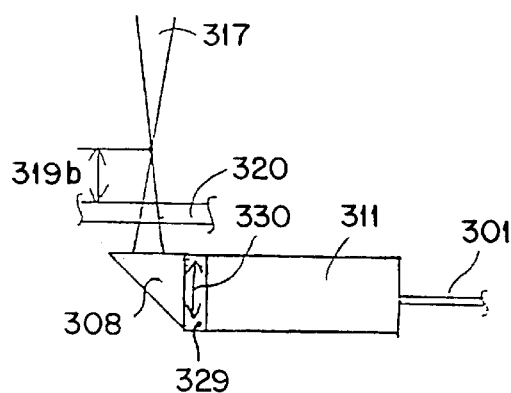

FIG. 31 diagrammatically shows an optical system of an optical tomography diagnosis device;

FIG. 32 diagrammatically shows the seventh embodiment;

FIG. 33 is a linearly redraw of FIG. 32;

FIGS. 34A, 34B, 34C, 34D, 35A, 35B, 35C, 35D, 36A, 36B, 36C and 36D are diagrammatic views showing an optical path;

FIG. 37 diagrammatically shows the eighth embodiment;

FIG. 38 is a linearly redraw of FIG. 37 embodiment;

FIGS. 39A and 39B diagrammatically show an optical path;

FIG. 40 diagrammatically shows the ninth embodiment;

FIG. 41 is a linearly redraw of FIG. 40;

FIG. 42 is a cross-sectional view showing an end of an optical scanning probe of the tenth embodiment;

FIGS. 43A and 43B are perspective views of the end of the optical scanning probe of FIG. 42;

FIG. 44 shows of an optical scanning probe of the eleventh embodiment;

FIGS. 45A and 45B are cross-sectional views taken along the lines 45A—45A and 45B—45B in FIG. 44;

FIG. 46A is a schematic view of an optical scanning probe from the side of the end, and FIG. 46B is a schematic view of the side surface of the end part of the optical scanning probe of the twelfth embodiment;

FIG. 47A is a schematic view of an optical scanning probe from the side of the end, and FIG. 47B is a schematic view of the side surface of the end part of the optical scanning probe of a modification of the twelfth embodiment;

FIG. 48A is a schematic view of an optical scanning probe from the side of the end, and FIG. 48B is a schematic view of the side surface of the end part of the optical scanning probe of another modification of the twelfth embodiment;

FIG. 49A is a schematic view of an optical scanning probe from the side of the end, and FIG. 49B is a schematic view of the side surface of the end part of the optical scanning probe of the thirteenth embodiment;

FIG. 50A is a schematic view of an optical scanning probe from the side of the end, and FIG. 50B is a schematic view of the side surface of the end part of the optical scanning probe of a modification of the thirteenth embodiment;

FIG. 51A is a schematic view of an optical scanning probe from the side of the end, and FIG. 51B is a schematic view of the side surface of the end part of the optical scanning probe of the fourteenth embodiment;

FIG. 52A is a schematic view of an optical scanning probe from the side of the end, and FIG. 52B is a schematic view of the side surface of the end part of the optical scanning probe of a modification of the fourteenth embodiment;

FIG. 53A is a schematic view of an optical scanning probe from the side of the end, and FIG. 53B is a schematic view of the side surface of the end part of the optical scanning probe of the fifteenth embodiment;

FIG. 54A is a schematic view of an optical scanning probe from the side of the end, and FIG. 54B is a schematic view of the side surface of the end part of the optical scanning probe of a modification of the fifteenth embodiment;

FIG. 55A is a schematic view of an optical scanning probe from the side of the end, and FIG. 55B is a schematic view of the side surface of the end part of the optical scanning probe of the sixteenth embodiment;

FIG. 56A is a schematic view of an optical scanning probe from the side of the end, and FIG. 56B is a schematic view of the side surface of the end part of the optical scanning probe of a modification of the sixteenth embodiment;

FIG. 57A is a schematic view of an optical scanning probe from the side of the end, and FIG. 57B is a schematic view of the side surface of the end part of the optical scanning probe of the related art.

DETAILED DESCRIPTION OF PREFERRED EMBODIMENT

First Embodiment

The first embodiment is able to compensate for the stress-induced birefringence of the fiber bent and varied in quality so that it may be introduced into the patient's body cavity, and to compensate for the stress-induced birefringence of the fiber varied in quality, depending on the rotation of radial scanning in the patient's body cavity.

FIG. 6 shows a composition of an optical imaging device in the first embodiment of the present invention. FIG. 7 shows an endoscope through which the first embodiment is passed.

Optical imaging device 1A (optical tomography imaging device), shown in FIG. 6, includes superluminescent diode (SLD) or a semiconductor optical amplifier (SOA) based low coherence light source 2 that emits amplified spontaneous emission (ASE). This low coherence light source 2 has a central wavelength of 1300 nm and an optical bandwidth of 50–70 nm, for example. It produces low coherence light that causes interference only when the optical path lengths of the interferometer are matched to within a short distance range, at an interfering distance of 17 microns, for example. In other words, this light may be divided into two rays, for example, and then mixed. In such cases, interfering light is detected if the difference between two optical lengths, from branch to junction, is within the short distance range of 17 microns or so; otherwise this light does not interfere.

Light is emitted from low coherence light source 2, and incident on an end of the first single mode fiber 3, and then sent to the other end surface (distal end surface). First single mode fiber 3 leads to an optical coupler 4 and is optically connected by the optical coupler, to a second single mode fiber 5. Thus, light is divided by optical coupler 4, into two paths for transmission. On the distal side (distal of optical coupler 4) of first single mode fiber 3, optical rotary joint 6 is interposed which couples a non-rotary part with a rotary part so that light can be sent to the probe. Connector 9 of optical scanning probe 8 is detachably connected to the distal end of a third single mode fiber 7 in optical rotary joint 6, and passed through optical scanning probe 8. Light is emitted from low coherence light source 2, and sent (guided) to fourth single mode fiber 10 which is rotated.

The subject, biological tissue 11, is scanned and irradiated with the light sent from the distal end of optical scanning probe 8. Light is scattered on the surface or inside of biological tissue 11, and part of the reflection is collected which returns, through the reverse optical path, to first single mode fiber 3. Part of the returning light is sent by optical coupler 4, to the second single mode fiber 5. From the end of second single mode fiber 5, light is sent and incident on photodiode 12, for example, used as an optical detector. It should be noted that the rotor of optical rotary joint 6 is driven by rotary drive 13, to rotation.

On the side distal of optical coupler 4 on second single mode fiber 5, variable-optical length mechanism 14 is provided which varies the optical length of reference beam. Variable-optical length mechanism 14 includes, as explained below: a first optical length-varying means for quickly varying optical length only within a predetermined scanning range, depending on the optical length in which biological tissue 11 is scanned by optical scanning probe 8, in the depth direction only within the predetermined scanning range; a second optical length-varying means capable of varying optical length to compensate for the statistical variation of the optical scanning probe length so as to cancel the possible variations of each optical scanning probe length after optical scanning probe 8 is replaced with a new one; and a dispersion-varying means capable of varying dispersion to compensate for dispersion mismatch between the sample and reference arms of the interferometer.

Grating 16 is optically coupled, through facing collimator lens 15, to the distal end of second single mode fiber 5. To grating 16, and through facing lens 17, angular scanning mirror 19 is optically coupled which can rotate by a slight angle and is used as the first optical length-varying means. Mirror 19 is pivotally vibrated by galvanometer controller 20, quickly, as denoted by code b.

Galvanometer mirror 19 reflects light. When applied to the galvanometer mirror, an AC drive signal pivotally vibrates the mirror in the movable part.

In other words, the drive signal is applied by galvanometer controller 20 to the galvanometer mirror so that optical scanning probe 8 can scan biological tissue 11 in the depth direction only within the predetermined distance range at high speed. As denoted by code b, this drive signal pivotally vibrates the mirror quickly.

The optical length of light, which is sent from the end surface of second single mode fiber 5, which is reflected by galvanometer mirror 19, and which returns, is varied by such pivotal vibrations, only within the predetermined scanning range of distance.

In other words, galvanometer mirror 19 defines a first optical length-varying means used to obtain a tomogram in the depth direction. "In vivo video rate optical coherence tomography" (A. M. Rollins et al. supra) discloses this optical length-varying means based on galvanometer mirror 19.

The optical length-varying means disclosed in the reference is cited is actually a propagation group delay varying means. Despite the slight actual variation in optical length, variations in interference location, due to the group delay of low coherence light, are vast. The phrase "variations in optical length" used herein includes variations in interference location, due to the group delay. Another important advantage of this delay line is that it allows for compensation for uneven amounts of second-order optical dispersion in the two interferometer arms. This is important in the current embodiment because although the optical path lengths of the sample and reference arms are necessarily equal, the sample arm contains more of its path length in optical fiber than the reference arm does. If there were no compensation for the resulting difference in dispersion between the two arms, then the interference length (and hence the axial imaging resolution) would be greatly extended. As disclosed in the reference, dispersion compensation is accomplished by a slight adjustment in the distance between the grating 16 and the lens 17 in the delay line.

Second first single mode fiber 5 and collimator lens 15 are provided on uniaxial stage 18 that can move in the optical axis, as denoted by code a. They are used as a second optical length-varying means.

On or before the second optical length-varying means, polarization adjusting fiber loop 29 is provided which removes the effects of the birefringence caused by bending both an entire interference system including the fiber, and a fiber in the optical scanning probe.

On the other hand, uniaxial stage 18 defines second optical length-varying means which has a sufficient variable-optical length range to compensate for the statistical variation in the optical length of optical scanning probe 8, after optical scanning probe 8 is replaced with a new one. Galvanometer mirror 19 may be used to vary optical length, in order to produce an image in the depth direction. In such cases, uniaxial stage 18 has the capability of an offset adjustment means for adjusting offset so that it can produce an image from a desired position (for example, the surface by the use of uniaxial stage 18 to vary optical length, in order to set the status so that interference may occur from the surface of biological tissue 11, even if the optical scanning probe tip does not reach biological tissue 11).

Uniaxial stage 18 includes a motor for moving the stage. The use of position controller 21 to apply a drive signal to the motor causes uniaxial stage 18 to move in the direction denoted by code a.

FIG. 25 shows a composition of the stage. On slider 179, stage 178 is placed which enables precision sliding while the optical axis is kept lateral. Ball screw 180 is provided on slider 179. Stepping motor 181 is provided at the proximal end of the ball screw. As stepping motor 181 turns ball screw 180, stage 178 moves. Lens 15 and the end of second single mode fiber 5 are provided on stage 178. Collimator 182 is set so that it may provide parallel rays for grating 16.

Light returning from the variable-optical length mechanism 14 in FIG. 6 is guided by optical coupler 4 provided on second single mode fiber 5, and mixed with light returning from the optical scanning probe 8. Both rays are received by photodiode 12. It should be noted that with uniaxial stage 18 set approximately in the middle of the variable range, the length of second single mode fiber 5 is set so that the optical length from optical coupler 4, through fourth single mode fiber 10, and through the optical scanning probe tip, to biological tissue 11 may be approximately equal to the optical length of light which is sent through second single mode fiber 5, and reflected by galvanometer mirror 19 on uniaxial stage 18.

The statistical variation of the length of manufactured optical probes is compensated by changing the position of uniaxial stage 18, according to the optical scanning probe 8 actually connected and used. Galvanometer mirror 19 is pivotally vibrated quickly, to produce periodical fluctuations in optical length on the reference beam side so that the reference beam can interfere with reflection at the biological tissue depth where both optical lengths are equal to each other, and so that at other depths, reflection cannot interfere with the reference beam.

A signal is produced by photoelectric conversion of photodiode 12, amplified by amplifier 22, and input to demodulator 23. Demodulator 23 performs demodulation that extracts only interfering light signal components. The demodulated output is converted by analog-to-digital converter 24, and input to computer 25. Computer 25 produces image data that corresponds to the tomogram. The image data is output to monitor 26; thus, an OCT image 27 is displayed on the screen. Computer 25 is connected to position controller 21. Computer 25 uses position controller 21 to control the position of uniaxial stage 18. Computer 25 is connected to video synchronizing circuit 28. In phase with the video synchronizing signal during imaging, the computer stores tomogram data in the internal memory.

Video synchronizing signals are sent from video synchronizing circuit 28, to galvanometer controller 20, and to rotary drive 13 respectively. Galvanometer controller 20, for example, outputs drive signals in cycles that synchronize with video synchronizing signals (more precisely, high-speed first video synchronizing signals) and the video synchronizing signals are classified into two types: high-speed and low-speed video synchronizing signals. In cycles that synchronize with video synchronizing signals (more precisely, second low-speed video synchronizing signals), rotary drive 13 outputs drive signals that synchronize with the first video synchronizing signals. Rotary drive 13 turns the scanning light, in order to scan the circumference with light.

In the first embodiment, as shown in FIG. 7 for example, optical scanning probe 8 is passed through forceps port 32 of endoscope 31, and through the forceps channel so that the optical scanning probe tip can project from the distal end opening.

Endoscope 31 has an elongated insertion unit 33 that can be introduced into the patient's body cavity. Thick control unit 34 is provided at the rear end of insertion unit 33. Forceps port 32 is provided close to the rear end of insertion unit 33. Forceps port 32 internally communicates with the forceps channel.

A light guide (not shown) is passed through insertion unit 33. The input end of this light guide is connected to a light source. Light is sent, through light guide, to the lighting port provided in the distal end part of insertion unit 33. The diseased part is irradiated with light from the lighting port. An observation port is provided adjacent to the lighting port. An objective optical system is mounted on this observation port so that the doctor can observe the irradiated diseased part or the like, with the optical system. While observing with the observation optical system in the distal end part of insertion unit 33, the doctor irradiates biological tissue 11 in the diseased part and other targets, with low coherence light, using optical scanning probe 8, to produce tomogram data of biological tissue 11. OCT image 27 can thus be displayed on the screen of monitor 26.

Curve 35 and tip part 36 in FIG. 7 are provided in the distal end part of insertion unit 3. On occasions when optical scanning probe 8 is passed through curve 35, and when the doctor makes the optical scanning probe tip 37 project from endoscope tip part 36 so that the optical scanning probe tip may touch biological tissue 11 as in FIG. 7A, optical scanning probe tip 37 is bent with a small radius of curvature.

Figure 1:
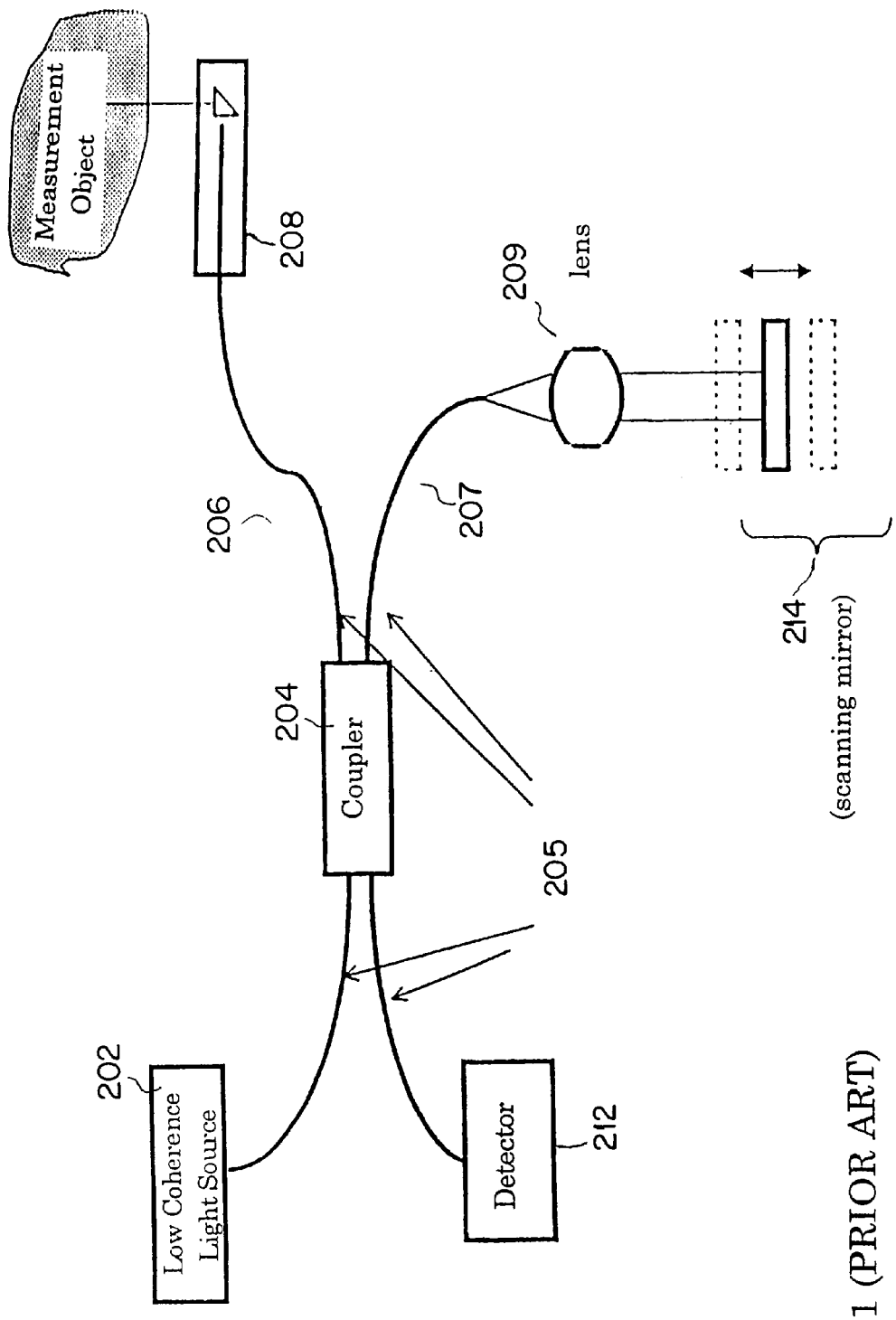
FIG. 1 diagrammatically shows an OCT applied to an endoscope (prior art)
Figure 2:
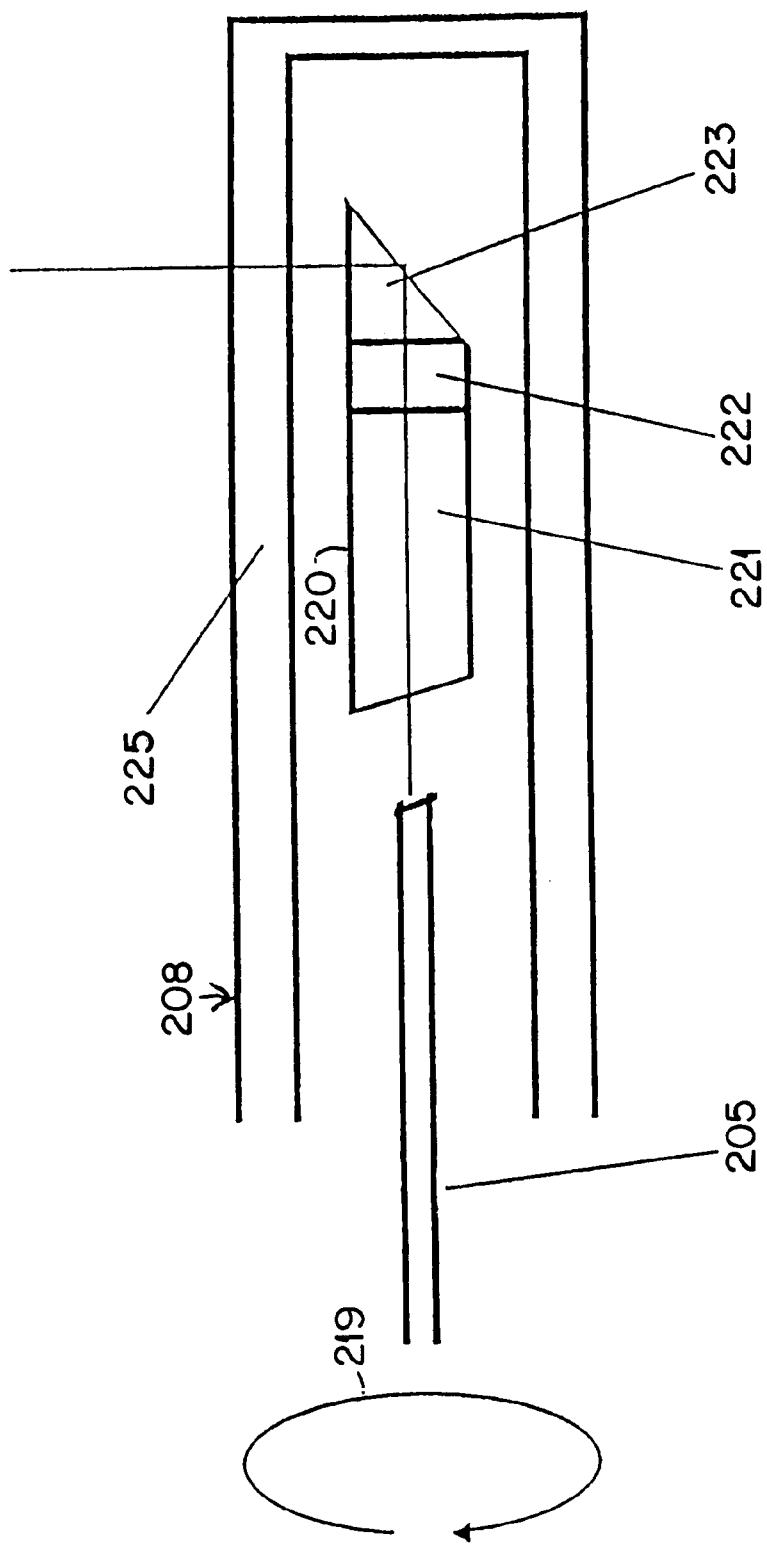
FIG. 2 is a diagrammatic view showing non-prior art (related art) details of a part of FIG. 1.
Figure 3A:
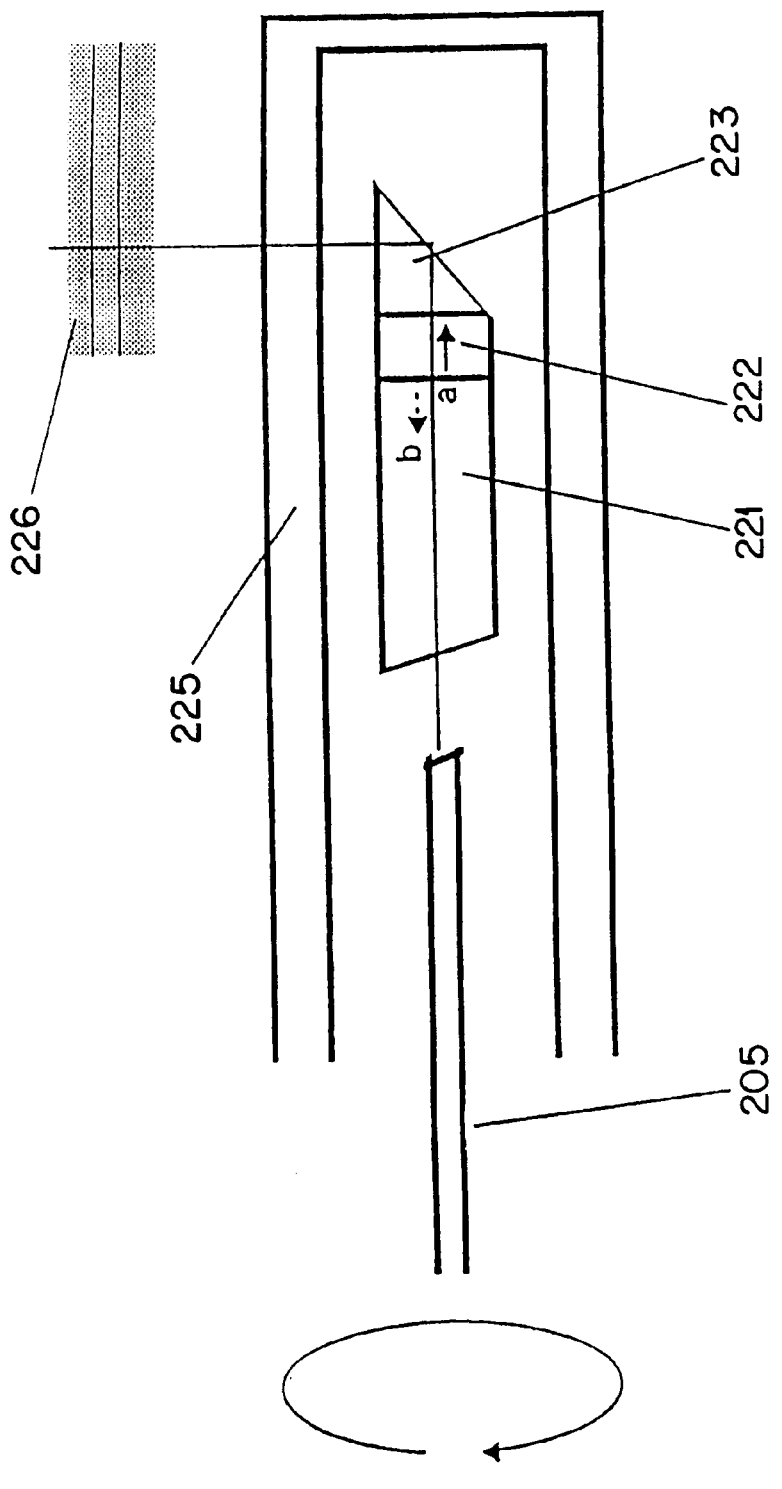
FIGS. 3A–3E are diagrammatic views showing an example of causes for generating ghosts.
Figure 3B:
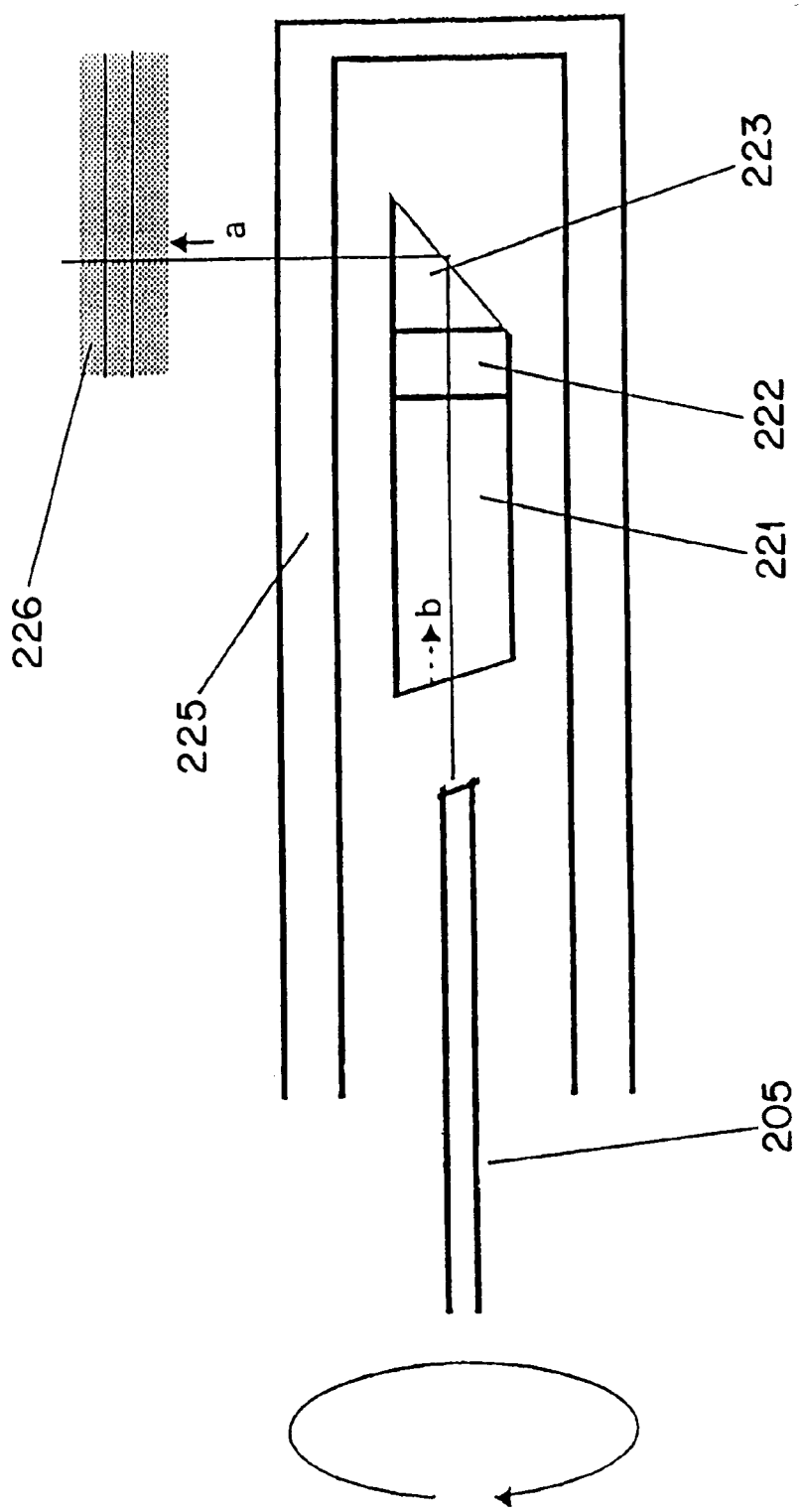
Figure 3C:
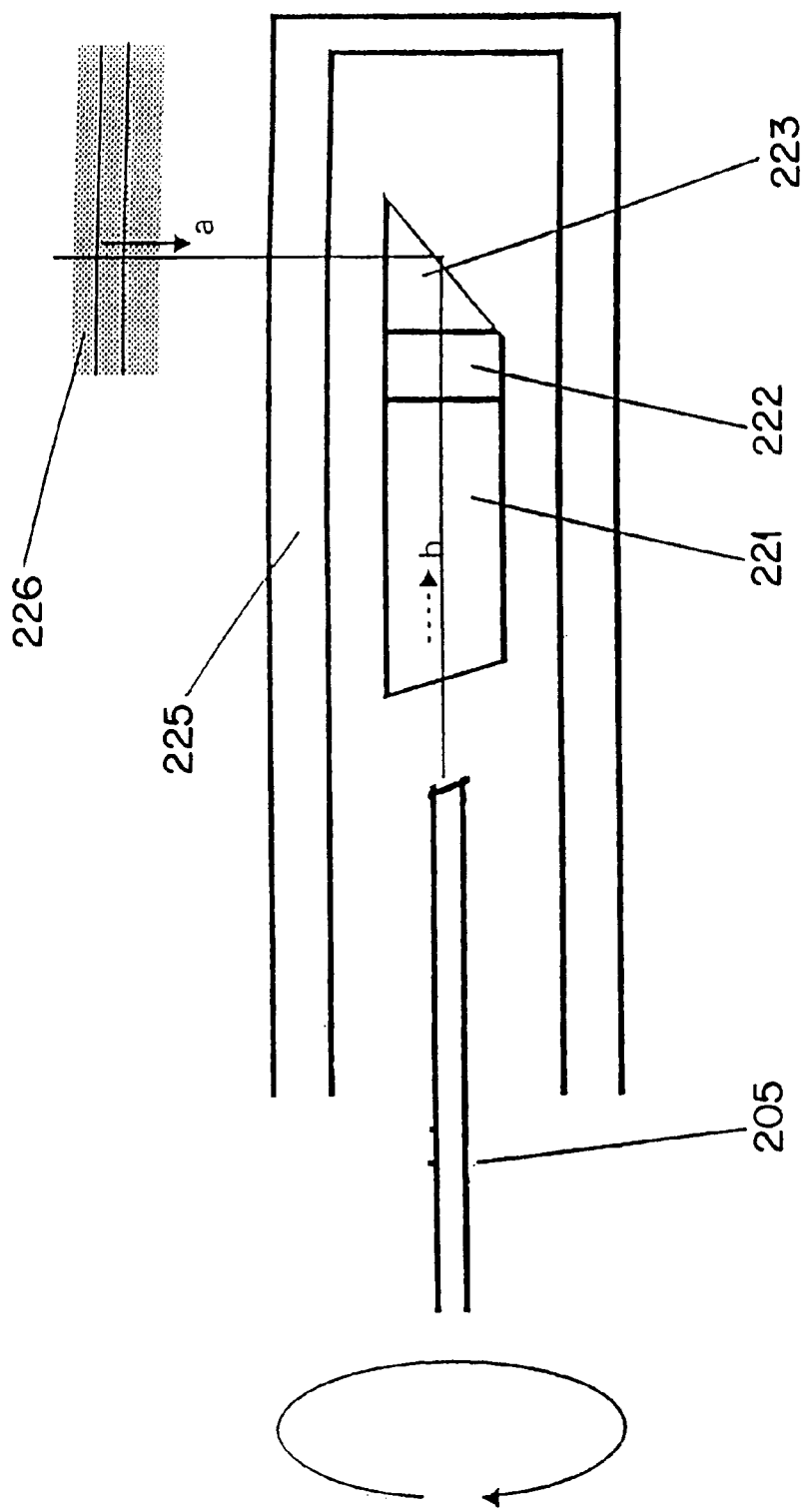
Figure 3D:
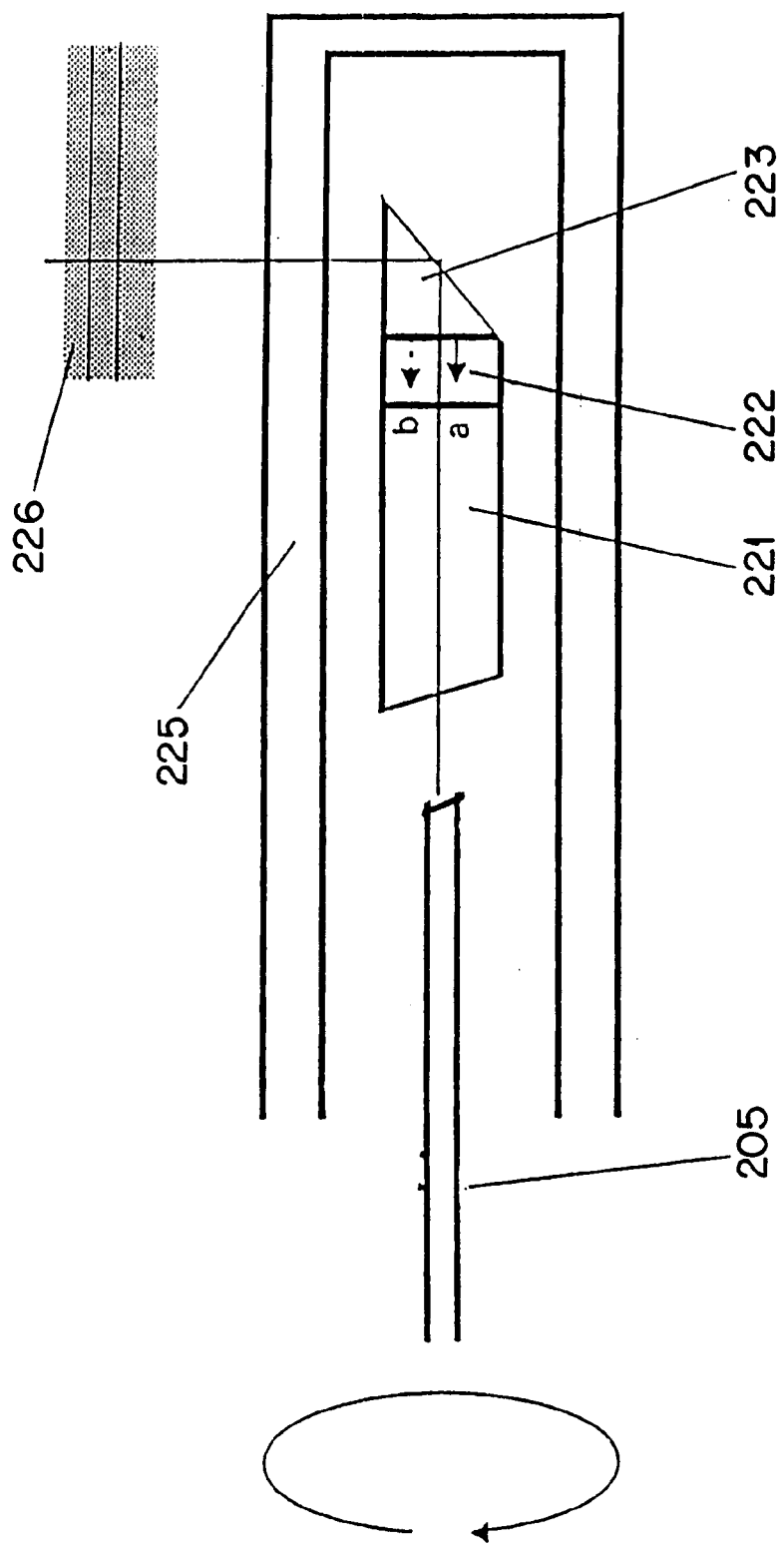
Figure 3E:
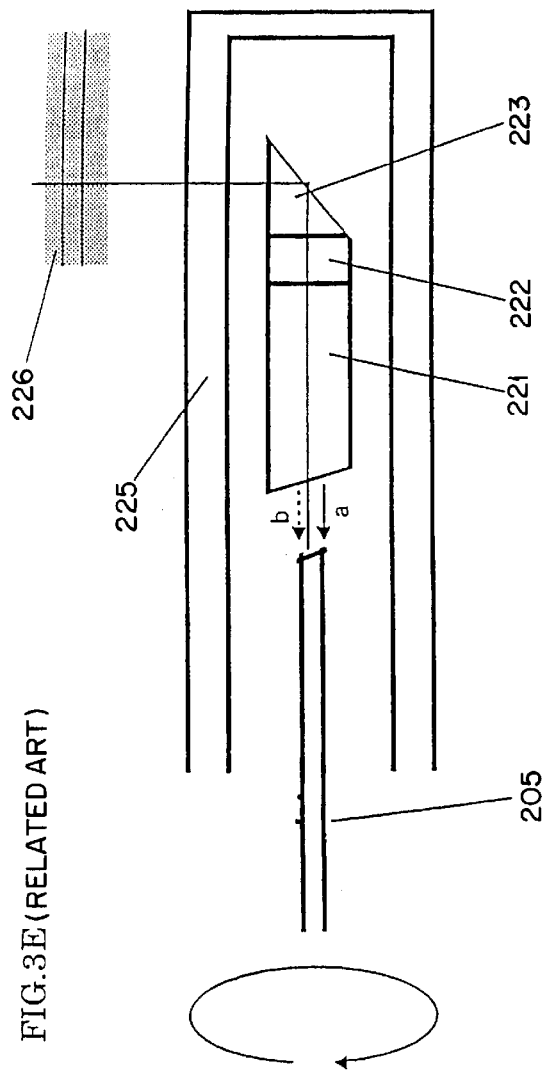
Figure 4:
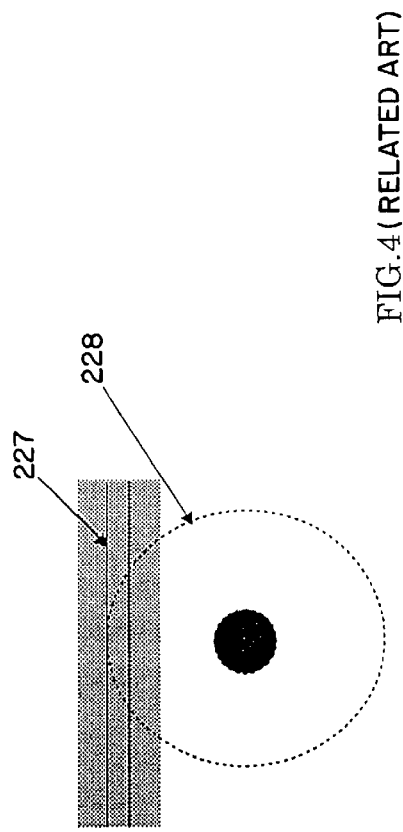
FIG. 4 shows a ghost image.
Figure 5A:
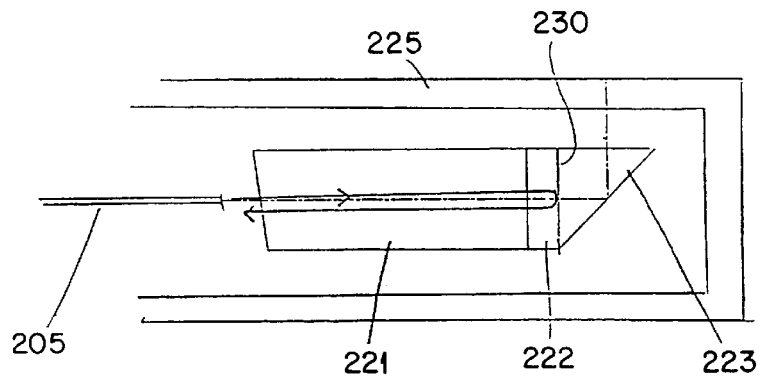
FIGS. 5A and 5B diagrammatically show an example of a related art structure of once reflection when light is reflected on the boundary surface between a Faraday rotator and prism.
Figure 5B:
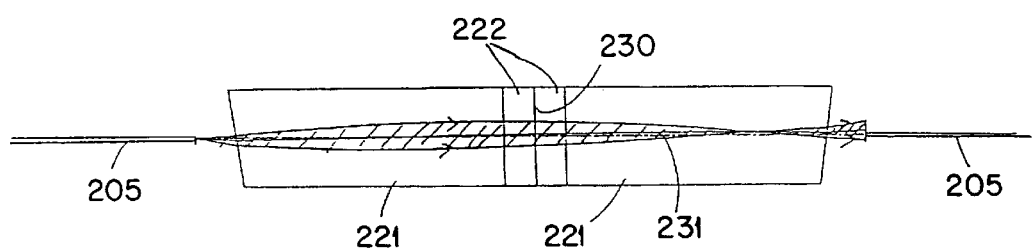
Figure 8:
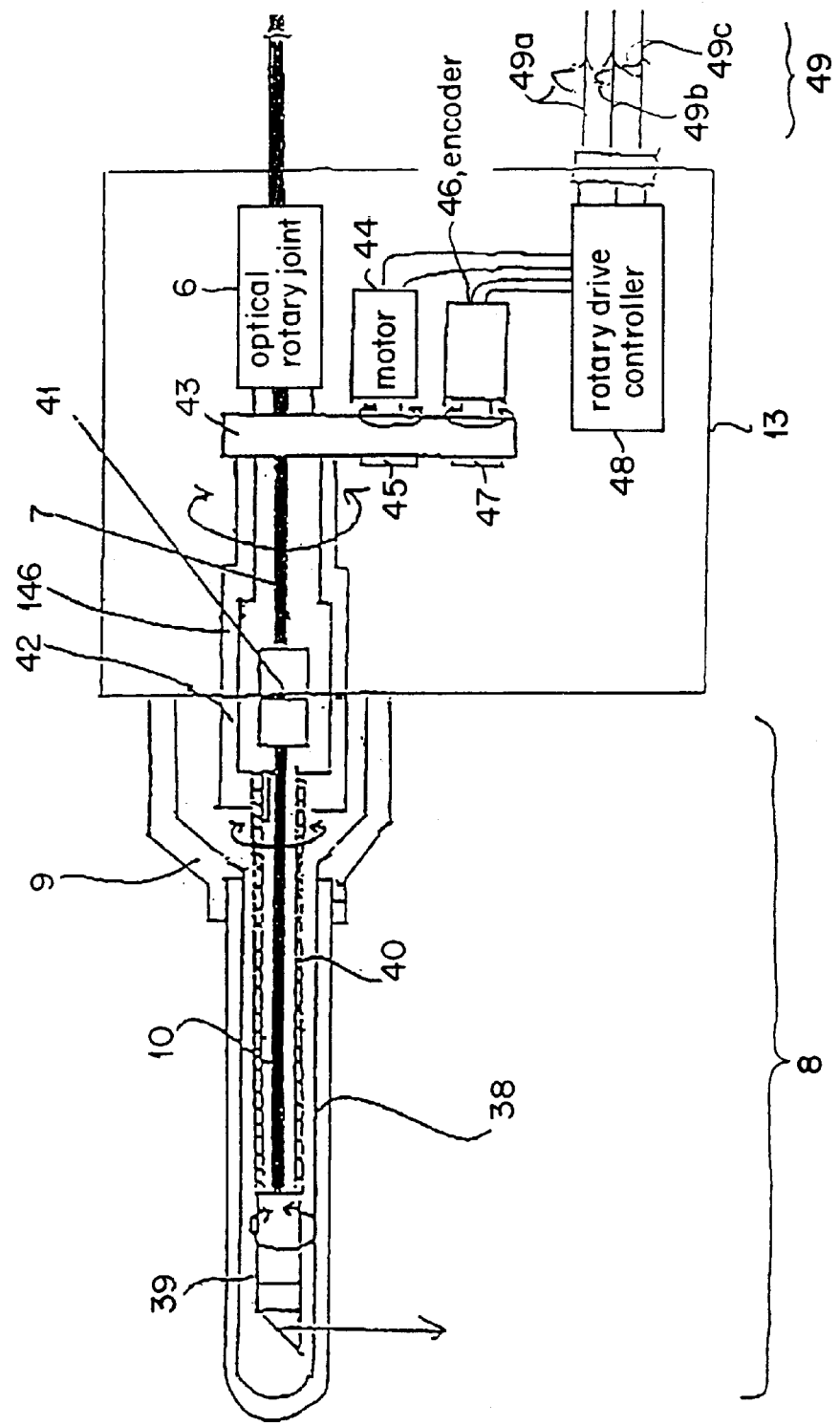
FIG. 8 diagrammatically shows an optical scanning probe and a rotary drive in the first embodiment of the present invention.

FIG. 8 diagrammatically shows a combined optical scanning probe 8 and rotary drive 13. Optical scanning probe 8: an optical sheath 38 that includes an elongated resin tube; a connector 9 connecting sheath 38 to rotary drive 13; a flexible shaft 40 provided inside optical sheath 38 so that it can rotate; a fourth single mode fiber 10 provided in a lumen of the flexible shaft; a lens unit 39 connected to the distal end of flexible shaft 40; a rotation transmission connector 42 connected to flexible shaft 40; and an optical connector 41 connected to the other end of fourth single mode fiber 10.

Rotary drive 13 has a rotary shaft 146 and an optical rotary joint 6 connected to the rotary shaft. Optical connector 41 is provided in the other end part of rotary shaft 146. Optical rotary joint 6 is connected by third single mode fiber 7, to optical connector 41. Rotary drive 13 has a motor 44, a motor pulley 45, an encoder 46, and an encoder pulley 47. Motor 44 and encoder 46 are connected to rotary drive controller 48.

The action of rotary drive 13 is described below. The torque of motor 44 is transmitted to motor pulley 45, and further transmitted by belt 43, to rotary shaft 146, and to encoder pulley 47. Encoder 46 detects the rotating speed of rotary shaft 146. Drive current for motor 44 is controlled by rotary drive controller 48 so that the rotating speed may be a predetermined speed. Rotary shaft 146 thus rotates steadily at the predetermined speed. The rotation angle is detected by encoder 46, and sent, through rotary drive controller 48, to a circuit for signal 49.

Signal 49 includes: a phase-A pulse 49a, one of 256 divisions produced when one cycle is divided by 256; a phase-B pulse 49b which is out of phase by 45 to the phase-A pulse; and a pulse 49c per cycle.

Action of optical scanning probe 8 is described below. Light is sent by optical connector 41, through third single mode fiber 7, to fourth single mode fiber 10. The torque of rotary shaft 146 is transmitted by rotation transmission connector 42 to flexible shaft 40. Light is sent, through fourth single mode fiber 10, to lens unit 39 and passed through optical sheath 38, in order to irradiate the outside with inspection light. Reflection from the biological tissue is received, and sent through fourth single mode fiber 10. Since the flexible shaft tip is connected to lens unit 39, an integrated system of flexible shaft 40, lens unit 39, and fourth single mode fiber 10 rotates.

Figure 9A:
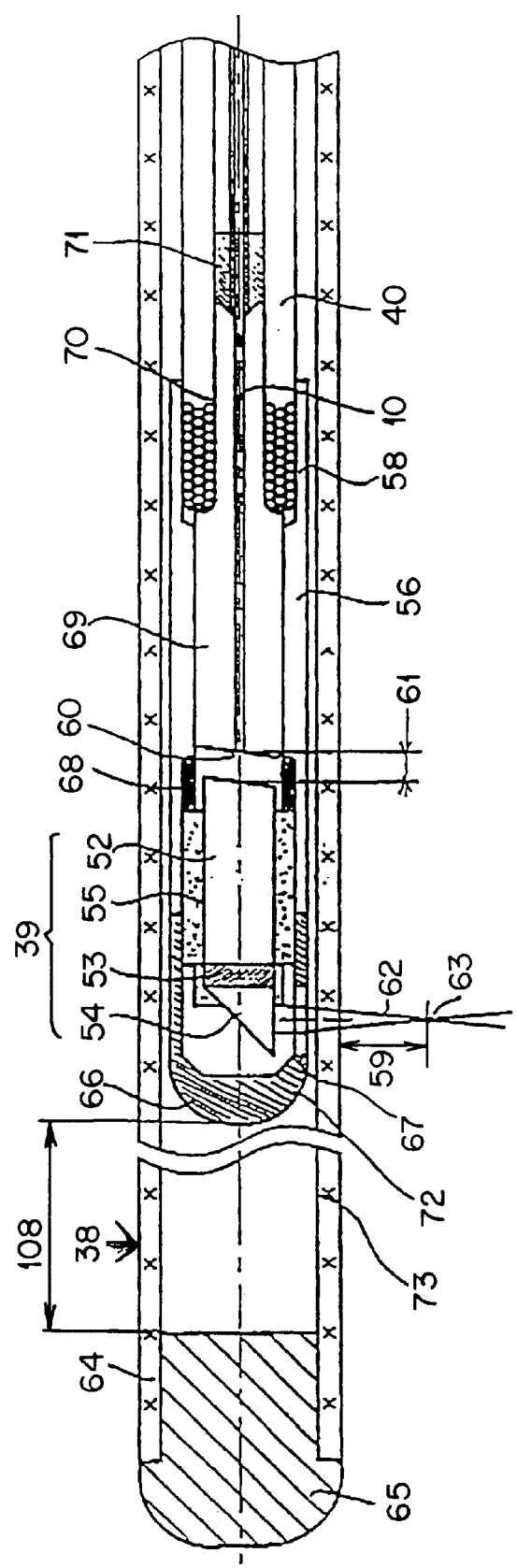
FIG. 9A shows the optical scanning probe in detail.

FIG. 9A is a detailed illustration of optical scanning probe 8. Optical sheath 38 includes a nylon tube 64 and a tip cap 65. Tip cap 65 is joined by adhesive to nylon tube 64. Lens unit 39 includes a prism 54, a Faraday rotator 53, and a GRIN lens (Gradient Index lens) 52.

Fourth single mode fiber 10 is joined by adhesive to ferrule 69. Lens unit 39, ferrule 69, and flexible shaft 40 are connected by connection member 56. Light is sent from fiber end 60, and incident on GRIN lens 52. The incident light is then transmitted through Faraday rotator 53, turned by prism 54, at right angles, and further transmitted by nylon tube 64, to produce observation beam 62. The observation beam is condensed onto focus 63. Varying interval 61 between fiber end 60 and GRIN lens 52 can change distance 59 between focus 63 and nylon tube 64. Interval tube 68 is provided for unique positioning of the focus.

Faraday rotator 53 includes a single crystal of magnetic garnet which has the capability to rotate polarization by 45 degrees. When probe 8 is introduced into the patient's body cavity, fourth single mode fiber 10 is bent by and adapted to the curvature of the endoscope. Rotation of flexible shaft 40 causes the fourth single mode fiber to rotate and vary the bending directions periodically. Because of the stress and torsion acting on the fiber, fourth single mode fiber 10 introduces birefringence. Interference contrast between light returning from optical scanning probe 8 through optical coupler 4 and reflection from variable-optical length mechanism 14 is damped if polarizations do not coincide with each other. Rotation of flexible shaft 40 causes the interference signal amplitude to oscillate periodically to produce an observation image uneven in tone. With Faraday rotator 53 provided at the distal end, whatever birefringence the single mode fiber may have, light is sent from fourth single mode fiber 10, transmitted through Faraday rotator 53, projected onto the biological tissue, reflected by the tissue, further transmitted through Faraday rotator 53, and returned to fourth single mode fiber 10, to produce a polarization that has rotated by 90 degrees to the incident polarization. The Faraday rotator has the capability to compensate for arbitrary birefringence of the fiber, because the polarization state of the light returning to the fiber coupler 4 will not vary depending on the birefringence of the fiber in the reference arm. This truth is disclosed in a reference "Polarisation-insensitive fibre optic Michelson interferometer" (Electr. Lett. Vol.27, pp518–519, 1991). A common Faraday rotator includes a garnet crystal and a magnet which provides a magnetic field for the crystal and which causes polarization to rotate by 45 degrees; whereas Faraday rotator 53 includes a single crystal of magnetic garnet which acts as a magnet. Only a crystal is needed to form Faraday rotator 53. It can be attached to the small optical scanning probe tip to be introduced into the patient's body cavity.

Touching Faraday rotator 53 to the GRIN lens causes substantially parallel rays to be incident on Faraday rotator 53. In contrast to the arrangement of Faraday rotator between fiber end 60 and GRIN lens 52, such a touching arrangement ensures that the Faraday rotator can cause polarization to rotate by 45 degrees accurately. It is possible, therefore, to compensate for the birefringence, in accordance with the theory. In contrast to air, glass can decrease Fresnel reflection on the interface, when joined to the garnet crystal, because the garnet crystal has a very high refractive index. Such an arrangement will decrease irradiation light onto the biological tissue, and observation light returning from the biological tissue less than a pair of air-to-to-garnet interfaces would. Rotation of flexible shaft 40 causes connection member 56 to rotate relative to sheath 64. There is risk of the connection member being damaged by contact with the inner side 73 of sheath 38. Since flexible shaft 40 varies the overall length depending on the inserted shape of optical scanning probe 8, observation beam 62 may cross a scratch caused by contact of sheath inner side 73 with connection member 56. In such cases, the doctor may fail to observe the biological tissue. Rounded cap 66, however, is connected to lens frame 55 of lens unit 39. Although rounded part 72 of cap 66 sometimes touches the inner side 73, sheath inner side 73 is difficult to damage, even when rounded cap 66 rotates. Although depending on the sheath material, normally, gap 108 of 8 mm or so is needed between rounded cap 66 and tip cap 65, to produce a space for stretching due to the temperature rise of optical sheath 38 like nylon tube 64, and for relative movement of sheath 38 with flexible shaft 40, due to the bending. Fluoroplastic like FEP can be used as material of sheath 64.

Figure 9B:
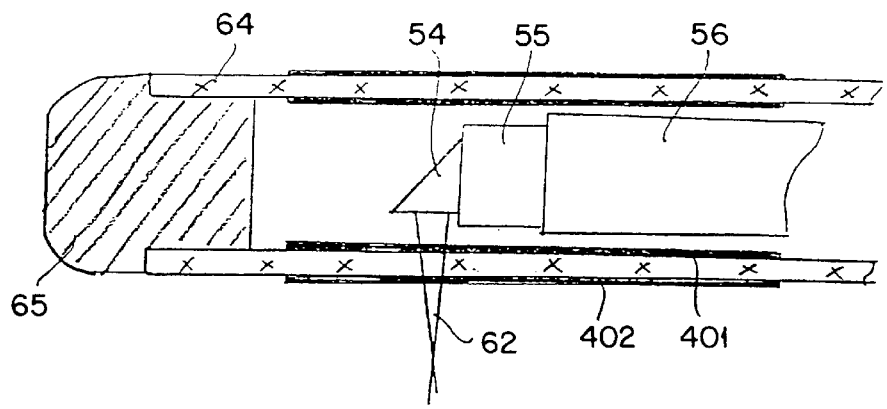
FIGS. 9B and 9C shows other structures of the probe tip.

FIG. 9B shows the other structure of the probe tip. The differences from FIG. 9A are reflection reduction coating 401 which is placed where the irradiation observation beam 62 is emitted inside of the nylon tube (sheath) 64. A reflection reduction coating 402 is also placed where the irradiation observation beam 62 is emitted outside of the nylon tube (sheath) 64. By such placement of the reflection reduction coating 401, the Fresnel reflection caused by the refractive index difference between the nylon tube 64 and air inside the tube is suppressed and thus the reduction of the emission light and detection light are avoided, and the inner reflection of the sheath surface is reduced. By placing the reflection reduction coating 402 thusly, the Fresnel reflection caused by the refractive index difference between the nylon tube 64 and medium such as air or water outside the tube is suppressed and causes similar effects as the reflection reduction coating 401. The ghosts caused by multiple reflection between the reflecting surfaces are also avoided.

Figure 9C:
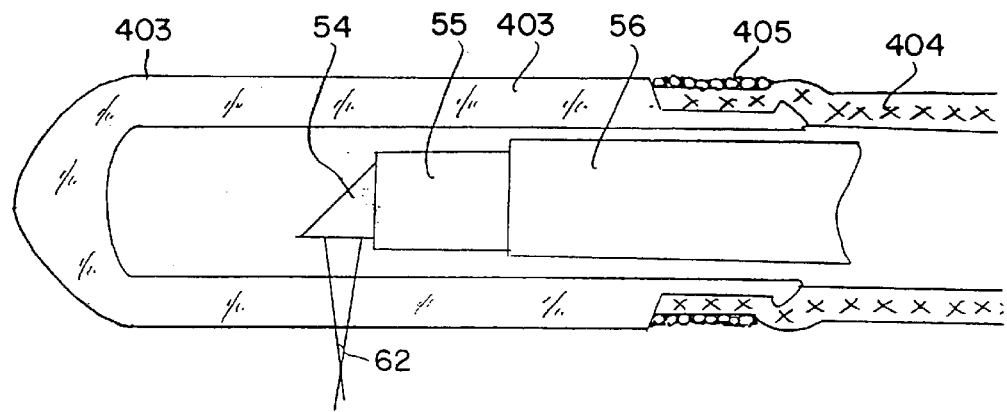

FIG. 9C shows the other realization of the probe tip. The tip cap 403 consists of glass or rigid plastic like polysulfone which is rigid and transparent to the observation light wavelength. The tip cap 403 is connected to the non-transparent resin tube 404 placed instead of nylon tube 64 by threads and adherent 405.

As the tip cap 403 consists of rigid transparent material, even when connection member 56 or lens frame 55 of lens unit 39 comes into contact with the interior of the tip cap 403, the observed images are not degraded by disturbing the observation beam 62 by scratch on the tip cap 403. Also, the improved optical quality of the rigid transparent material ensures the quality of the diffraction-limited focussed light spot in the tissue and the re-coupling of image-bearing light back into the single mode fiber in the probe. The tip cap 403 can consist of glass pipe and closed end part.

The same effects of FIG. 9C can be obtained when a thin hard coating like thin glass pipe is used instead of the reflection reduction coating 401 of FIG. 9B. It is only necessary for the glass pipe to be present where the light must traverse the sheath, and where the rotating prism may come into contact with the sheath. Especially when using a hard and flexible material such as thin ceramic coating, preferably polysilazane, an anti-wearable and flexible sheath can be realized.

The lumen between optical sheath 38 and lens unit 39 (FIG. 9A) can be filled with refractive index-matching fluid in order to reduce Fresnel reflections of observation light at the prism-air, and air-sheath optical interfaces. Opening 67 of rounded cap 66 transmits observation beam 62, and permits refractive index-matching water to permeate into the opening. Prism 54 may fail in total reflection because the reflection surface of prism 54 is wet with refractive index-matching water, and because the refractive indices of prism material is approximately equal to that of refractive index-matching water. In such cases, the reflection surface is coated with aluminum or dielectric multilayer coating, in order to ensure total reflection.

Figures 10, 10A:
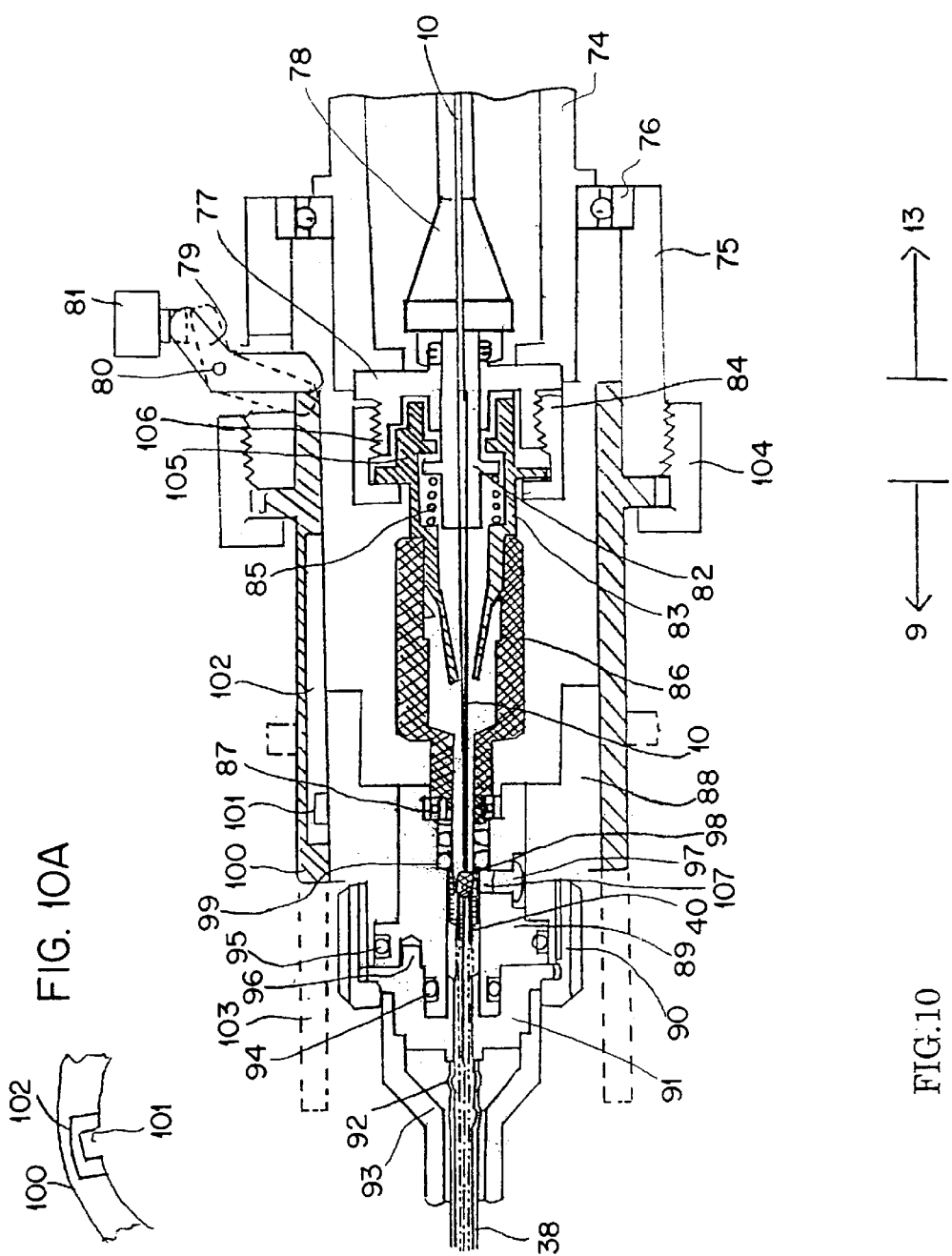
FIG. 10 shows a connector in detail in the first embodiment of the present invention.
FIG. 10A is an enlarged view perpendicular to a portion of FIG. 10.

FIG. 10 is a detailed illustration of connector 9 in FIG. 6. Optical sheath 38 is attached to projection 97 of sheath stopper 91. Sheath protector 93 is provided on sheath stopper 91. Flexible shaft 40 is attached to shaft stopper 86. Shaft stopper 86 is held by bearing seat 89 and bearing 87 so that the shaft stopper can rotate. Ferrule 82 is included in optical connector housing 83, and pressed by spring 85, against rotary drive 13. Optical connector housing 83 is joined to shaft stopper 86. Connector case 88 is tightly covered with slide pipe 100. Slide pipe 100 can slide relative to connector case 88, in lateral directions, to position 103 shown by dotted lines. Slide pipe 100 is fixed by attachment ring 104, to housing 75 of rotary drive 13. Rotation stopper 101 is provided on connector case 88, and recess 102 (both shown in FIGS. 10 and 10A) is provided in slide pipe 100; therefore, connector case 88 can possibly rotate only a little together with shaft stopper 86. A projection (not shown) is provided in the distal end part of slide pipe 100, and engages with a recess (not shown) provided in housing 75, to form a rotation stopper. In such a composition, slide pipe 100 is fixed by attachment ring 104, to housing 75 so that they cannot rotate relative to each other.

Optical adapter 77 in FIG. 10 is provided at the distal end of rotary shaft 74 of rotary drive 13. Optical connector 78 receives fiber 7 from optical rotary joint 6 (FIG. 8). Rotation stopper projection 105 is provided on optical connector housing 83. Optical adapter 77 has a recess 106 that engages with the projection. Optical connector housing 83 is fixed by set-screw 84, to optical adapter 77. Torque of rotary drive 13 is transmitted through the connection of optical adapter 77 and optical connector housing 83.

To connect connector 9 to rotary drive 13 (FIG. 8), the doctor slides slide pipe 100 (FIG. 10) to the dash line position 103, connects optical connector housing 83 and ferrule 82 to optical adapter 77, and tightens set-screw 84. Next, he or she inserts slide pipe 100 into housing 75, and fixes them with attachment ring 104.

Rotation of optical connector housing 83 causes shaft stopper 86 to rotate; and torque is transmitted to flexible shaft 40. Watertight junctions 98 are provided on shaft stopper 86, flexible shaft 40, and fourth single mode fiber 10.

As a watertight seal, O-ring 99 is provided between shaft stopper 86 and bearing seat 8. O-ring 94 is provided between sheath stopper 91 and bearing seat 89. Even if a space between optical sheath 38 and flexible shaft 40 is filled with refractive index-matching fluid, these watertight seals prevents fluid from escaping. It is possible to pour refractive index-matching fluid into fluid inlet 107 provided on bearing seat 89. Fluid, which has flowed into the gap in flexible shaft 40, cannot possibly escape from the inside.

FIG. 26A shows an image obtained by this device. Radial scanning image 184 is displayed. On the screen, distance scales 185*a* and 185*b* are provided for measurement. Scale 185*a* indicates a scale that corresponds to optical length in the air. Scale 185*b* indicates a scale consistent with a refractive index n of, for example, 1.4 which is an average of biological tissues. Scale 185*b* is, for example, 1.4 times the scale 185*a*. Optical length is expressed as n per unit of actual length.

As shown in FIG. 26B, it is possible to magnify half the scanned image, and display the magnified image 186. This is selected using a magnification and display range selector switch (not shown) on the keyboard. On the keyboard, a rotation angle control switch (not shown) is provided which can turn the image, in order to orient the displayed image toward the observation image (not shown) of the endoscope.

FIG. 26C illustrates another embodiment of a scale for distance measurements. An image processing algorithm is implemented which detects which regions in the image correspond to air 250, 252 and which regions correspond to tissue 251. The scale is then displayed which indicates a scale consistent with a refractive index n of 1 in the air regions, and a refractive index of, for example, 1.4 in the tissue regions.

FIG. 27 shows a composition of the entire device. The composition shown in FIG. 6 is included in observation device 187. Monitor 26 is installed on observation device 187. On observation device 187, probe drive unit 188 is provided which can move back and forth, in order to attach optical scanning probe 8. Capability of moving back and forth facilitates manipulation of long endoscopes used in lower digestive tracts. The front panel of observation device 187 includes optical system adjustment panel 189 on which keyboard 190 is provided. Foot switches 191 are connected to observation device 187. Freeze switch 192 and release switch 193 are included in foot switches 191. Operating freeze switch 192 can stop and release real-time display of the obtained images. Operating release switch 193 can store in the computer, or print the stopped image.

Second Embodiment

Next, the second embodiment is explained. The second embodiment is able to compensate for the stress-induced birefringence of the fiber bent and varied in quality so that it may be introduced into the patient's body cavity, and to compensate for the stress-induced birefringence of the fiber varied in quality, depending on the rotation of radial scanning in the patient's body cavity.

Figure 11A:
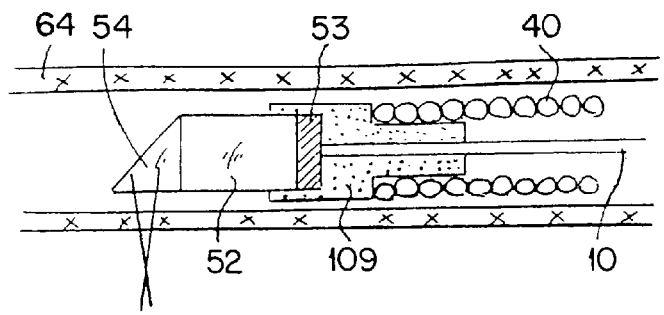
FIG. 11A shows an optical scanning probe in the second embodiment of the present invention.

FIGS. 11A through 13 show optical scanning probe tips using a Faraday rotator in other embodiments. The composition shown in FIG. 11A is almost the same as in FIG. 9A, except for the use in FIG. 11A of integrated lens frame 109 including connection member 56 and ferrule 69. Faraday rotator 53 is provided in a space between the end part of optical fiber 10 and GRIN lens 52.

Figure 11B:
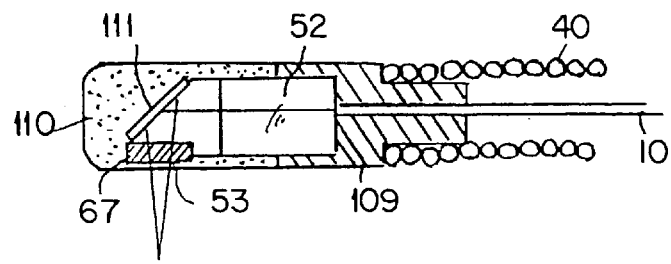
FIG. 11B shows an optical scanning probe in a modified second embodiment.

In the embodiment of FIG. 11B, reflection mirror 111 is provided inside tip cap 110 which is in contact with lens frame 109 so that the tip cap may cover GRIN lens 52. Faraday rotator 53 is embedded in opening 67. Observation light is reflected by the mirror, and sent from opening 67 to the outside.

Figure 11C:
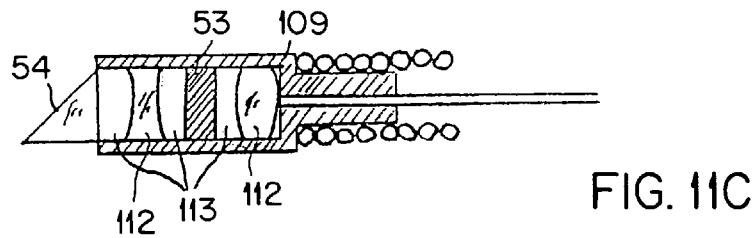
FIG. 11C shows an optical scanning probe in a further modified second embodiment.

In the FIG. 11C embodiment, instead of GRIN lens 52 in FIG. 9, a group of lenses, which includes single lens 112 and interval tube 113, incorporates Faraday rotator 53. This composition can be used to correct aberration to a high degree; otherwise the GRIN lens would not be able to attain such a high degree.

Any one of the above-mentioned compositions has the ability to compensate for the birefringence of the fiber bent so that it may be introduced into the patient's body cavity, and for the birefringence of fiber 10 varied in quality, depending on the bending and rotating process following rotation of flexible shaft 40.

Figure 12:
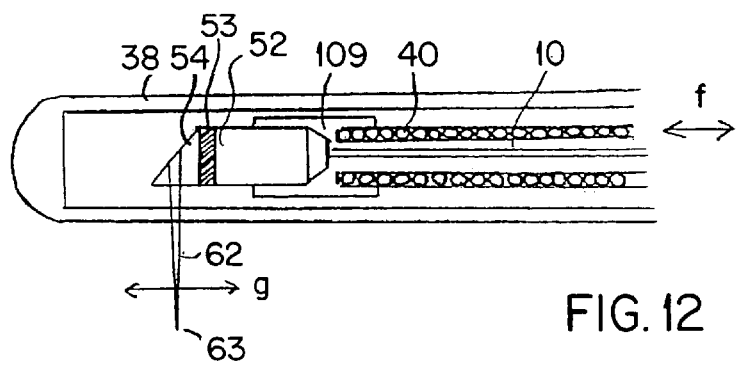
FIGS. 12 and 13 diagrammatically show an optical scanning probe in the further modified second embodiment of the present invention.

FIG. 12 shows an optical scanning probe that scans the tissue in longitudinal directions. Flexible shaft 40, GRIN lens 52, Faraday rotator 53, prism 54, and single mode fiber 10 are joined by lens frame 109. Swinging flexible shaft 40 to right and left in the f directions enables scanning the tissue with observation beam 62 and focus 63 to right and left in the g directions, to produce an image.

Figure 13:
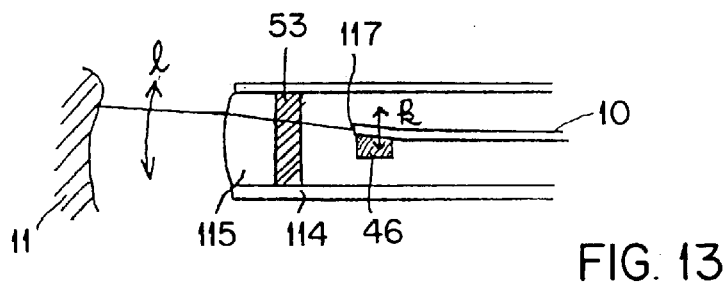

FIG. 13 shows an optical scanning probe that scans the tissue to the front of the scanner probe. The optical scanning probe includes objective lens 115, Faraday rotator 53, lens frame 109 supporting them, single mode fiber 10, and piezoelectric element 116 that swings fiber tip 117 upward and downward in the k direction. Piezoelectric element 116 swings fiber tip 117 upward and downward in the k direction; the observation beam is thereby swung upward and downward in the l direction, to produce an image.

Either of the arrangements in FIGS. 12 and 13 has the ability to compensate for the birefringence of fiber 10 bent and varied in quality so that it may be introduced into the patient's body cavity.

Third Embodiment

The third embodiment is able to provide a high-resolution two-dimensional image, by high-speed scanning using optical length-varying means based on the delay line of mirror oscillation type.

Described below is a method of producing a radial image, by scanning of 1 line in the depth direction, and by the use of flexible shaft 40 in optical scanning probe 8 to turn the distal end optical system.

FIG. 14A shows relationships between depth direction scanning position curve 118 obtained by the movement of galvanometer mirror 19 (either from the position encoder signal in the galvonometer, or from the galvanometer driver signal), mirror scanning timing signal 119 obtained by galvanometer controller 20, interference signal 120 (the envelope of the interferogram signal) obtained by depth direction scanning, and line memory 121 storing the interference signal. The abscissa indicates time.

To maximize scanning speed with galvanometer mirror 19, it is effective to use the same waveform in scanning to and fro with the mirror, as denoted by curve 118. In such cases, interference signal 120 is divided into two substantially symmetrical waveforms with respect to mid point 123 in the to-and-fro path: waveform 122a and waveform 122b. In addition to waveform 122a, waveform 122b may be used to produce a radial image. In such cases, it is possible to obtain double radial resolution. Interference signal 120 is stored in line memory in time series.

Data in line memory 121 is copied to two-dimensional frame memory 172 shown in FIG. 14B. Because of the nonlinear mirror scanning, as shown in waveform 118, we do not use that part of data stored in line memory 121 which corresponds to the range from timing signal 119 to time $t_1$. Only linear section of $t_2$ is copied to the first line in frame memory, with directions preserved at the first position $a_1$ and the last position $b_1$ in memory. The nonlinear section of $t_3$ from position $b_1$ to position $c_1$ where positions $b_1$ and $c_1$ are symmetrical with respect to midpoint 123. Linear section $t_4$, from $c_1$ to $d_1$ where positions $a_1$, and $d_1$ are symmetrical with respect to midpoint 123, is copied to the second line in frame memory 172 (FIG. 14B), with directions reversed at the first position $c_1$ and the last position $d_1$ due to scanning mirror 19. Thus, frame memory 172 can store interference signal 120 which is produced by scanning in the same directions, and which is slightly different in radial position.

Figure 14C:
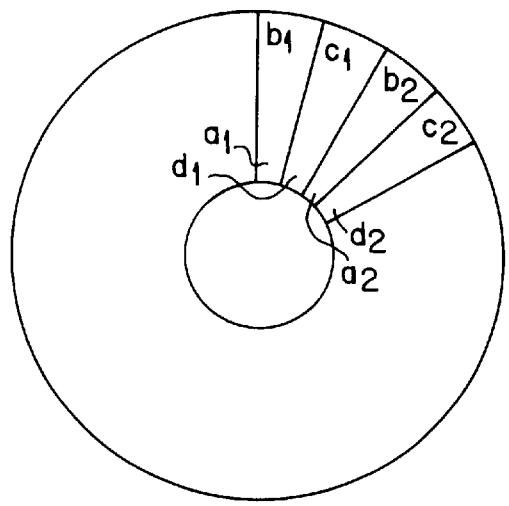
FIG. 14C is diagram showing the relationship between data in the memory and graphical point.

For the next timing signal 173, the above procedure is followed. Repeating that procedure produces a two-dimensional image of interference signals. This image resembles that of interference signals obtained by scanning in the same directions, instead of the radial directions per cycle. With the probe side positioned at the center, as shown in FIG. 14C, this is converted into a circle, to produce a radial image. This method is named "double sided scan."

Figure 15:
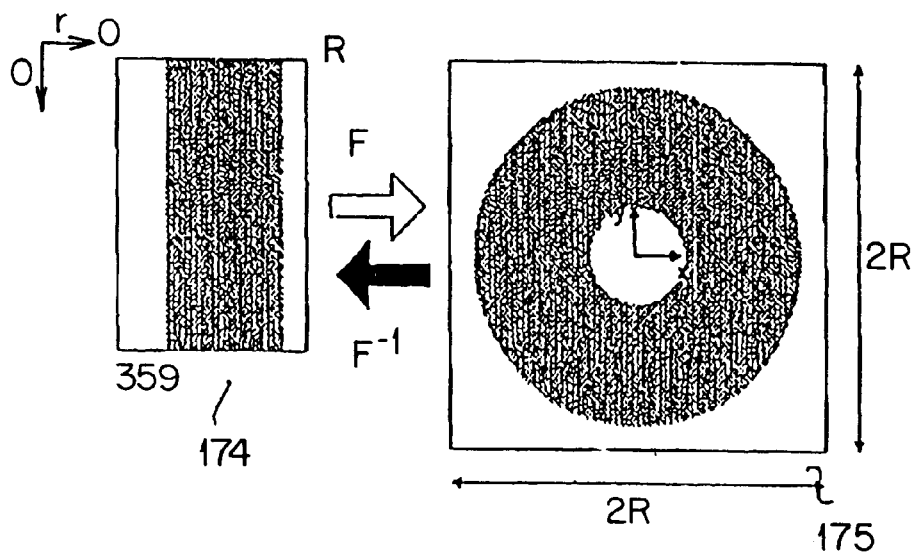
FIG. 15 is a diagram showing conversion between a two-dimensional image and a radial image.

FIG. 15 shows an algorithm for quickly converting a rectangular image as shown in FIG. 14B, into a radial image as shown in FIG. 14C. As shown in the left-hand part of FIG. 15, two-dimensional image 174 has: the x direction which corresponds to the depth direction r; and the y direction which corresponds to rotation angle . In order to convert the x-y (Cartesian) coordinate system into the r- (polar) coordinate system 175 in the right-hand part of FIG. 15, the following conversion F is used:

$$\sin(\ )x(r,\theta)=r\cos(\theta)$$

$$y(r,\theta)=r\sin(\theta)$$

where (x(r,θ), y(r,θ)) represents the coordinate system shown in the right-hand part of FIG. 15. In reality, since both image 174 and image 175 are sets of pixels, a simple procedure for the use of this conversion equations to convert image 174 into image 175, however, produces an image that includes sparse pixels on or near the circumference. Inverse conversion F is as follows:

$$r(x,\ y)=\sqrt{(x^2+y^2)}$$

$$(x,\ y)=\tan^{-1}(y/x).$$

A correspondence relationship is obtained by the use of the inverse conversion F. Since two or more pixels in image 175 correspond to one pixel in image 174, the use of such correspondence relationship can produce an image that does not lack pixels. The correspondence relationship is stored in a mapping array. The mapping array is a matrix the same size as the destination (e.g. polar) image, whose elements contain pointers to the memory locations of the corresponding pixel values in the stored rectangular image, according to the relationships expressed in the equations above. According to the pixel correspondence relationship stored in the array, even a low-processing power personal computer can convert image 174 into image 175, to produce real-time radial images.

Figure 16:
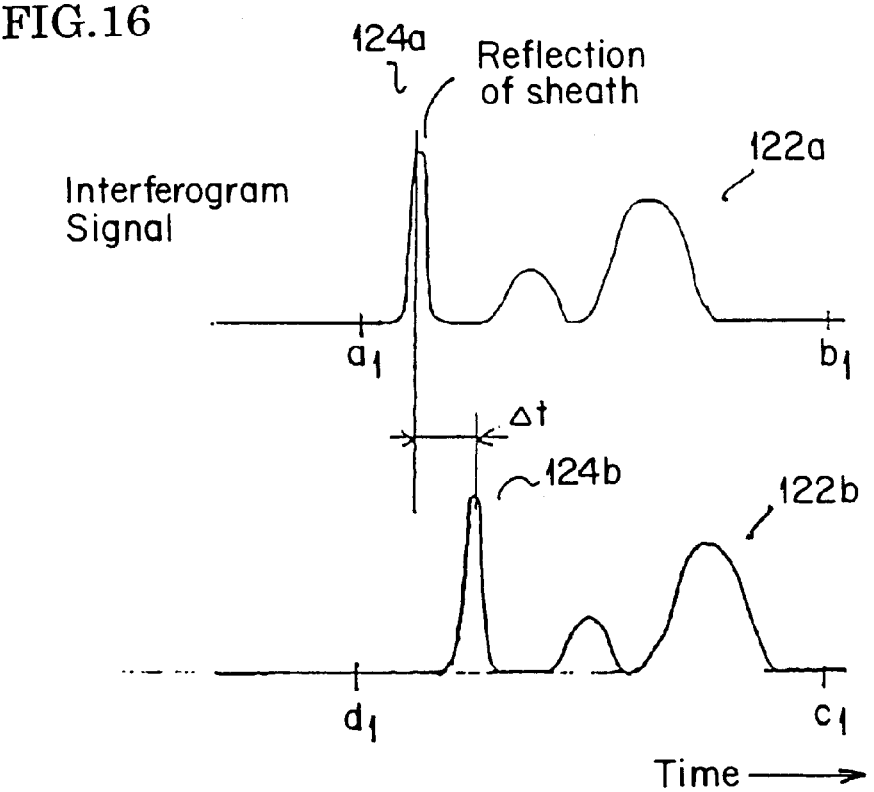
FIG. 16 is a time chart showing an interference signal.

In reality, in the double sided scan method, galvanometer mirror 19 (FIG. 6) and galvanometer controller 20 have inferior temperature characteristics that cause symmetry to fluctuate with respect to scanning midpoint 123 (FIG. 14A). FIG. 16 shows such a state. Displaying a radial image in this state, unfortunately, produces overlapped borders, and extremely low-quality images. Waveform 122b is stored in frame memory 172. As shown in FIG. 16, waveform 122a and waveform 122b are out of phase by timet in the time Δt direction. Peaks denoted by 124a and 124b are caused by reflection on the surface of probe sheath 64. Such reflections have much higher signal intensity than scattering by the biological tissue. Signals that exceed a predetermined threshold are regarded as reflection on the surface of probe sheath 64. It is possible to eliminate out-of-phase waveforms in the time direction, and to prevent picture quality from becoming inferior, by detecting peaks 124a and 124b and varying time interval $t_3$ in FIG. 14A so that they may coincide with each other.

Phase adjustment knob 160 is provided on optical system adjustment panel 189 shown in FIG. 23. The position of the knob is detected by the use of a potentiometer (not shown) connected to phase adjustment knob 160. While observing the actual image, the doctor can eliminate phase deviation by manually turning phase adjustment knob 160, in order to change the interval time $t_3$ in FIG. 14A, according to the knob position. On optical system adjustment panel 189, manual/auto selector switch 162 is provided to select manual adjustment with the phase adjustment knob, or automatic adjustment using reflection on the surface of probe sheath 64.

FIG. 30 illustrates another method of collecting double-sided scan data and converting the data to a radial image display using a mapping array instead of FIG. 14B. The data recording device records to frame memory all of the data collected during time $t_2$, $t_3$, and $t_4$ to a single line. The mapping array, in addition to converting the data from rectangular to polar format, maps data collected during time $t_2$ to one radial image line, and data collected during time $t_4$ to the adjacent radial image line in a reverse manner. Thus, both forward and reverse line data are mapped successfully to the radial display, and the data collected during time $t_3$ is not used in the radial display because the mapping array does not point to this data. This method eliminates the need to write line data to frame memory in a forward and reverse manner. The mapping array reverses the data with no on-line computation. The only drawback to this method is the small additional amount of frame memory required to store the unusable data collected during time $t_3$. Phase adjustment can be performed similarly as the above method, by providing means to adjust the duration of time $t_1$ and/or time $t_3$.

Figure 17:
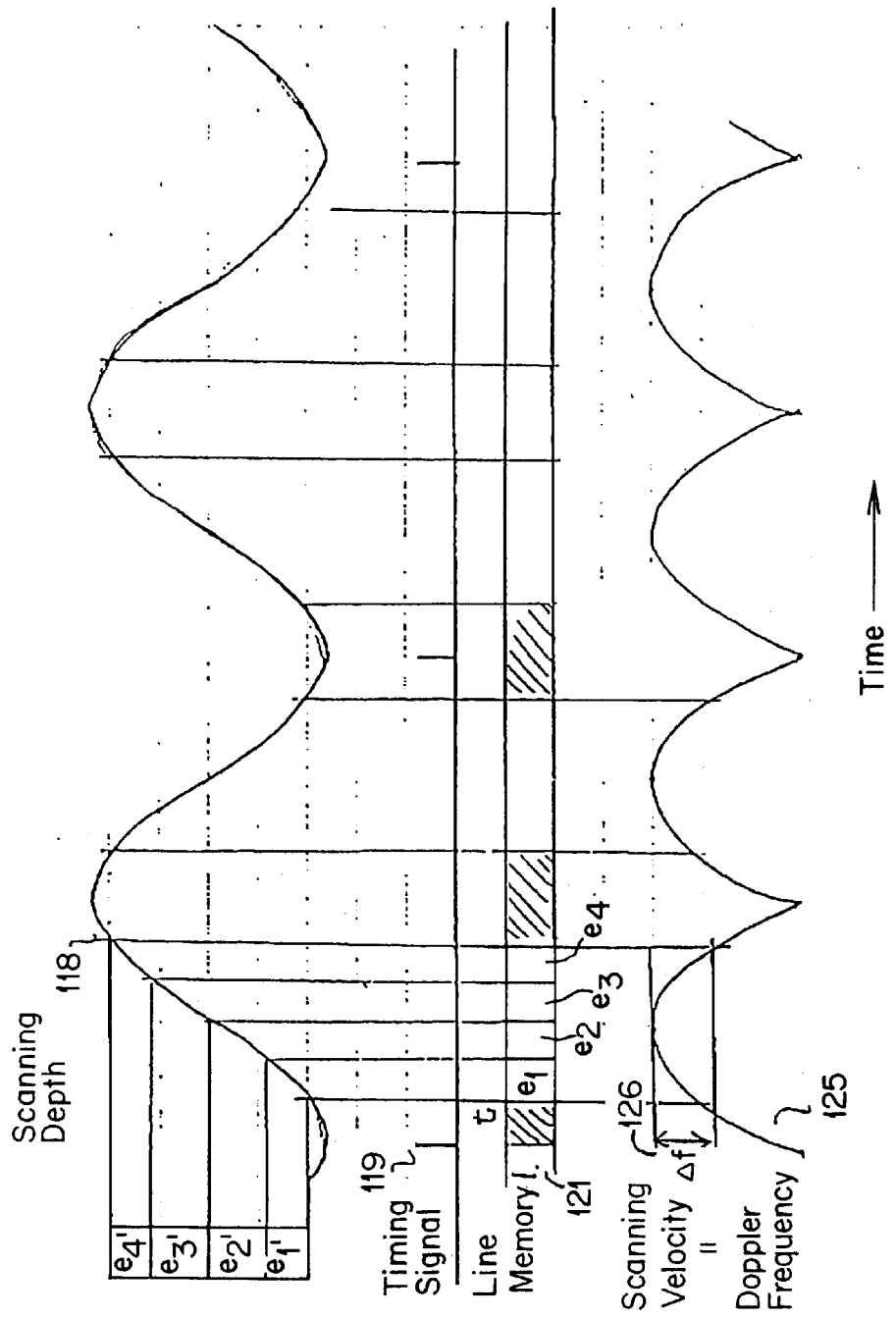
FIG. 17 is a time chart showing the relationship between a depth direction scanning position curve and a timing signal.

In addition to FIG. 14A, another method uses resonant scan mirror instead of galvanometer mirror 19, to further accelerate scanning with the mirror. In such cases, as shown in FIG. 17, the mirror is swung at resonance frequency in the form of a sine wave; therefore, scanning depth also varies in the sine-wave manner. In such cases, interference signals are used in sections $e_1$ through $e_4$, included in relatively nearly linear range. Sections $e_1$ through $e_4$ have the same intervals; whereas they differ in scanning depth, as denoted by $e_1$ through $e_4$. To produce an image, it is necessary to convert data on sections $e_1$ through $e_4$ stored in line memory 121, into linear data in the depth direction. The mapping array can also include the calculation to thus de-warp the image according to the following relation:

$$\text{Depth position } dp = A \cos(\omega(t-t_1)) + B \, (A, B, \omega: \text{constants})$$

The speed of moving the mirror is the Doppler frequency of optical heterodyne detection, which is proportional to the time derivative of the depth position as shown in curve 125. During sections e1 through $e_4$, Doppler frequency varies $\Delta f$ 126.

Figure 18:
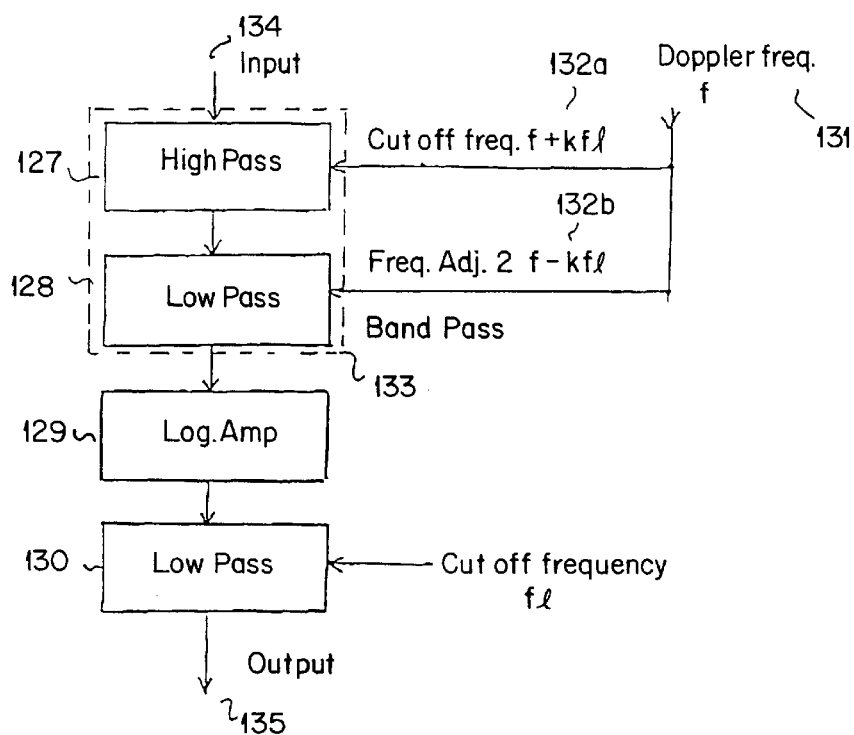
FIG. 18 is a block diagram showing a demodulator.

FIG. 18 shows a composition of demodulator 23. Demodulator 23 includes: a band-pass filter 133 which includes high-pass filter 127, and low-pass filter 128; and a demodulating logarithmic amplifier 129 having envelope-detection capability; and a low-pass filter 130. Band-pass filter 133 extracts only components modulated by Doppler frequency of optical heterodyne detection. The demodulating logarithmic amplifier 129 performs envelope-detection and logarithm amplification, in order to convert biological-tissue scattering signals having a wide dynamic range, into display signals having a narrower dynamic range suitable for analog-to-digital conversion. Low-pass filter 130 removes higher-order modulation signals and broadband electrical noise, to produce envelope signals that include scattering information.

As shown in FIG. 17, if the Doppler frequency varies $\Delta f$ 126, it is necessary to widen the pass band of band-pass filter 133. In such cases, the filter transmits additional noise components to reduce signal-to-noise ratio. As shown in FIG. 18, scanning speed is detected in a real-time manner. Doppler frequency f 131 is calculated and added to frequency $f_1$ of low-pass filter 130 multiplied by coefficient k to produce the cut-off value 132a of high-pass filter 127; whereas the difference between Doppler frequency f 131 and f1 multiplied by k is cut-off value 132b of low-pass filter 130. Both cut-off values 132a and 132b are inputted, and used in a real-time manner. Alternatively, a single band-pass filter with a tunable center frequency and an appropriate bandwidth is used. The detected or calculated Doppler frequency is used directly, or by converting to a proportional voltage using a frequency-to-voltage converter, to tune the center frequency of the band-pass filter in real time. It is possible, thus, to minimize the inferior signal-to-noise ratio, due to the variation in Doppler frequency f.

A second embodiment of the demodulator 23 which preserves high signal to noise ratio even in the event of nonlinear reference arm scanning is the coherent tracking demodulator illustrated in FIG. 28. As shown in FIG. 28, The input signal from the amplifier is first band-pass filtered using cascaded high-pass filter 201 and low-pass filter 202 set to pass the entire frequency content of the desired portion of the nonlinearly modulated interferometric signal, Df. The band-passed signal then serves as the input to two mixers 205 and 206. A reference signal generator 203 produces a frequency-modulated reference signal whose frequency is proportional at every instant to the derivative of the position of the reference delay scanner, which is calculated to be equal to the instantaneous Doppler shift of the reference arm light. This signal is mixed with the band-passed interferometric signal in mixer 205 to generate the in-phase component I of the demodulated signal. A second copy of the reference signal is delayed by 90 degrees in a phase shifter 204 and mixed with the band-passed interferometric signal in mixer 206 to generate the quadrature component Q of the demodulated signals. Both I and Q components are then filtered in low-pass filter 207 and high-pass filter 208 and combined into a single magnitude signal in power combiner 209. The output 210 is digitized in the analog-to-digital converter. Alternatively, the magnitude calculation may take place after separate digitization of the I and Q components in the computer. This tracking generator has the advantage of automatically following nonlinearities in the reference arm Doppler shift without requiring rapid adjustment of filter parameters.

Fourth Embodiment

The forth embodiment is able to damp out undesired DC components of the detected light signal from internal probe reflections, to intensify interference optical signals, and to improve the signal-to-noise ratio of the detection system.

Figure 19:
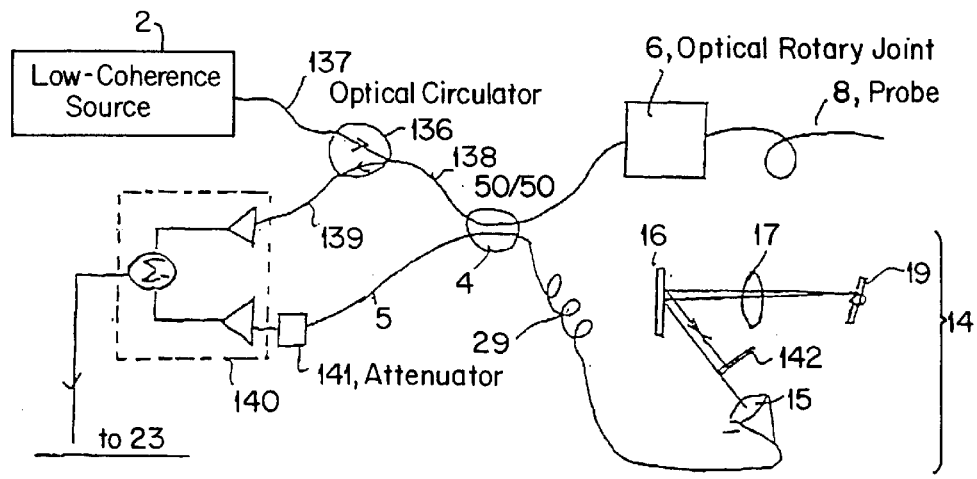

FIG. 19 shows the fourth embodiment. Described below are differences between the first embodiment in FIG. 6 and the fourth embodiment in FIG. 19.

Optical circulator 136 is provided along the path of the first single mode fiber 3 (SMF) in FIG. 6. SMF is divided into two: division 137 and division 138. Optical circulator 136 has three ports connected to SMF 137, SMF 138, and SMF 139. One end of attenuator 141 is connected to the end of second single mode fiber 5. The other end of attenuator 141 and SMF 139 are connected to differential detector 140.

Optical circulator 136 can transmit light, with low damping, only in two directions from SMF 137 to SMF 138, and from SMF 138 to SMF 139. The optical circulator cuts off light transmission in other directions. Observation light is emitted from low coherence light source 2, through SMF 137, through SMF 138, and through coupler 4, to a subject side where optical scanning probe 8 exists, and on the reference side to variable-optical length mechanism 14. At coupler 4, reflection from the subject combines with reflections from the reference. Interference light, with the opposite phase, is transmitted to SMF 138 and SMF 5, and slightly damped by optical circulator 136, and then is transmitted to SMF 139. Attenuator 141 is adjusted so that intensity from SMF 139 may have the same steady component as intensity from SMF 5. They are thus inputted to differential detector 140. Detector 140 amplifies the difference between optical amplitude for SMF 139 and optical amplitude for SMF 5, and sends an output to demodulator 23 in FIG. 6. SMF 138 interference light has the opposite phase to that of SMF 5 interference light. Since in the optical system, steady light and internal reflections, other than interference light, have the same phase, calculating the difference damps steady light components greatly; whereas interference light doubles approximately. Also, common mode noise, such as excess source intensity noise, is mostly rejected. In interference signal detection, it is possible, thus, to improve the signal-to-noise ratio maximum by 20 dB or so.

Double-pass mirror 142 in FIG. 19 is provided on the optical path in variable-optical length mechanism 14. In variable-optical length mechanism 14 in FIG. 6, light is sent from second first single mode fiber 5, through lens 15, through grating 16, through lens 17, through galvanometer mirror 19, through lens 17, through grating 16, and through 15, and returned to the fiber end. Double-pass mirror 142 is provided in FIG. 19 so that light may be passed through grating 16 and through galvanometer mirror 19 four times. The optimal placement of the double-pass mirror is either directly underneath or else above the light path from collimator 15 to grating 16, i.e., out of the plane of FIG. 19. The principle of double-pass scanning is described in detailed in "In vivo video rate optical coherence tomography" (A. M. Rollins et al. supra). It is advantageous to double-pass scanning in FIG. 19 so that substantially constant intensity can be obtained, and so that interference light amplitude is stable despite the rotation angle. Since light is passed through the optical path four times, it is advantageous to double-pass scanning that even variable-optical length mechanism 14 of the same composition can provide longer variations in optical length.

FIG. 20 shows another embodiment using an optical circulator 13b. FIGS. 6 and 19 show embodiments based on the Michelson interferometer. FIG. 20 shows an embodiment based on the Mach-Zehnder interferometer.

Low coherence light source 2 is connected to first single mode fiber 3, and connected to optical coupler 148. One output of the optical coupler is connected SMF 164, and connected to optical circulator 136. Optical rotary joint 6 and SMF 165 are connected to optical circulator 136. Optical scanning probe 8 is connected to optical rotary joint 6.

The other output of optical coupler 148 is connected, through polarization adjusting fiber loop 29, to SMF 167. SMF 167 is passed through transmission delay line 143, and connected to SMF 166. SMF 165 and SMF 166 are connected to optical coupler 147. The output of optical coupler 147 is connected to dual-balanced (differential) detector 140.

Observation light is emitted from low coherence light source 2, and passed through SMF 3, and guided to optical coupler 148. Light is divided into the ratio of $\alpha_1:(1-\alpha_1)$ and sent to SMF 164, and to SMF 167. Light is sent to SMF 164, and passed through optical circulator 136, sent through optical rotary joint 6, and through optical scanning probe 8, to irradiate the object of observation with light. Reflection from the object of observation is passed through optical rotary joint 6, and through optical circulator 136, and sent to SMF 165.

Light is sent to SMF 167, and incident on transmission delay line 143 that corresponds to variable-optical length mechanism 14 shown in FIG. 6. Light is sent from the end part of SMF 167, converted by collimator lens 145 into parallel rays. Parallel rays are transmitted through beam splitter 146, and incident on grating 16. As in variable-optical length mechanism 14, the incident light is transmitted through lens 17, and reflected by mirror 19, and sent through lens 17, and returned to grating 16. Returned light is reflected by beam splitter 146 toward collimator lens 144, and condensed onto the end part of SMF 166. Transmission delay line 143 can vary optical lengths of SMF 166 and SMF 167, in accordance with the same principle as variable-optical length mechanism 14. Rays are sent from SMF 166 and from SMF 165. In optical coupler 147, the rays interfere with each other. Interference light is obtained by optical coupler 147, and detected by detector 140, to produce the high signal-to-noise ratio, as described above relative to FIG. 19.

A more efficient version of the transmissive delay line 143 is illustrated in FIG. 29. Light is sent to and SMF 167 and is incident on transmission delay line 143 which corresponds to variable-optical length mechanism 14 shown in FIG. 6. Light is sent from the end part of SMF 167, converted by collimator lens 145 into parallel rays. Parallel rays are incident on grating 16. As in double-pass variable-optical length mechanism 14, the incident light is transmitted through lens 17, and reflected by mirror 19, and sent back through lens 17, and returned to a double-pass mirror 142. Returned light travels back through grating 16, lens 17, grating 19, then is reflected by galvonometer mirror 19 back through lens 16 and off of grating 16 before being re-directed by pick-off mirror 220 into collimator lens 144, and condensed onto the end part of SMF 166. The double-pass mirror 142 and pick-off mirror 220 may be displaced vertically from the plane of the drawing in FIG. 29, i.e., above and below the beam emerging from collimating lens 145. This transmissive delay line has the advantage that no reference arm light is sent back into the low-coherence source 2 where it would be wasted.

Fifth Embodiment

The fifth embodiment is able to provide high-precision scanning speed and positioning, and to improve the signal-to-noise ratio by stabilizing scanning speed.

FIG. 21 shows another embodiment of variable-optical length means 14 shown in FIG. 6. Instead of galvanometer mirror 19, polygon mirror 149 is provided. If the center 152 of polygonal mirror 149 is provided on optical axis 153 of lens 17, one surface of the polygon, surface 150, is perpendicular to optical axis 153. If the polygonal mirror is turned by θ as shown by dash line, surface 151 becomes not quite perpendicular to optical axis 153. The change in interference position Δ1 obtained by rotation θ is expressed as:

$$\Delta 1 = 4\theta f \times \lambda + 4q$$

$$q = (h - r\sin\theta)\tan\theta + r - r\cos\theta$$

where f represents focal length of lens 17, p represents the pitch of grating 16, λ represents the wavelength of light q represents the difference of optical length due to rotation and "h" represents the offset of the polygonal mirror axis from the optical axis. Rotation is expressed as θ=ω×t, where ω represents angular velocity, and t represents time. The changing rate of the difference in optical length per unit of time is: d q/d t and is proportional to the doppler frequency of the optical heterodyne signal.

Since the polygonal mirror rotates in a constant direction, depth direction scanning is not performed not alternately both in the positive and negative directions as in FIG. 14A. While the polygon rotates, whenever a new surface faces lens 17, scanning in the same direction is performed. In contrast to signal processing in FIG. 14A, and to the to-and-fro scanning in FIG. 16, polygonal mirror in FIG. 21 eliminates the necessity of phase adjustment. Because of the independence of phase deviation due to the temperature characteristics, it is possible to determine scanning position accurately. To adjust Doppler frequency by means of mirror rotation, and to produce a great variation in optical length, it is possible to make the center 152 of the polygonal mirror deviate from optical axis 153.

A specially designed drive signal may be used to linearize the scan effected by a resonant scanner. The ideal drive signal consists of a uniform triangular wave, representing a constant scan rate in one direction for exactly half of the waveform period, followed immediately by a constant scan rate in the opposite direction for the remaining half of the waveform period. A resonant scanner is driven by a sinusoidal drive signal, which can be interpreted as the first harmonic of the Fourier decomposition of the ideal drive signal. In order to effect a scan which is more linear, one or more additional harmonic components of the ideal drive signal can be superposed with the first harmonic component. The mechanical response of the scanner will attenuate higher frequency harmonic components, so more than one or two may not be possible. The higher frequency harmonic components can be amplified appropriately in order to compensate for their attenuation by the mechanical response of the scanner.

Sixth Embodiment he sixth embodiment is able to perform automatic and simple polarization plane adjustment of the OCT device.

FIG. 22 shows an embodiment of the polarization plane controller in FIG. 6. Single mode fiber (SMF) 154 includes: two ¼ wavelength loops 155a, 155b wound onto respective drums in predetermined turns such that the loops may have the same birefringence as a ¼ wavelength plate; and a ½ wavelength loop wound in predetermined turns such that the loops have the same birefringence as a ½ wavelength plate. The ¼ wavelength loop 155a, ½ wavelength loop 156 and ¼ wavelength loop 155b are fixed to shafts 157a, 157b and 157c respectively, and can rotate about shafts 157a, 157b and 157c respectively. Shafts 157a, 157b and 157c have bevel gear pairs 158a, 158b and 158c. Polarization adjustment knobs 159a 159b, 159c are connected to bevel gear pairs 158a, 158b and 159c, respectively.

Turning polarization adjustment knobs 159a 159b and 159c enables bevel gear pairs 158a, 158b and 158c to turn shafts 157a, 157b and 157c. As shafts 157a, 157b and 158c rotate, they turn ¼ wavelength loop 155a, ½ wavelength loop 156 and ¼ wavelength loop 155b about shaft 157a, shaft 157b and shaft 157c. Since ½ wavelength loop 156 and ¼ wavelength loop 155a, 155b have the same birefringence as a ½ wavelength plate and a ¼ wavelength plate respectively, it is possible to convert any one of the polarization states propagating on fiber 154, into any different polarization state. Based on this conversion, matching can be made which adapts the polarization caused by the birefringence of the reference fiber which has variable-optical length means 14, to the polarization caused by the fiber on the subject that has optical scanning probe 8. Optical coupler 4 can be used to obtain maximum interference light amplitude.

FIG. 23 shows a part of the OCT device control panel. Polarization adjustment knobs 159a, 159b and 159c, polarization initial adjustment switch 174, double sided phase adjustment knob 160, auto/manual selector switch 162, optical length adjustment knob 161, and auto/manual selector switch 163 are provided on the control panel.

It is possible to adjust the plane of polarization automatically. As shown in FIG. 22, shafts 157a, 157b and 157c are coupled to shafts of servomotors 175a,175b and 175c. The optical scanning probe tip is immersed in intralipid solution or uniform liquid with known reflection and scattering parameters. The doctor presses polarization initial adjustment switch 174 in FIG. 23. He or she measures an interference signal in liquid, and positions servomotors 175a, 175b and 175c so that the interference signal may be maximized by the use of feedback control over servomotors 175a, 175b and 175c. Once the maximum has been set, if the servomotors are turned OFF, it is possible to adjust polarization, by manually turning polarization adjustment knobs 159a, 159b, 159c.

It is also possible to realize a polarization controller by using only one ½ wavelength loop 156 and only one ¼ wavelength loop 157a.

A polarization plane controller can also be realized by other ways which have the same effects as the controller in FIG. 22 such as to pressure the fiber and control angle and strength of pressure and using Berek polarization compensator. To use such controllers, only two parameters should be adjusted to match polarization. It is easier to adjust polarization both in manual- and auto-adjustment.

Instead of the immersion in solution like intralipid, test tools 176, 177, and 300 in FIGS. 24A, 24B and 24C, respectively, can be used to adjust the plane of polarization. FIG. 24A shows an examplar test tool. In container 168, insertion hole 170 is provided through which an optical scanning probe 8 is passed. Inside container 168, scattering layers 169a and 169b are provided which contain media of different scattering coefficients. Media include latex beads, and $TiO_2$, $BaSO_4$ and other substances solidified by epoxy.

FIG. 24B shows test tool 168. Inside container $168^1$, scattering and reflection membrane 171 is provided which has known reflectance.

FIG. 24C shows test tool 300. Test tool 300 consists of an integrating sphere.

These test tools can be used not only to adjust the plane of polarization. They can also be used as test charts which indicates that the OCT device functions normally.

Next, seventh, eighth and ninth embodiments will be explained. These embodiments are related to the end optical system on the side of the signal light of the optical tomography diagnosis device that ghosts do not appear and an S/N ratio is advanced. It is possible to obtain such since the number of times of reflection on the end surface of an optical element of an end optical system on the side of signal light of an optical tomography diagnosis device of less than three times does not return to a single mode fiber.

Here, an optical axis of a refractive index distribution lens is, however, the axis of refractive index distribution of a refractive index distribution lens. In the end optical system on the side of signal light according to the present invention, it is defined that the optical axis of the refractive index distribution lens in case of using an optical element deflecting the direction of observing by reflecting light and the optical axis of a single mode fiber are symmetrically reflected on the reflecting surface of the optical element for deflecting the direction of observing.

For example, in case of an optical system of as in FIG. 31, the optical axis of the refraction index distribution lens 241 is like a line L1 on the side of the single mode fiber 245 and like a line L2 on the side of an object from the reflecting surface of prism 243 as the optical element for deflecting the direction of observing.

Embodiment 7

FIG. 32 shows a seventh embodiment of an end optical system of signal light of an optical tomography diagnosis device according to the present invention. An end part on the side of the signal light includes a single mode fiber 245 on the side of the signal light, a refractive index distribution lens 241 with a light gathering effect, a Faraday rotator 242, prism 243 for deflecting the direction of observing and a sheath 247, each of which is cemented. FIG. 33 is that FIG. 32 is linearly redrawn so that an angle of the refractive index distribution lens 241 with a light gathering effect to the optical axis is easily understood.

Data of the seventh embodiment according to the present invention is as follow: s is the number of a surface, R is a curvature radius of an end surface of each optical element, d is an interval between surfaces, n is a refractive index, θs is an angle of a normal line of an end surface to an optical axis of a refractive index distribution lens 241 and ER is an effective radius.

Further, $n_0$ and A at the lower step of data are constants of a refractive index distribution lens 241 on a fourth surface, $n_0$ is a refraction index on an optical axis of the refraction index distribution lens 241, and A is a refractive index distribution constant.

The refractive index n (r) of a distance from an optical axis of a refractive index distribution lens is represented by two constants as above mentioned as follows.

$n(r)=n_0(1-Ar^2/2)$

Further, as a sixth and a seventh surface are cylindrical sheaths according to the present embodiment, they are described by a longitudinal curvature radius Ra of a cylindrical surface and a radical curvature radius Rr.

Data of Embodiment 7

A single mode fiber NA=0.13, θf=6°, arcsin(NA/n)=5.1°

Decentering amount between optical axes of a single mode fiber and a refractive index distribution lens=0

An angle of incidence on a normal line of chief light ray: 11.7°

| s  | R | d    | n     | θ s | ER    | Note |
|----|---|------|-------|-----|-------|------|
| s1 | ∞ | —    | 1.46  | —   | 0.005 | n is a value of a core of a single mode fiber |
| s2 | ∞ | 3.28 | *1    | 6   | 0.5   | A refractive index distribution lens |
| s3 | ∞ | 0.31 | 2.36  | 6   | 0.5   | A Faraday rotator |
| s4 | ∞ | 1.15 | 1.854 | 6   | 0.5   | A Prism |
| s5 | ∞ | 0.4  | 1     | 7   |       |      |

-continued

| s  | R  | d   | n    | θ s | ER | Note |
|----|----|-----|------|-----|----|------|
| s6 | *2 | 0.3 | 1.53 | 7   |    | A Sheath |
| s7 | *3 | —   | 1    | 7   |    |      |

*1 A refractive index distribution lens $n_0$ = 1.592, √A = 0.597
*2 A cylindrical surface Ra = ∞, Rr = −0.9
*3 A cylindrical surface Ra = ∞, Rr = −1.2

According to the present invention, the end surface of each of the optical elements is not perpendicular to a flux of incident signal light. Since the number of times of reflection of that light between end surfaces of each of optical elements in an end optical system on the side of the signal light is less than three, that light does not return to the single mode fiber 245. Consequently, the end surfaces of all the optical elements of the end optical system on the side of the signal light, that is to say, the end surfaces of the single mode fiber, both ends of the refractive index distribution lens, both ends of the Faraday rotator 242, the end surfaces on the incident and the outgoing side of prism 243 are slantedly polished to the optical axis of the refractive index distribution lens respectively.

Figure 34A:
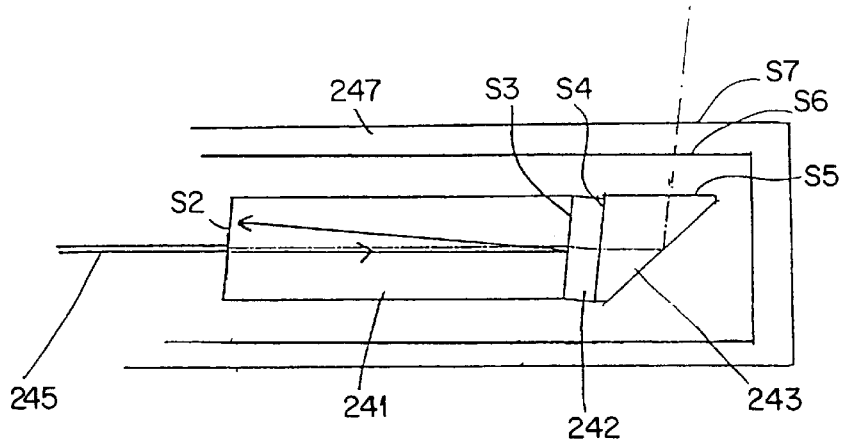
Figure 34B:
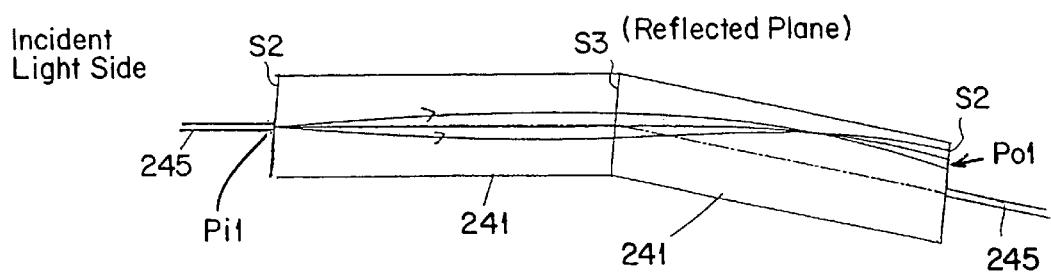
Figure 34C:
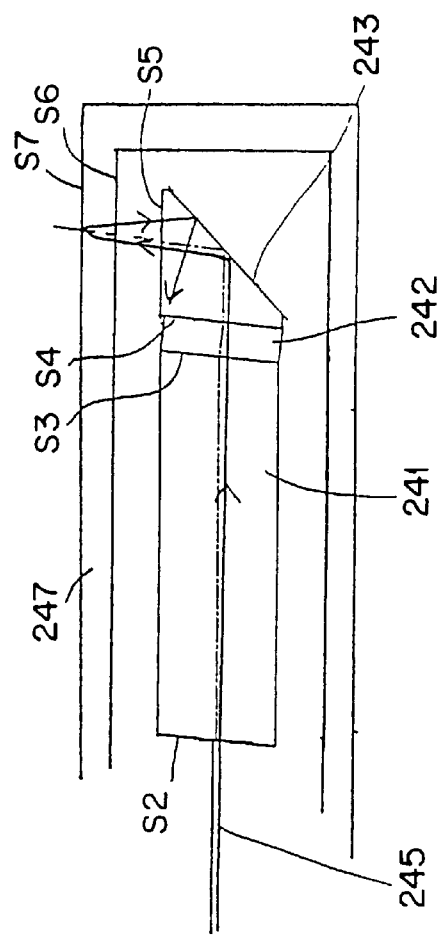
Figure 34D:
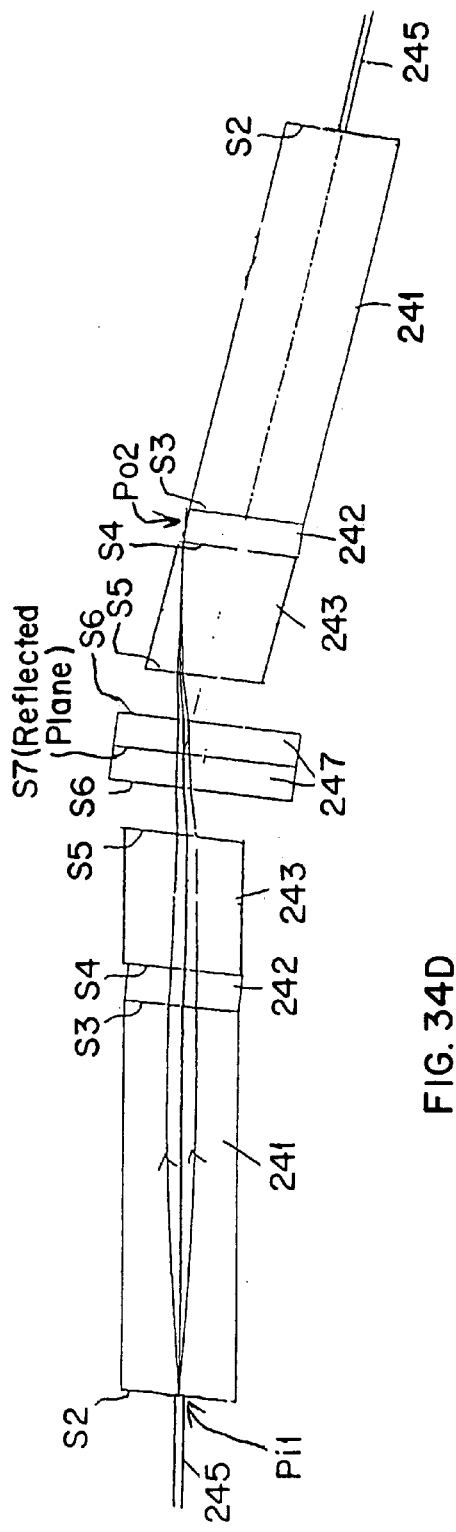

These points as above mentioned are now described. FIGS. 34A and 34B show optical paths when light from the single mode fiber 245 is reflected by a third surface once as an example. FIGS. 34C and 34D show optical paths when light from the single mode fiber is reflected by a seventh surface once as an example.

FIG. 34A and FIG. 34C show the order in which the reflection of light occurs within the respective optical systems after the light is emitted from the respective single mode fiber 245. FIG. 34B and FIG. 34D are schematic views of the respective optical systems folded back relative to the respective reflected planes (S3, S7) in an axially symmetrical manner in order to help understand the respective paths of reflected light. When a surface from which light is reflected is planar as in the present embodiments, it is enabled to follow the path of reflected light by folding back an optical system relative to the light reflected surface plane in an axially symmetrical manner.

In these embodiments, the right and left optical systems with the reflected plane interposed therebetween shown in FIG. 34B and FIG. 34D respectively do not level off with each other. This is because S3 (the boundary surface between the single mode fiber 245 and the refractive index distribution lens 241) and S7 (the outer surface of sheath 247) have been polished to be slanted. It should be noted that in each figure, light is emitted from the single mode fiber depicted on the left side.

The light emitted from the single mode fiber 245 advances to the position Pi1 which is on the surface side of the single mode fiber of the refractive index distribution lens. Light emitted from a single mode fiber 245 disperses at an angle smaller than a predetermined angle. In each of these embodiments, since there is refractive index distribution lens 241 provided next to single mode fiber 245, the light emitted from the single mode fiber 245 advances to reflected plane S3 (or S7) while gradually gathering within the refractive index distribution lens 241. In each embodiment, the light impinged on reflected plane S3 (or S7) bounces back in a direction different from that in which the light has traveled because the reflected plane S3 (or S7) has been polished to be slanted relative to the light. (Note that in FIG. 34B and FIG. 34D, the light is depicted in a manner to pass through the reflected plane.)

In the embodiment shown in FIG. 34A and FIG. 34B, when light arrives at a surface of reflection coplanar with the end face of the single mode fiber 245, the light is off center located away from) the single mode fiber 245 and exits at position Po1. In this way, the light impinging on reflected plane S3 and undergoing one reflection will not bounce back into the single mode fiber.

In the embodiment shown in FIG. 34C and FIG. 34D, the light bounced back by reflected surface S7 impinges on a side of Faraday rotator 242 (position Po2) and shielded. Therefore, the light reflected from S7 will not return to single mode fiber 245.

According to the structure of the present invention, it is possible not to return the light reflected once to the single mode fiber. According to the present invention, it is possible that the light from the single mode fiber is eclipsed after reflecting by the end surface of the optical element and is returned to a place shifted from the single mode fiber by making a flux of the signal light through the end surface of the optical element not be perpendicular to the end surface, as a result, a S/N ratio is improved.

Further, according to the present invention, the optical axis of the refractive index distribution lens of the optical end system on the side of the signal light agrees with the optical axis of the single mode fiber, and all the end surfaces on the side of an object of single mode fibers as above mentioned and of the optical element in the optical end system on the side of the signal light are slantedly polished in the same direction.

This point will be described by reference to FIGS. 35A, 35B, 35C and 35D.

Figure 35A:
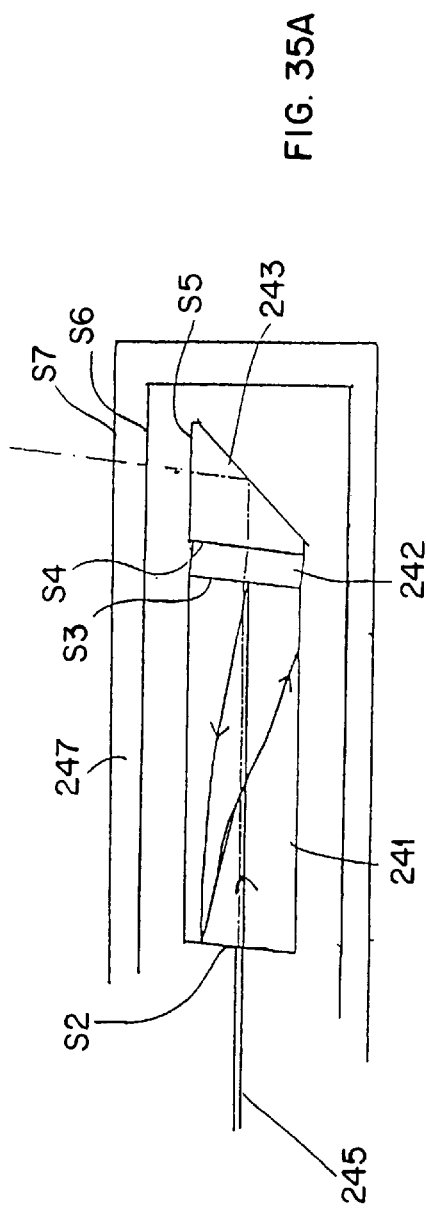
Figure 35B:
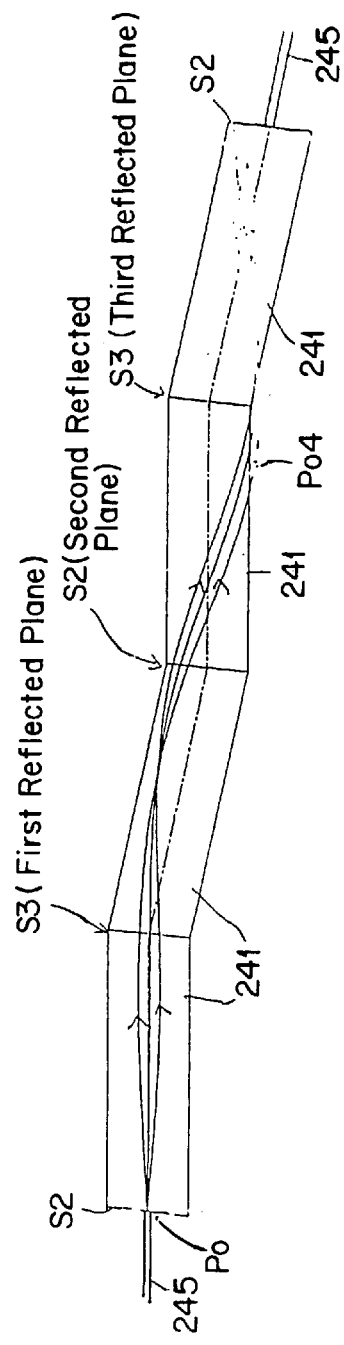

They show an example of a path when reflected three times, that a single mode fiber S3 surface (on the side of an object of a refractive index distribution lens), S2 surface (on the side of a fiber of the refractive index distribution lens), S3 surface (on the side of the object of the refractive index distribution lens), a path of the single mode fiber, wherein FIG. 35A is the case that the end surfaces of the refractive index distribution lens are slanted in the same direction, and FIG. 35B is the case that the end surfaces of the optical element are slanted in different directions (all the slantedly polished angles are 6).

Figure 35C:
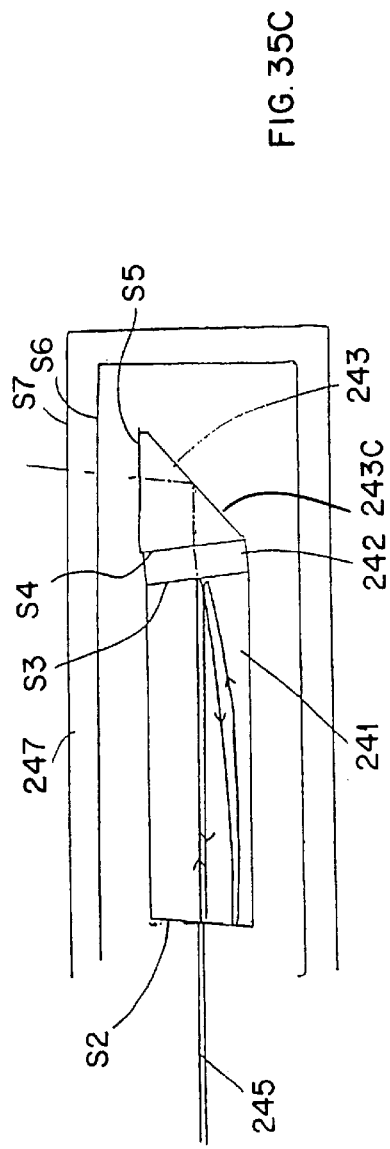
Figure 35D:
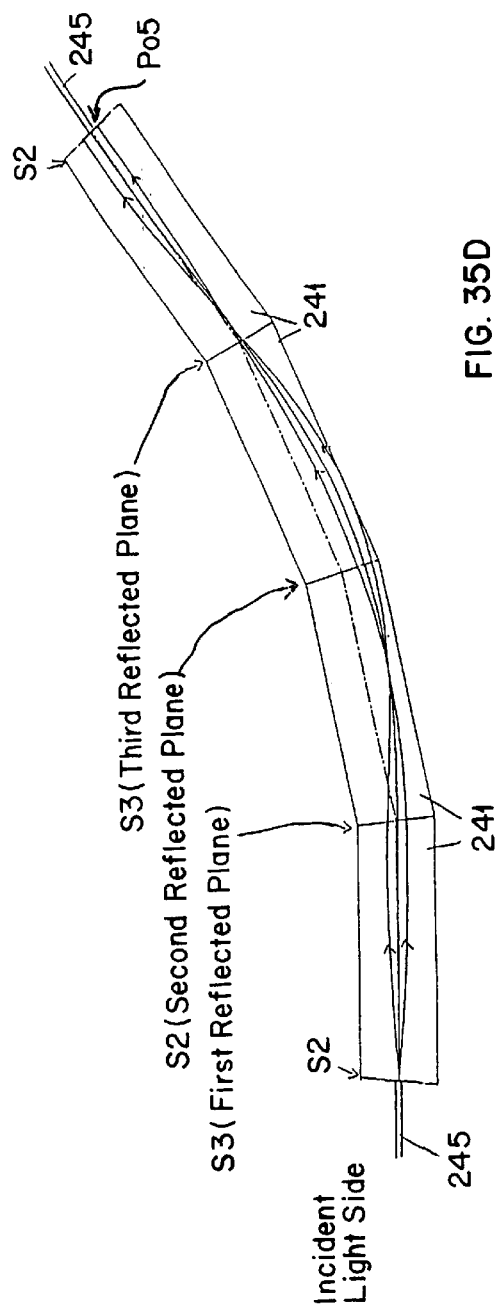

Similar to the above description, FIG. 35A and FIG. 35C show the order in which the reflection of light occurs within the respective optical systems after the light is emitted from the respective single mode fibers. FIG. 35B and FIG. 35D are schematic views of the respective optical systems folded back relative to the respective reflected planes in an axially symmetrical manner in order to help understand the respective paths of reflected light. It should be noted that in FIG. 35B and FIG. 35D, the light is emitted from the respective single mode fibers depicted on the left side.

In FIGS. 35A, 35B, 35C, and 35D, the light emitted from single mode fiber 245 passes through S2, advances within refractive index distribution lens 241, and arrives at S3. The light arriving at S3 is reflected back and arrives at S2. The position of the light reflected back to S2 is located at the position Po3 which is away from the center (optical axis of refractive index distribution lens 241) because S3 has been polished to have a slanted surface relative to the light.

The light bounced back by S2 again advances toward S3. In the configuration of the present invention as shown in FIGS. 35A and 35B in which S2 and S3 have been arranged so that their slanted surfaces orient in the same direction, the light immediately after being reflected from S2 advances at a large angle relative to the optical axis of refractive index distribution lens 241. While returning through refractive index distribution lens 241 toward S3, therefore, the light impinges on a side of the lens (position Po4) and shielded.

In this way, the reflected light will not return to the single mode fiber. In contrast, in the configuration as in FIG. 35C and FIG. 35D, which is not according to the present invention, the light immediately after being reflected from S2 advances in substantially parallel with the optical axis of refractive index profile lens 241. Thus the light travels along the optical axis of refractive index profile lens 241 and arrives at S3 again. The light is then reflected from S3 once again and arrives at the position Po5 on the surface of the side of the single mode fiber 245 of the refractive index distribution lens and ultimately returns to the single mode fiber. Therefore, a ghost image appears in the configuration as shown in FIG. 35C.

Therefore, it is understood that there is an effect that does not return the reflected light that the number of times of reflection is less than three times on the end surface of the optical element to the single mode fiber by polishing slantedly all the end surfaces on the side of the object of the single mode fiber and all the end surfaces of the refractive index distribution lens in the same direction to the optical axis of the refractive index distribution lens.

Further, in the end optical system on the side of the signal light of the light tomography diagnosis device according to the present invention, the most exterior side of the end optical system on the side of the signal light includes a sheath, a flux of the signal light is slantedly incident on the sheath, the incident angle to the normal line of the sheath of the main light of the signal light incident on the sheath is larger than 10 to prevent the light reflected three times in the sheath from returning to the single mode fiber. Here, the chief light ray of the signal light incident on the sheath means the trace of the light which has proceeded on the optical axis inside of the single mode fiber.

A method for making the incident angle to the normal line of the sheath of the main light of the signal light larger than 10° is to set the angle of the normal line of the surface 243C of the prism 243 that is the optical element for deflecting the observing direction to 48.5°.

Figure 36A:
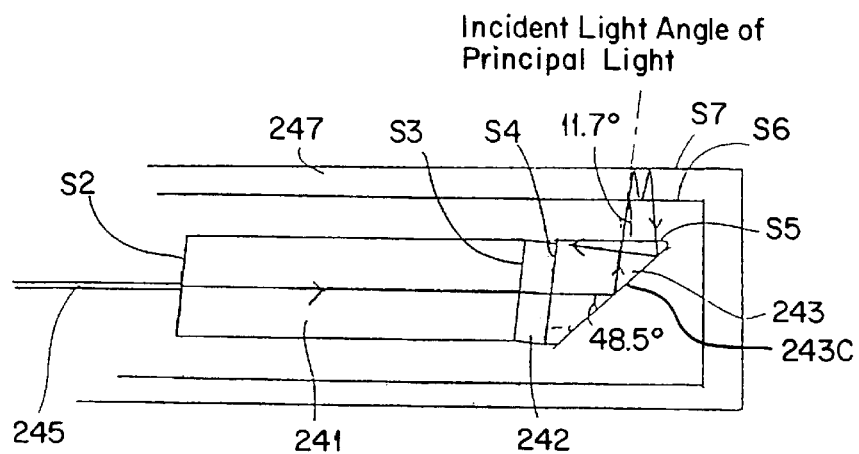
Figure 36B:
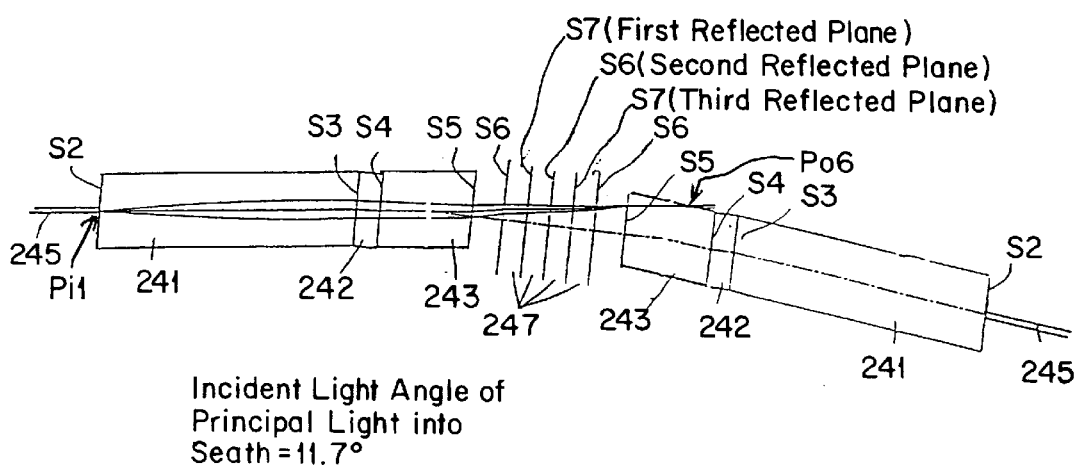
Figure 36C:
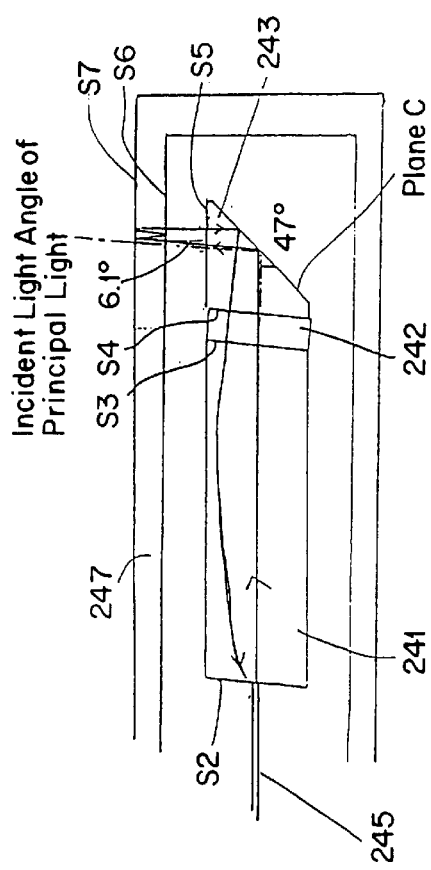

FIGS. 36A–36D show the path when the light is reflected three times in a sheath, that is to say, a single mode fiber, a seventh surface (on the side of an object of the sheath), a sixth surface (on the side of a fiber of the sheath), the seventh surface (on the object side of the sheath) and the single mode fiber FIG. 36A is structure according to the present invention, wherein the incident angle of the main light to the sheath is made 11.7° by making the angle of the normal line of the surface 243C of the prism 243 to the optical axis of the refractive index distribution lens 48.5°. FIG. 36C is against the structure of the present invention, that is to say, the angle of the normal line of surface 243C of the prism 243 to the optical axis of the refractive index distribution lens is 47°, and the incident angle of the main light to the sheath is 6.1°.

Figure 36D:
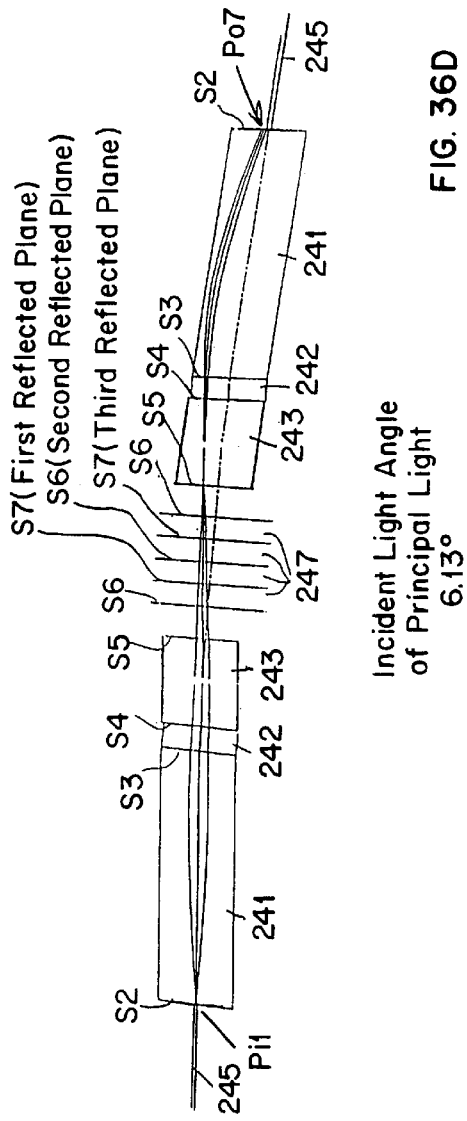

FIG. 36A and FIG. 36C show the order in which the reflection of light occurs within the respective optical systems after the light is emitted from the respective single mode fibers. FIG. 36B and FIG. 36D are schematic views of the respective optical systems folded back relative to the respective reflected planes in an axially symmetrical manner in order to help understand the respective paths of reflected light.

The light emitted from single mode fiber 245 passes through refractive index distribution lens 241, Faraday rotator 242, and prism 243, then arrives at outer surface S7 of sheath 247.

The light arriving at S7 is reflected and impinges on inner surface S6 of sheath 247. The light reflected from S6 bounces back to outer surface S7 of sheath 247 again. The light reflected from the surface once again now advances toward single mode fiber 245. At this time, conditions are set as follows. End face 243C of prism 243 has been made to have an angle of more than 45 degrees, as shown in FIG. 36A. The angle of incidence on the sheath has been set to be more than 10 degrees. Then, the light undergoing three internal reflections in the sheath, which ultimately advances toward the single mode fiber, is dislocated in a large amount from the light that is incident on the sheath the first time (this light advances outward). This causes the light to hit the sides of prism 243, Faraday rotator 242, and refractive index profile lens 241 (position Po6 in FIG. 35B). As a result, the light reflected from S7 the second time will not return to the single mode fiber.

In contrast, end face 243C of prism 243 has been made to have an angle of nearly 45 degrees shown in FIG. 36B. The angle of incidence on the sheath 247 has been set to be less than 10 degrees. Then, the light undergoing three internal reflections in the sheath 247, which ultimately advances toward the single mode fiber 245, is not so dislocated from the light that is incident on the sheath 247 first time (this light advances outward). Thus the light undergoing three internal reflections in the sheath passes through prism 243, Faraday rotator 242, and refractive index distribution lens 241 again and arrives at position Po7 which is the surface on the side of object of the single mode fiber 245. The result is a ghost image.

As known from FIG. 36, though the light reflected three times is easy to return to the single mode fiber when the incident angle of the main light to the sheath is smaller than 10° as in FIG. 36B, as the reflected light is eclipsed by the side surface of the optical element when the incident angle of the main light to the sheath is larger than 10° as in FIG. 36A, it is possible not to return the light reflected three times to the single mode fiber.

As above mentioned, according to the structure of the present invention, it is possible that when the number of times of light reflection on the end surface of the optical element is less than three times and does not return to the single mode fiber, ghosts do not appear, and it is possible to obtain the end optical system of the optical tomography device with an S/N ratio that is good.

Embodiment 8

FIG. 37 shows a second embodiment of an end optical system on the side of the signal light of an optical tomography diagnosis device according to the present invention. FIG. 38 is FIG. 37 linearly redrawn so that an angle to an optical axis of a refraction index distribution lens with a light gathering effect is easy to be understood.

An end part on the side of the signal light according to the present invention includes a single mode fiber 245 on the side of the signal light, a refractive index distribution lens 241 with a light gathering effect, a Faraday rotator 242, prism 243 that is an optical element for deflecting the direction of observing and a sheath 247. It is different from the seventh embodiment that the single mode fiber is equipped apart from the refractive index distribution lens, therefore, it is possible to adjust a position for gathering the signal light.

Data of the eighth embodiment according to the present invention will be shown as follows. Symbolic references are the same as those of the seventh Embodiment.

Data of Embodiment 8

A single mode fiber NA=0.13, f=8, arcsin(NA/n)=5.1
Decentering amount between optical axes of a single mode fiber and a refractive index distribution lens=0
An incident angle on a normal line of chief light ray: 11.3°

| s | R | d | n | θs | ER | Note |
|---|---|---|---|---|---|---|
| S1 | ∞ | — | 1.46 | — | 0.005 | A single mode fiber |
| S2(*4) | ∞ | 0.4 | 1 | 8 | 0.005 | Air |
| S3 | ∞ | 2.63 | *1 | 8 | 0.5 | A refractive index distribution lens |
| S4 | ∞ | 0.31 | 2.36 | 8 | 0.5 | A Faraday rotator |
| S5 | ∞ | 1.15 | 1.854 | 8 | 0.5 | A Prism |
| S6 | ∞ | 0.4 | 1 | 8 | | |
| S7 | *2 | 0.3 | 1.53 | 8 | | A Sheath |
| S8 | *3 | — | 1 | 8 | | |

*1 A refractive index distribution lens n = 1.592 √A = 0.597
*2 A cylindrical surface Ra = ∞ Rr = −0.9
*3 A cylindrical surface Ra = ∞ Rr = −1.2
*4 An end surface of the single mode fiber According the present embodiment, the end surface of each of the optical elements is not perpendicular to a flux of an incident signal light so that when the number of times of light reflection between end surfaces of each of the optical elements in an end optical system on the side of the signal light is less than three light does not return to the single mode fibers. Substantially, the end surfaces of all the optical elements of the end optical system on the side of the signal light, that is to say, the single mode fibers, both ends of the refractive index distribution lens, both ends of the Faraday rotator, the end surfaces on the incident and the outgoing side of prism are slantedly polished to the optical axis of the refractive index distribution lens respectively.

As above mentioned, by slanting the end surface of each optical element to the optical axis of the refractive index distribution lens, it is possible that the light reflected once does not return to the single mode fiber and the S/N ratio is improved.

Further, in the end optical system on the side of the signal light of the optical tomography diagnosis device, the end surfaces on the side of the object of the single mode fiber and the end surfaces of the refractive index distribution lens are wholly slantedly polished in the same direction. Furthermore, the present embodiment is constructed to satisfy the following conditions 1 and 2 on all the planes of each optical element.

$\theta_f > \arcsin (NA/n)$ (Condition 1)

$\theta_s \geq \theta_f$ (s=1,2, ... m) (Condition 2)

However,

NA represents NA of light radiated into air in case of polishing perpendicularly an end surface of a single mode fiber, n is the refractive index of a core of the single mode fiber, $\theta_f$ is the angle of the normal line of an end surface on the side of the object of the single mode fiber to the optical axis of the single mode fiber, and $\theta_s$ is the angle of the normal line of the end surface s of the optical element of the end optical system on the side of the signal light to the optical axis of refractive index distribution lens as above mentioned, and m is the number of border surfaces of the end optical system on the side of the signal light.

Condition 1 is the condition for preventing the reflected light from the end surface on the side of the object of the single mode fibers from returning to the place where the reflected light is composed. As the light reflected by the end surface on a side object of the single mode fiber to the optical axis of the single mode fiber at a large angle when the angle of the end surface of the single mode fiber satisfies condition 1, the light is not totally reflected between the core of the single mode fiber and a clad. Therefore, the reflected light is sufficiently attenuated until it reaches a coupler and the S/N ratio is not aggravated. On one hand, as the light reflected by the boundary surface between the single mode fiber and air returns to the optical axis of the fiber at a small angle when the angle of the end surface of the single mode fiber does not satisfy the condition 1, total reflection repeats in the single mode fibers, the reflected light reaches the coupler for composing the reference light and the signal light. Therefore, the S/N ratio is aggravated.

Condition 2 is the condition for preventing the light reflected less than three times from returning to the single mode fiber. As the reflected light flies to the optical axis of the refractive index distribution lens at the large angle when the angle of the end surface of the optical element satisfies (Condition 2), the light is eclipsed on the side surface and is easy to come off from the effective diameter of the single mode fiber.

FIGS. 39A and 39B show the path of a single mode fiber (s2 surface)→the end of the surface on the side of the single mode fiber of the refractive index distribution lens (s3 surface) the end surface of the single mode surface (s2 surface).

FIG. 39A satisfies all of the conditions 1 and 2 ($\theta_f=8°$, $\theta_4=\Delta_5=8°$), which is according to the present invention, and FIG. 39B satisfiesthe condition 1, but does not satisfy the condition 2 (f=8°, $\theta_4=\theta_5=3°$), which is not according to the structure of the present invention.

In this embodiment, an air layer is provided between single mode fiber 245 and refractive index profile lens 241. This produces a path of light that is emitted from the slanted end of the single mode fiber, impinged on and reflected back from end surface S3 of refractive index distribution lens 241, which is located on the single mode fiber side.

If the angle of slanted surface S3 (on the single mode fiber side of refractive index distribution lens 241) meets condition 2 as shown in FIG. 39A, the light impinged on S3 is reflected to positions away from the single mode fiber 245 (the light arrives at the position Po8 in FIG. 39A) despite the fact that it disperses outwardly. As a result, the light reflected once from S3 does not bounce back into the single mode fiber. An optical system with a good signal-to-noise ratio is thus configured. If the angle of slanted surface S3 (on the single mode fiber side of refractive index distribution lens 241) does not meet condition 2 as shown in FIG. 39B, part of the light reflected from S3 to disperse outwardly returns to the single mode fiber (the light arrives at the position Po9 in FIG. 39B). Thus the light reflected once from S3 bounces back to the single mode fiber, resulting in a worse signal-to-noise ratio.

To prevent light undergoing three reflections from returning to the single mode fiber, the optical devices should be arranged in such a manner (not shown) that their slanted end faces are oriented in the same direction because of the reason similar to that in the first embodiment. In addition, each end face should be polished so that the angle of slant becomes more than theta f.

As known from the example as above mentioned, it is possible not to return the light reflected on the end surface to the single mode fibers by satisfying the conditions 1 and 2 about the angles of the single mode fibers and the end surface on the side of the object.

Further in the present embodiment, similarly to embodiment 7, the light reflected three times in the sheath does not return to the single mode fiber by making the angle of the main light incident on the sheath to the normal line of the sheath larger than 11.3° and by making the angle between the optical line of the refractive index distribution lens and the normal line of the C surface of the prism 48.5°.

Embodiment 9

FIG. 40 shows a ninth embodiment of an end optical system on the side of a signal light of an optical tomography diagnosis device according to the present invention. FIG. 41 is FIG. 40 linearly redrawn so that an angle to an optical axis of a refraction index distribution lens with a light gathering effect is easy to be understood.

The end part on the side of the signal light according to the present embodiment includes a single mode fiber 245 on the side of a signal light, a refractive index distribution lens 241 with a light gathering effect, a Faraday rotator 242, prism 243 and a sheath 247. It is different from the seventh and eighth embodiments in that the optical axis of the single mode fiber is decentered to the optical axis of the refractive index distribution lens.

Data of the ninth embodiment according to the present invention is as follows: Symbolic reference is the same as that of Embodiment 7.

Data of Embodiment 9

A single mode fibers NA=0.13, arcsin(NA/n)=5.1°

Decentering amount between optical axes of the single mode fiber and a refractive index distribution lens=−0.24.

An incident angle on a normal line of a sheath of main light: 11.8°

| s | R | d | n | θ | ER | Note |
|---|---|---|---|---|---|---|
| S1 | ∞ | — | 1.46 | — | 0.005 | A single mode fiber |
| S2(*4) | ∞ | 0.4 | 1 | 8 | 0.005 | Air |
| S3 | ∞ | 2.63 | *1 | 8 | 0.5 | A refractive index distribution lens |
| S4 | ∞ | 0.31 | 2.36 | 0 | 0.5 | A Faraday rotator |
| S5 | ∞ | 1 | 1.854 | 0 | 0.5 | A Prism |
| S6 | ∞ | 0.4 | 1 | 0 | | |
| S7 | *2 | 0.3 | 1.53 | 0 | | A Sheath |
| S8 | *3 | — | 1 | 0 | | |

*1 A refractive index distribution lens n = 1.592 √A = 0.597
*2 A cylindrical surface Ra = ∞ Rr = −0.9
*3 A cylindrical surface Ra = ∞ Rr = −1.2
*4 An end surface of the single mode fiber According to the present embodiment, the end surface of each of the optical elements is not perpendicular to a flux of an incident signal light so that when the number of times of light reflection between the end surfaces of each of optical elements in an end optical system on the side of the signal light is less than three times, light does not return to the single mode fiber.

Consequently, the reflected light from the end surface of the optical element of the end optical system does not return the single mode fiber by decentering the optical axis of the single mode fiber to the optical axis of the refractive index distribution lens that is the optical element with a light gathering effect.

When shifting the optical axes of the refractive index distribution lens and the single mode fiber, the flux of the light from the single mode fiber, as in FIG. 41, passes through the place shifted from the optical axis on the side of the fiber of the refractive index distribution lens. The light incident on the place shifted from the optical axis of the refractive index distribution lens is bent in the refractive index distribution lens, including the side of the object of the refractive index distribution lens, strikes slantedly on the Faraday rotator on the side of the object and the end surface of the prism, and it is possible to prevent the light reflected less than three times on each end surface from returning to the single mode fiber.

As the flux of signal light is slanted to the optical axis of the refractive index distribution lens on the end surface on the side of the object of the refractive index distribution lens and the end surface of the optical element on the side of the object nearer it than it when decentering of the optical axis of the single mode fiber to the optical axis of the refractive index distribution lens, it is possible to prevent the reflected light from returning to the single mode fiber even if the end surface on the side of the object of the refractive index distribution lens and the end surface of the optical element on the side of the object nearer it are perpendicular to the optical axis of the refractive index distribution lens.

Further, when decentering the optical axis of the single mode fiber to the optical axis of the refractive index distribution lens, it is possible to make the flux of the signal light incident on the sheath slantedly even if using the prism that decenters the observing direction by a normal 90°.

According to the present embodiment, by decentering the optical axis of the single mode fiber to the optical axis of the refractive index distribution lens by −0.24, even if using a normal prism with the angle to the optical axis of the refractive index distribution lens of the normal line of the sloping surface of the prism at 45°, it is possible to make the incident angle of the chief light ray of the signal light to the sheath 11.8°.

On one hand, when the end surface on the side of the single mode fiber of the refractive index distribution lens and the end surface of optical element between the single mode fiber and the refractive index distribution lens are perpendicular to the optical axis of the refractive index distribution lens, there is the case that signal light strikes perpendicularly on the end surface of the optical element and the reflected light returns to the single mode fiber. In order to avoid this problem, set the angle of the end surface of each optical element to satisfy the following conditions 1 and 3.

$\theta_f > \arcsin(NA/n)$ (Condition 1)

$\theta_g \geq \theta_f$ (Condition 3)

However,

NA represents NA of light radiated into air in case of polishing perpendicularly the end surface of the single mode fiber, n is the refractive index of the core of the single mode fiber, f is the angle of the normal line of the end surface on the side of the object of the single mode fiber to the optical axis of the single mode fiber, and p1 g are angles of the normal line of the end surface on the side of the single mode fiber of the refractive index distribution lens and the normal lines of the end surfaces of all the optical elements between the single mode fiber and the refractive index distribution lens to the optical axis of the refractive index distribution lens.

Condition 1 is the condition for preventing the reflected light from the end surface on the side of the object of the single mode fiber from returning to the place where the reflected light is composed with the reference light, similarly to Embodiment 8.

Condition 3 is the condition for shifting the light reflected from the end surface on the side of the single mode fiber of the refractive index distribution lens and from the optical element on the side of the single mode rather than the surface.

Then, it is preferable that the refractive index distribution lens, according to the present embodiment, is positioned adjacent to the single mode fiber by holding an air layer to or is directly cemented to the single mode fiber. By the arrangement as above mentioned, it is not necessary to polish slantedly the end surface except the single mode fiber and the side of the single mode fiber of the refractive index distribution lens, and it is easy to process.

According to embodiments 7 to 9, it is possible to provide an end optical system on the side of signal light of OCT that there is no ghost, the S/N ratio is good, and ability to observe is excellent.

Next, an object of the tenth and eleventh embodiments is to assemble extremely precisely an optical scanning probe into which an optical system as shown in the seventh, eighth and ninth embodiments is integrated.

Embodiment 10

A tenth embodiment of the present invention will be described referring to FIGS. 42, 43A and 43B. The structure of the end part of an optical scanning probe is shown in FIGS. 42, 43A and 43B.

The end part 302 of an optical sheathe includes a flexible Teflon tube 320 and an end cap 305 for closing the opening of the end, and the Teflon tube 320 is adhered to the end cap 305. The Teflon tube 320 has light transmission at least on the side of the end. A lens unit 303 is constructed by adhering a prism 308, a Faraday rotator 309 and a GRIN lens 311 from the side of the end in order respectively. The prism 308 is designed so that an observing beam 317 outgoing from the prism 308 has an outgoing angle on the side of the end of the probe to the perpendicular of the cylindrical surface of the Teflon tube 320. The angle is set about 12 through 13. The distal end of a single mode fiber 301 is fixed to a ferrule 315 by adhesive 316. The ferrule 315 is constructed by making a radius small by shaving an outer peripheral surface on the side of a rear end.

The lens unit 303 is fixed by adhering to the ferrule 315 in a hollow housing 312, and the end surface on the side of the end of the single mode fiber 301 is adhered to the end surface on the side of the rear end of GRIN lens 311. Further, the end part of a flexible shaft 304 is inserted into the housing 312, and at the same time, is connected and fixed by adhesion by inserting a shaved part with a step 321 of the ferrule 315 and the single mode fiber 301 into the inner cavity 317.

As shown in FIG. 43A, a protective frame 310 is installed so that the lens unit 303 is held by both sides of the protective frame 310 on the side of the end of the housing 312. Further, a round cap 306 is adhered on the side of the end of the housing 312. The round cap 306 includes an opening part 307 so that it is possible to transmit the observing beam.

The surfaces of both ends of GRIN lens 311 are slantly polished and the surfaces of both ends are parallel to each other. The end of the ferrule 315 is slantly polished at the same angle of the GRIN lens 311, too. Therefore, the contact surfaces between the prism 308 and the Faraday rotator 309, between the Faraday rotator 309 and the GRIN lens 311 and between the GRIN lens 311 and the ferrule 315 are in parallel to each other, and the perpendicular of the contact surface is at a fixed angle to an optical axis O. The angle is set to about 6°.

The vertices on the side of the acute angle of the end surface on the side of the rear end of the GRIN lens 311 and on the side of the obtuse of the end surface of the ferrule 315 are each shown by a marking 313. Further, the housing 312 is provided with a recognizing hole 314 near the contact part between the GRIN lens 311 and the ferrule 315.

Next, the action of tenth embodiment will be explained. Light which is guided into a single mode fiber 301 leaves from the end surface of a ferrule 315 is incident on GRIN lens 311, transmitted through a Faraday rotator 309, changed in direction by a prism 308, becomes an observing beam 317 transmitting through a sheath 320 and is collected to a focus 318. It is possible to change a focal position 319 by changing the longitudinal length of the GRIN lens 311.

As each contact surface between the prism 308, the Faraday rotator 309, GRIN lens 311 and ferrule 315 has a fixed angle to the direction perpendicular to the optical axis respectively, the optical axes of reflected light and multiple reflected light which comes out on each contact surface is shifted from the optical axis O and does not return to the single mode fiber 301.

As an observing beam 317 has the outgoing angle θ to the perpendicular of the cylindrical surface of the Teflon tube 320, reflected light and multi reflected light occurred on an outer surface does not return to the single mode fiber 301.

Further, when practically observing the tissue of a living body with OCT during an endoscopy procedure, the tissue of the living body is often observed with the probe tip at an angle to the lumen of the tract under examination rather than parallel to it. Therefore, there are advantages that as the outgoing angle θ of the observing beam 317 is directed at an angle to the axis of the probe, the observing beam 317 is possible to be almost perpendicularly incident on the tissue of the living body and it is possible to obtain a more accurate OCT image.

As shown in FIG. 43B, upon noting recognizing the markings 313 from the recognizing hole 314 when adhering the contact surface between the GRIN lens 311 and the ferrule 315, it will be possible to adjust the phases of the slantly polished surfaces of the GRIN lens 311 and the ferrule 315. At the same time, it is possible to remove adhesive forced out from the recognizing hole 314.

Further, as the lens unit 303 is integrally contacted with the ferrule 315 through the housing 312, it is possible to agree easily and surely with the optical axis O.

As shown in FIG. 43A, as the lens unit 303 is protected by the protective frame 310 installed on the housing 312, it is possible to reduce the danger of damaging the lens unit 312 when assembling, such as adhering the round cap 306 to the housing 312. Further, at the same time, it is possible to secure a tab for sticking of the round cap 306 to the housing 312 by the protective frame 310.

According to the tenth embodiment, as light reflected by an optical element is not returned to an optical fiber, the ratio S/N of a system is advanced. Further, it is possible to assemble in relation to correct positions and phases and to secure performance according to an optical design. Further, it is possible to advance assembling and productivity.

Embodiment 11

An eleventh embodiment according to the present invention is described with reference to FIGS. 44 through 45B.

FIG. 44 shows another embodiment of an optical scanning probe in that each optical element is slantly contacted. And FIGS. 45A and 45B show cross-sections as indicated in FIG. 44.

Though the structure of FIG. 44 is fundamentally the same as that of FIG. 42, there are differences at the points as follows. First, a mirror 323 adhered to a round cap 306 is installed instead of a prism 308, and an outgoing angle to the perpendicular of the cylindrical surface of the Teflon tube of an observing beam 317 outgoing from the mirror is directed in the side of the rear end. Next, though the perpendicular of both surfaces slantly polished of a GRIN lens 311 is at an angle to an optical axis O, they are polished at different angles respectively. Therefore the contact surface between a Faraday rotator 309 and a ferrule 315 has a different angle. Further, instead of providing the marking 313 and a recognizing hole 314, the D cut 324 as shown in FIG. 45A is provided on the cylindrical surface of the vertex on the side of an obtuse of the surface slantly polished on the side of the rear end of the GRIN lens 311. D cut 324 as shown in FIG. 45B is provided on the cylindrical surface of the vertex on the side of an acute angle of the surface slantly polished on the side of the point end of the ferrule 315 respectively, and the D cut 324 is also provided at the position respectively corresponding to the inner cavity of a housing 312.

Next, the action of the eleventh embodiment will be explained. Though fundamentally same as the tenth embodiment, there are differences at the following points.

As the perpendicular of each contact surface is at an angle to an optical axis O, even if the polishing angle of the end surface of each optical element is different as the structure of FIG. 45, similarly to the tenth embodiment, the action is not different in that the reflected light and the multi reflected light on each contact surface does not directly return to a single mode fiber 301.

When adhering a round cap 306 to a housing 312, it is possible to change a focal position 319 by changing an inserted interval 331. Though the outgoing angle θ of an observing beam 317 is directed on the side of the rear end, action is the same as in embodiment 10 in that the reflected light and the multi reflected light occur on an inner and an outer surface of a Teflon tube 320 does not directly return to the single mode fiber 301.

As the phase of each contact surface slantly polished is matched by the D cut 324 in inserting when adhering the end surface of the GRIN lens 311 to the end surface of the ferrule 315 in a housing 324, it is possible to surely contact both surfaces only by inserting each element by adjusting to the D cut 324.

According to the eleventh embodiment, in addition to the same effects as those of the tenth embodiment, it is possible to adjust a focal position when assembling. Further, setting of the phases of slantly polished surfaces is easy compared to the tenth embodiment and assembling is advanced.

Embodiment 12

A twelfth embodiment of the present invention is described in reference to FIGS. 46A through 48B. A schematic view of the side surface of the end part of an optical scanning probe is shown in FIG. 46B, and a schematic view when viewing the optical scanning probe from the side of the end is shown. in FIG. 46A.

The end part of the optical scanning probe is constructed by contacting a single mode fiber 301, a GRIN lens 311 and a prism 308 from the rear end to the inside of a Teflon tube 320. On the light exiting surface of the prism 308, a cylindrical lens part 334 is provided with a cylindrical convex surface 332 so that the peripheral direction of a probe is a curved surface.

The structure of FIGS. 47A and 47B is the same as that of FIGS. 46A and 46B except that the curvature of the cylindrical convex surface 332 is large. The structure of FIGS. 48A and 48B is the same as that of FIGS. 46A and 46B except that the cylindrical convex surface 332 is provided in the longitudinal direction. The cylindrical lens part 334 of FIG. 46A through FIG. 48B may be provided by polishing the prism 308 or by adhering a cylindrical convex lens to the prism.

Next, the action of the twelfth embodiment will be explained. First, the action of the structure of FIGS. 46A and 46B is described. Light guided into a single mode fiber 301 is incident on a GRIN lens 311, the optical path of it is changed by a prism 308 and the light becomes an observing tube 317 transmitting through a Teflon tube 320.

Here, for descriptive purpose, it is defined that the peripheral direction of the cylindrical surface of the Teflon tube 320 is the X axis and the direction of the major axis of the cylindrical surface of the Teflon tube 320 is the Y axis. Though the curved surface of the Teflon tube 320 has a concave lens effect in the direction of the X axis of the observing beam 317, if it is designed that a cylindrical convex surface 332 cancels the effect, it will be possible to make the focal position 319a of the X-axis of the observing beam 317 agree with the focal position 319b of the Y-axis.

As in the structure of FIGS. 47A and 47B, the curvature of the cylindrical convex surface is larger than that of the structure of FIGS. 46A and 46B, power of the convex lens effect of the cylindrical convex surface 332 is stronger than that of the concave lens effect of the Teflon tube 320, and it is possible to make positively the focal position 319a of the Y axis shorter than the focal position 319b of the X axis of the observing beam 317.

As in the structure of FIGS. 48A and 48B, since the focal position 319a of the X axis is moved away by the concave lens effect of the Teflon tube 320 and the focal position 319b of the Y axis is moved closer by the cylindrical convex surface 332, it is possible to more positively separate the distance between focal positions 319a and 319b.

According to the twelfth embodiment, the S/N ratio is advanced by concentrating the energy density of an observing beam. Further, observing depth is advanced by dispersing the energy density of the observing beam.

Embodiment 13

A thirteenth embodiment of the present invention is described referring to FIGS. 49A to 50B. The structure of FIGS. 49A and 49B is the same as that of the twelfth embodiment except that a convex lens 325 is provided instead of a GRIN lens 311, there is no cylindrical convex surface 332 of a prism 308, and a cylindrical concave lens 326 is installed between the convex lens 325 and a single mode fiber 301. The cylindrical concave lens 326 is disposed so that it has a concave lens effect in the direction of the Y axis to an observing beam 317 as shown in FIG. 49B.

The structure of FIGS. 50A and 50B is the same as that of FIGS. 49A and 49B except for disposing of the cylindrical concave lens 326 between the prism 308 and the convex lens 325 and in the direction that gives the concave lens effect in the direction of the X axis of the observing beam 317.

Next, the action of the thirteenth embodiment is described. In the structure of FIGS. 49A and 49B, as a cylindrical concave lens 326 has a concave lens effect in the direction of the Y axis of an observing beam 317, a Teflon tube 320 has the concave lens effect in the direction of the X axis of an observing beam. If designing the curvature of a cylindrical concave surface 333 so that power of the concave lens effects of both of them are agreed, it is possible to agree the focal position 319a on the X axis with the focal position 319b on the Y axis. If the curvature of the cylindrical concave surface 333 is larger, the power of the concave lens effect of the cylindrical concave lens 326 is higher than that of the Teflon tube 320, and it is possible to move positively the focal position 319b on the Y axis away rather than the focal position 319a on the X axis.

In the structure of FIG. 50, as both of the cylindrical concave lens 326 and the Teflon tube 320 have the concave lens effect in the direction of the X axis of the observing beam 317, it is possible to move positively the focal position 319a on the X axis away rather than the focal position 319b on the Y axis.

According to the thirteenth embodiment, in addition to the same effects as the twelfth embodiment, further, as a GRIN lens is not used, it is possible to shorten the length of the probe tip which cannot be bent.

Embodiment 14

A fourteenth embodiment will be described of the present invention referring to structure FIGS. 51A through 52B. The structure thereof is the same as that of the 12th embodiment except that there is no cylindrical convex surface 332 of a prism 308 and a rolling processing ellipse GRIN lens 327 is disposed so that a cross section is an ellipse executed rolling processing instead of a GRIN lens 311.

As shown in FIG. 51A, a major axis of the ellipse GRIN lens 327 is disposed in the same direction as an observing beam 317, and in FIG. 52A, a minor axis of the ellipse GRIN lens 327 is disposed in the same direction as an observing beam 317.

Next, the action of the fourteenth embodiment is explained. It is possible to obtain the same action as that of the twelfth embodiment by replacing image focal points which are different in the directions of major and minor axes of an ellipse of light incident on an elliptical GRIN lens 327 according to the present invention as the action of the cylindrical convex surface 332 executed to the prism in the twelfth embodiment.

According to the fourteenth embodiment, in addition to the same effects of the 12th embodiment, further, as using rolling processing of a GRIN lens in order to provide a cylindrical lens effect, it is not necessary to polish an optical part. Therefore, it is possible to reduce manufacturing time and cost.

Embodiment 15

A fifteenth embodiment of the present invention is described in reference to FIGS. 53A through 54B. Their structure is the same as that of a twelfth embodiment except for the inclusion of a cylindrical convex mirror 328 inserted into a round cap 306 instead of a prism 308.

FIGS. 53A and 54A are views of a probe from the side of an end, and the cross section of a Teflon tube 320 and the end of the round cap 306 into which the cylindrical convex mirror 328 are seen.

In the structure of FIGS. 53A and 53B, the cylindrical convex mirror 328 is disposed in the direction of having a concave lens effect in the direction of the Y axis of an observing beam 317, and in the structure of FIGS. 54A and 54B, the cylindrical convex mirror 328 is disposed in the direction of having a concave lens effect in the direction of the X axis of an observing beam 317.

Next, the action of the fifteenth embodiment is explained. The cylindrical concave lens 32 of the thirteenth embodiment gives the same concave lens effect as that of the cylindrical convex mirror 328 of the present invention, and the same effect as that of the 13th embodiment is obtained. Further, it is possible to change 319a and 319b by the same distance by an inserting interval of a round cap 306.

According to the fifteenth embodiment, in addition to the same effects of those of the twelfth embodiment, further, it is possible to adjust the focal positions in assembling.

Embodiment 16

A sixteenth embodiment of the present invention is described in reference to FIGS. 55A through 56A. The structure of FIGS. 55A and 55B is the same as that of the twelfth structure except connecting a refractive index distribution board 329 instead of the cylindrical convex surface 332 of the outgoing surface of a prism 308.

The refractive index of the refractive index distribution board 329 is varied one-dimensionally to a contact surface, and becomes gradually lower outward from the center. It is possible to make by cutting down a GRIN lens and so on. The structure of FIGS. 56A and 56B is the same as that of FIGS. 55A and 55B except for connecting the refractive index distribution board 329 between the prism 308 and the GRIN lens 311.

It is disposed that the refractive index distribution board 329 is disposed so that in the structure of FIG. 55 it is possible to see the refractive index distribution direction 330 of the refractive index distribution board 329 from the side of an end as shown in FIG. 55A, and in the structure of FIG. 56, it is possible to see the refractive index distribution direction 330 of the refractive index distribution board 329 from the side surface as shown in FIG. 55B.

Next, the action of the sixteenth embodiment will be explained. The cylindrical convex surface 332 of the prism of the third embodiment has the same action as that of a refractive index distribution board 329, and others are the same as that of the third embodiment.

According to the sixteenth embodiment, in addition to the same effects as those of the twelfth embodiment, further, as it is possible to give a convex effect only by adding a refractive index distribution board to an optical system of a conventional embodiment, it is possible to divert conventional parts and optical design as they are and to reduce manufacturing time and costs.

While the invention has been described via numerous embodiments, the scope of this invention is not to be limited thereby, but by the scope of the appended claims.

What is claimed is:

1. An optical scanning probe comprising:
   an optical probe for being inserted into a body cavity;
   a light source for generating light to be irradiated onto a subject;
   an optical fiber for guiding the light from the light source to a distal end of the optical probe;
   light condensing means for condensing the light and to irradiate the light onto the subject;
   a distal end optical system provided in the distal end portion of the optical probe, comprising means for scanning the focus of the light condensed by the light condensor means to almost perpendicular direction to the optical axis of the light condensing means;
   separating means for separating the light returned from the subject from the light to the subject;
   light detecting means for detecting the return light separated by the separating means, wherein
   in the distal end optical system, a portion nearest to the subject comprises a transparent member having a set of almost parallel surfaces, and,
   flux of the condensed light slantedly arrives on the transparent member.

2. An optical scanning probe according to claim 1, wherein the transparent member is a sheath provided on outermost circumference of the optical probe.

3. An optical scanning probe according to claim 1, wherein an incident angle of a chief ray of the condensed light arriving on the transparent member to the normal line of either of the parallel surfaces is equal to or larger than 10 degrees.

4. An optical scanning probe according to claim 1, wherein the distal end optical system comprises at least one optical element for deflecting an observing direction by reflecting light, and a deflection angle of the optical element satisfies a condition that the flux of the condensed light slantedly arrives on the transparent member.

5. An optical scanning probe comprising:
   an optical probe for being inserted into a body cavity;
   a light source for generating light to be irradiated onto a subject;
   an optical fiber for guiding the light from the light source to a distal end of the optical probe;
   a light condensing member for condensing the light and irradiating the light onto the subject;
   a distal end optical system provided in the distal end portion of the optical probe, comprising a scanning device for scanning the focus of the light condensed by the light condensing member to an almost perpendicular direction to the optical axis of the light condensing member;
   a separating device for separating light returned from the subject from the light irradiated onto the subject;
   a light detecting device for detecting the return light separated by the separating device, wherein
   in the distal end optical system, a portion nearest to the subject comprises a transparent member having a set of almost parallel surfaces, and,
   flux of the condensed light slantedly arrives on the transparent member.

6. An optical scanning probe according to claim 5, wherein the transparent member is a sheath provided on an outermost circumference of the optical probe.

7. An optical scanning probe according to claim 5, wherein an incident angle of a chief ray of the condensed light arriving on the transparent member to the normal line of either of the parallel surfaces is equal to or larger than 10 degrees.

8. An optical scanning probe according to claim 5, wherein the distal end optical system comprises at least one optical element for deflecting an observing direction by reflecting light, and a deflection angle of the optical element satisfies a condition that flux of the condensed light slantedly arrives on the transparent member.

9. An optical probe device comprising:
   an observation light source for generating predetermined observation light to be irradiated onto a subject;

a first light guide for guiding the light generated by the observation light source, irradiating the light to the subject side, and guiding reflection light based on the observation light reflected from the subject;

a transparent member provided at least on an outer circumference of the first light guiding member on a side of the subject, transmits the observation light guided by the first light guide, wherein the transparent member is optically transparent;

a second light guide for emitting the observation light generated by the observation light source and guided by the first light guide to the transparent member at predetermined non-perpendicular angle, and for guiding the reflection light based on the observation light reflected on the subject to the first light guide; and an interference signal detector for detecting a predetermined interference signal by causing the interference between the reflection light reflected on the subject and guided by the second light guide and the first light guide and the observation light generated by the observation light source.

10. An optical probe device according to claim 9, wherein the second light guide emits the observation light at an angle equal to or more than 10 degrees to the normal line of the transparent member.

11. An optical probe device according to claim 10, further comprising:

a scanning member for scanning the light emitted from the second light guide onto the subject by moving the first light guide.

12. An optical probe device according to claim 9, wherein at least the first light guide is slidable on the transparent member.

13. An optical probe device according to claim 12, further comprising:

a scanning member for scanning the light emitted from the second light guide onto the subject by moving the first light guide.

14. An optical probe according to claim 9, wherein at least the first light guide comprises a single mode fiber.

15. An optical probe device according to claim 14, further comprising:

a scanning member for scanning the light emitted from the second light guide onto the subject by moving the first light guide.

16. An optical probe device according to claim 9, further comprising:

a scanning member for scanning the light emitted from the second light guide onto the subject by moving the first light guiding member.

* * * * *